(12) United States Patent
Davoodi et al.

(10) Patent No.: US 11,802,301 B2
(45) Date of Patent: Oct. 31, 2023

(54) COMPOSITIONS AND METHODS FOR PEPTIDE PRODUCTION

(71) Applicant: BioCatalyst LLC, Torrance, CA (US)

(72) Inventors: Jamshid Davoodi, Playa Del Rey, CA (US); Mohammed M. Davoodi, Playa Del Rey, CA (US)

(73) Assignee: BioCatalyst LLC, Torrance, CA (US)

( * ) Notice: Subject to any disclaimer, the term of this patent is extended or adjusted under 35 U.S.C. 154(b) by 0 days.

(21) Appl. No.: 18/063,064

(22) Filed: Dec. 7, 2022

(65) Prior Publication Data

US 2023/0193342 A1 Jun. 22, 2023

Related U.S. Application Data

(63) Continuation of application No. PCT/US2022/012384, filed on Jan. 13, 2022.

(60) Provisional application No. 63/137,612, filed on Jan. 14, 2021.

(51) Int. Cl.
| | |
|---|---|
| *C07K 14/605* | (2006.01) |
| *C12P 21/02* | (2006.01) |
| *C07K 14/62* | (2006.01) |

(52) U.S. Cl.
CPC ............ *C12P 21/02* (2013.01); *C07K 14/605* (2013.01); *C07K 14/62* (2013.01); *C07K 2319/20* (2013.01); *C07K 2319/50* (2013.01)

(58) Field of Classification Search
CPC ............ C07K 2319/50; C07K 2319/20; C07K 14/62; C07K 14/605
See application file for complete search history.

(56) References Cited

U.S. PATENT DOCUMENTS

| | | | | |
|---|---|---|---|---|
| 2005/0059053 | A1* | 3/2005 | Fischer | C07K 16/3007 435/7.1 |
| 2005/0255093 | A1* | 11/2005 | Shone | C12N 9/0089 424/94.4 |
| 2020/0216512 | A1* | 7/2020 | Hecht | C12P 21/02 |

FOREIGN PATENT DOCUMENTS

| | | | |
|---|---|---|---|
| CN | 101356275 | * | 1/2009 |
| WO | WO 2004098536 | * | 11/2004 |

* cited by examiner

*Primary Examiner* — Gyan Chandra
(74) *Attorney, Agent, or Firm* — UltimatEdge IP Law Group, P.C.; Dean G. Stathakis

(57) ABSTRACT

This disclosure concerns production of product peptides with a target amino acid sequence by proteolysis of a recombinant polypeptide comprising specific protease recognition sites or chemical cleavage sequences. In some embodiments, the product peptide is released from repeating peptide units in the recombinant polypeptide by removal of intervening amino acid sequences by proteolysis by proteases that recognize sites within the intervening amino acid sequences and a carboxypeptidase, aminopeptidase, and/or further protease.

20 Claims, 18 Drawing Sheets

Specification includes a Sequence Listing.

Enzyme 1

Enzyme 2 and Purification

```
                         SEQUENCE LISTING

Sequence total quantity: 202
SEQ ID NO: 1             moltype =         length =
SEQUENCE: 1
000

SEQ ID NO: 2             moltype =         length =
SEQUENCE: 2
000

SEQ ID NO: 3             moltype =         length =
SEQUENCE: 3
000

SEQ ID NO: 4             moltype =         length =
SEQUENCE: 4
000

SEQ ID NO: 5             moltype =         length =
SEQUENCE: 5
000

SEQ ID NO: 6             moltype =         length =
SEQUENCE: 6
000

SEQ ID NO: 7             moltype =         length =
SEQUENCE: 7
000

SEQ ID NO: 8             moltype =         length =
SEQUENCE: 8
000

SEQ ID NO: 9             moltype =         length =
SEQUENCE: 9
000

SEQ ID NO: 10            moltype =         length =
SEQUENCE: 10
000

SEQ ID NO: 11            moltype =         length =
SEQUENCE: 11
000

SEQ ID NO: 12            moltype =         length =
SEQUENCE: 12
000

SEQ ID NO: 13            moltype =         length =
SEQUENCE: 13
000

SEQ ID NO: 14            moltype =         length =
SEQUENCE: 14
000

SEQ ID NO: 15            moltype =         length =
SEQUENCE: 15
000

SEQ ID NO: 16            moltype =         length =
SEQUENCE: 16
000
```

```
SEQ ID NO: 17           moltype =    length =
SEQUENCE: 17
000

SEQ ID NO: 18           moltype =    length =
SEQUENCE: 18
000

SEQ ID NO: 19           moltype = AA   length = 4
FEATURE                 Location/Qualifiers
REGION                  1..4
                        note = Protease recognition site
source                  1..4
                        mol_type = protein
                        organism = synthetic construct
SEQUENCE: 19
RRRR                                                                    4

SEQ ID NO: 20           moltype = AA   length = 4
FEATURE                 Location/Qualifiers
REGION                  1..4
                        note = Protease recognition site
source                  1..4
                        mol_type = protein
                        organism = synthetic construct
SEQUENCE: 20
RKRR                                                                    4

SEQ ID NO: 21           moltype = AA   length = 4
FEATURE                 Location/Qualifiers
REGION                  1..4
                        note = Protease recognition site
source                  1..4
                        mol_type = protein
                        organism = synthetic construct
SEQUENCE: 21
RRKR                                                                    4

SEQ ID NO: 22           moltype = AA   length = 4
FEATURE                 Location/Qualifiers
REGION                  1..4
                        note = Protease recognition site
source                  1..4
                        mol_type = protein
                        organism = synthetic construct
SEQUENCE: 22
RKKR                                                                    4

SEQ ID NO: 23           moltype = AA   length = 4
FEATURE                 Location/Qualifiers
REGION                  1..4
                        note = Protease recognition site
source                  1..4
                        mol_type = protein
                        organism = synthetic construct
SEQUENCE: 23
KRRR                                                                    4

SEQ ID NO: 24           moltype = AA   length = 4
FEATURE                 Location/Qualifiers
REGION                  1..4
                        note = Protease recognition site
source                  1..4
                        mol_type = protein
                        organism = synthetic construct
SEQUENCE: 24
KKRR                                                                    4

SEQ ID NO: 25           moltype = AA   length = 4
FEATURE                 Location/Qualifiers
REGION                  1..4
                        note = Protease recognition site
source                  1..4
                        mol_type = protein
                        organism = synthetic construct
SEQUENCE: 25
KRKR                                                                    4
```

```
SEQ ID NO: 26        moltype = AA   length = 4
FEATURE              Location/Qualifiers
REGION               1..4
                     note = Protease recognition site
source               1..4
                     mol_type = protein
                     organism = synthetic construct
SEQUENCE: 26
KKKR                                                                    4

SEQ ID NO: 27        moltype =   length =
SEQUENCE: 27
000

SEQ ID NO: 28        moltype =   length =
SEQUENCE: 28
000

SEQ ID NO: 29        moltype =   length =
SEQUENCE: 29
000

SEQ ID NO: 30        moltype =   length =
SEQUENCE: 30
000

SEQ ID NO: 31        moltype = AA   length = 5
FEATURE              Location/Qualifiers
REGION               1..5
                     note = Protease recognition site
source               1..5
                     mol_type = protein
                     organism = synthetic construct
SEQUENCE: 31
DDDDK                                                                   5

SEQ ID NO: 32        moltype =   length =
SEQUENCE: 32
000

SEQ ID NO: 33        moltype =   length =
SEQUENCE: 33
000

SEQ ID NO: 34        moltype = AA   length = 4
FEATURE              Location/Qualifiers
REGION               1..4
                     note = Protease recognition site
source               1..4
                     mol_type = protein
                     organism = synthetic construct
SEQUENCE: 34
DEVD                                                                    4

SEQ ID NO: 35        moltype =   length =
SEQUENCE: 35
000

SEQ ID NO: 36        moltype =   length =
SEQUENCE: 36
000

SEQ ID NO: 37        moltype =   length =
SEQUENCE: 37
000

SEQ ID NO: 38        moltype =   length =
SEQUENCE: 38
000

SEQ ID NO: 39        moltype =   length =
SEQUENCE: 39
000

SEQ ID NO: 40        moltype =   length =
SEQUENCE: 40
000
```

```
SEQ ID NO: 41          moltype =    length =
SEQUENCE: 41
000

SEQ ID NO: 42          moltype =    length =
SEQUENCE: 42
000

SEQ ID NO: 43          moltype =    length =
SEQUENCE: 43
000

SEQ ID NO: 44          moltype = AA  length = 4
FEATURE                Location/Qualifiers
REGION                 1..4
                       note = Protease recognition site
source                 1..4
                       mol_type = protein
                       organism = synthetic construct
SEQUENCE: 44
IEGR                                                                    4

SEQ ID NO: 45          moltype = AA  length = 4
FEATURE                Location/Qualifiers
REGION                 1..4
                       note = Protease recognition site
source                 1..4
                       mol_type = protein
                       organism = synthetic construct
SEQUENCE: 45
IDGR                                                                    4

SEQ ID NO: 46          moltype =    length =
SEQUENCE: 46
000

SEQ ID NO: 47          moltype =    length =
SEQUENCE: 47
000

SEQ ID NO: 48          moltype = AA  length = 4
FEATURE                Location/Qualifiers
REGION                 1..4
                       note = NTCB cleavage sequence
source                 1..4
                       mol_type = protein
                       organism = synthetic construct
SEQUENCE: 48
CGDE                                                                    4

SEQ ID NO: 49          moltype =    length =
SEQUENCE: 49
000

SEQ ID NO: 50          moltype =    length =
SEQUENCE: 50
000

SEQ ID NO: 51          moltype =    length =
SEQUENCE: 51
000

SEQ ID NO: 52          moltype =    length =
SEQUENCE: 52
000

SEQ ID NO: 53          moltype =    length =
SEQUENCE: 53
000

SEQ ID NO: 54          moltype =    length =
SEQUENCE: 54
000

SEQ ID NO: 55          moltype =    length =
SEQUENCE: 55
000
```

| | |
|---|---|
| SEQ ID NO: 56<br>FEATURE<br>REGION<br><br>source | moltype = AA  length = 4<br>Location/Qualifiers<br>1..4<br>note = Ni2+ cleavage sequence<br>1..4<br>mol_type = protein<br>organism = synthetic construct |
| SEQUENCE: 56<br>SRHW | 4 |
| SEQ ID NO: 57<br>SEQUENCE: 57<br>000 | moltype =   length = |
| SEQ ID NO: 58<br>SEQUENCE: 58<br>000 | moltype =   length = |
| SEQ ID NO: 59<br>SEQUENCE: 59<br>000 | moltype =   length = |
| SEQ ID NO: 60<br>SEQUENCE: 60<br>000 | moltype =   length = |
| SEQ ID NO: 61<br>SEQUENCE: 61<br>000 | moltype =   length = |
| SEQ ID NO: 62<br>SEQUENCE: 62<br>000 | moltype =   length = |
| SEQ ID NO: 63<br>SEQUENCE: 63<br>000 | moltype =   length = |
| SEQ ID NO: 64<br>SEQUENCE: 64<br>000 | moltype =   length = |
| SEQ ID NO: 65<br>SEQUENCE: 65<br>000 | moltype =   length = |
| SEQ ID NO: 66<br>SEQUENCE: 66<br>000 | moltype =   length = |
| SEQ ID NO: 67<br>FEATURE<br>REGION<br><br>source | moltype = AA  length = 5<br>Location/Qualifiers<br>1..5<br>note = Linker sequence<br>1..5<br>mol_type = protein<br>organism = synthetic construct |
| SEQUENCE: 67<br>GGGGS | 5 |
| SEQ ID NO: 68<br>SEQUENCE: 68<br>000 | moltype =   length = |
| SEQ ID NO: 69<br>SEQUENCE: 69<br>000 | moltype =   length = |
| SEQ ID NO: 70<br>SEQUENCE: 70<br>000 | moltype =   length = |
| SEQ ID NO: 71<br>SEQUENCE: 71<br>000 | moltype =   length = |
| SEQ ID NO: 72<br>SEQUENCE: 72<br>000 | moltype =   length = |

```
SEQ ID NO: 73          moltype =   length =
SEQUENCE: 73
000

SEQ ID NO: 74          moltype = AA   length = 7
FEATURE                Location/Qualifiers
REGION                 1..7
                       note = Linker sequence
source                 1..7
                       mol_type = protein
                       organism = synthetic construct
SEQUENCE: 74
GHHHHHH                                                                 7

SEQ ID NO: 75          moltype = AA   length = 6
FEATURE                Location/Qualifiers
REGION                 1..6
                       note = Linker sequence
source                 1..6
                       mol_type = protein
                       organism = synthetic construct
SEQUENCE: 75
EAAAKA                                                                  6

SEQ ID NO: 76          moltype = AA   length = 6
FEATURE                Location/Qualifiers
REGION                 1..6
                       note = Linker sequence
source                 1..6
                       mol_type = protein
                       organism = synthetic construct
SEQUENCE: 76
AEAAAK                                                                  6

SEQ ID NO: 77          moltype = AA   length = 18
FEATURE                Location/Qualifiers
REGION                 1..18
                       note = Linker sequence
source                 1..18
                       mol_type = protein
                       organism = synthetic construct
SEQUENCE: 77
KESGSVSSEQ LAQFRSLD                                                    18

SEQ ID NO: 78          moltype = AA   length = 14
FEATURE                Location/Qualifiers
REGION                 1..14
                       note = Linker sequence
source                 1..14
                       mol_type = protein
                       organism = synthetic construct
SEQUENCE: 78
EGKSSGSGSE SKST                                                        14

SEQ ID NO: 79          moltype = AA   length = 12
FEATURE                Location/Qualifiers
REGION                 1..12
                       note = Linker sequence
VARIANT                12
                       note = Xaa is Phe or Gly
source                 1..12
                       mol_type = protein
                       organism = synthetic construct
SEQUENCE: 79
GSAGSAAGSG EX                                                          12

SEQ ID NO: 80          moltype = AA   length = 12
FEATURE                Location/Qualifiers
REGION                 1..12
                       note = Linker sequence
source                 1..12
                       mol_type = protein
                       organism = synthetic construct
```

```
SEQUENCE: 80
GSAGSAAGSG EF                                                           12

SEQ ID NO: 81           moltype = AA   length = 12
FEATURE                 Location/Qualifiers
REGION                  1..12
                        note = Linker sequence
source                  1..12
                        mol_type = protein
                        organism = synthetic construct
SEQUENCE: 81
GSAGSAAGSG EG                                                           12

SEQ ID NO: 82           moltype = AA   length = 31
FEATURE                 Location/Qualifiers
REGION                  1..31
                        note = Linker sequence
source                  1..31
                        mol_type = protein
                        organism = synthetic construct
SEQUENCE: 82
EAEDLQVGQV ELGGGPGAGS LQPLALEGSL Q                                      31

SEQ ID NO: 83           moltype = AA   length = 26
FEATURE                 Location/Qualifiers
REGION                  1..26
                        note = Linker sequence
source                  1..26
                        mol_type = protein
                        organism = synthetic construct
SEQUENCE: 83
GAGAGAMALW MRLLPLLALL ALWGPD                                            26

SEQ ID NO: 84           moltype = AA   length = 29
FEATURE                 Location/Qualifiers
REGION                  1..29
                        note = Glucagon peptide
source                  1..29
                        mol_type = protein
                        organism = synthetic construct
SEQUENCE: 84
HSQGTFTSDY SKYLDSRRAQ DFVQWLMNT                                         29

SEQ ID NO: 85           moltype = AA   length = 39
FEATURE                 Location/Qualifiers
REGION                  1..39
                        note = Exenatide peptide
source                  1..39
                        mol_type = protein
                        organism = synthetic construct
SEQUENCE: 85
HGEGTFTSDL SKQMEEEAVR LFIEWLKNGG PSSGAPPPS                               39

SEQ ID NO: 86           moltype = AA   length = 30
FEATURE                 Location/Qualifiers
REGION                  1..30
                        note = Sermorelin peptide
source                  1..30
                        mol_type = protein
                        organism = synthetic construct
SEQUENCE: 86
YADAIFTNSY RKVLGQLSAR KLLQDIMSRQ                                        30

SEQ ID NO: 87           moltype = AA   length = 32
FEATURE                 Location/Qualifiers
REGION                  1..32
                        note = Nesiritide peptide
source                  1..32
                        mol_type = protein
                        organism = synthetic construct
SEQUENCE: 87
SPKMVQGSGC FGRKMDRISS SSGLGCKVLR RH                                     32
```

```
SEQ ID NO: 88            moltype = AA   length = 33
FEATURE                  Location/Qualifiers
REGION                   1..33
                         note = Teduglutide peptide
source                   1..33
                         mol_type = protein
                         organism = synthetic construct
SEQUENCE: 88
HGDGSFSDEM NTILDNLAAR DFINWLIQTK ITD                                   33

SEQ ID NO: 89            moltype = AA   length = 12
FEATURE                  Location/Qualifiers
REGION                   1..12
                         note = [Cys(Acm)20,31] Epidermal Growth Factor peptide
source                   1..12
                         mol_type = protein
                         organism = synthetic construct
SEQUENCE: 89
CMHIESLDSY TC                                                         12

SEQ ID NO: 90            moltype = AA   length = 12
FEATURE                  Location/Qualifiers
REGION                   1..12
                         note = T1 peptide
source                   1..12
                         mol_type = protein
                         organism = synthetic construct
SEQUENCE: 90
MSRPACPNRK YG                                                         12

SEQ ID NO: 91            moltype = AA   length = 16
FEATURE                  Location/Qualifiers
REGION                   1..16
                         note = GTP-binding Protein Fragment, Galpha
source                   1..16
                         mol_type = protein
                         organism = synthetic construct
SEQUENCE: 91
CGAGESGKST IVKQMK                                                     16

SEQ ID NO: 92            moltype = AA   length = 12
FEATURE                  Location/Qualifiers
REGION                   1..12
                         note = L-selectin peptide
source                   1..12
                         mol_type = protein
                         organism = synthetic construct
SEQUENCE: 92
CQKLDKSFSM IK                                                         12

SEQ ID NO: 93            moltype = AA   length = 18
FEATURE                  Location/Qualifiers
REGION                   1..18
                         note = Peptide Standard 1
source                   1..18
                         mol_type = protein
                         organism = synthetic construct
SEQUENCE: 93
CPDFGHIAME LSVRTWKY                                                   18

SEQ ID NO: 94            moltype = AA   length = 39
FEATURE                  Location/Qualifiers
REGION                   1..39
                         note = ACTH (1-39) (Acthar)
source                   1..39
                         mol_type = protein
                         organism = synthetic construct
SEQUENCE: 94
SYSMEHFRWG KPVGKKRRPV KVYPDGAEDQ LAEAFPLEF                             39

SEQ ID NO: 95            moltype = AA   length = 24
FEATURE                  Location/Qualifiers
REGION                   1..24
                         note = ACTH (1-24)
source                   1..24
                         mol_type = protein
                         organism = synthetic construct
```

```
SEQUENCE: 95
SYSMEHFRWG KPVGKKRRPV KVYP                                          24

SEQ ID NO: 96           moltype = AA  length = 65
FEATURE                 Location/Qualifiers
REGION                  1..65
                        note = Lepirudin
source                  1..65
                        mol_type = protein
                        organism = synthetic construct
SEQUENCE: 96
LVYTDCTESG QNLCLCEGSN VCGQGNKCIL GSDGEKNQCV TGEGTPKPQS HNDGDFEEIP   60
EEYLQ                                                               65

SEQ ID NO: 97           moltype = AA  length = 32
FEATURE                 Location/Qualifiers
REGION                  1..32
                        note = Calcitonin
source                  1..32
                        mol_type = protein
                        organism = synthetic construct
SEQUENCE: 97
CSNLSTCVLG KLSQELHKLQ TYPRTNTGSG TP                                 32

SEQ ID NO: 98           moltype = AA  length = 14
FEATURE                 Location/Qualifiers
REGION                  1..14
                        note = Somatostatin
source                  1..14
                        mol_type = protein
                        organism = synthetic construct
SEQUENCE: 98
AGCKNFFWKT FTSC                                                     14

SEQ ID NO: 99           moltype = AA  length = 23
FEATURE                 Location/Qualifiers
REGION                  1..23
                        note = Megainin 1
source                  1..23
                        mol_type = protein
                        organism = synthetic construct
SEQUENCE: 99
GIGKFLHSAG KFGKAFVGEI MKS                                           23

SEQ ID NO: 100          moltype = AA  length = 23
FEATURE                 Location/Qualifiers
REGION                  1..23
                        note = Megainin 2
source                  1..23
                        mol_type = protein
                        organism = synthetic construct
SEQUENCE: 100
GIGKFLHSAK KFGKAFVGEI MNS                                           23

SEQ ID NO: 101          moltype = AA  length = 39
FEATURE                 Location/Qualifiers
REGION                  1..39
                        note = Corticotropin
source                  1..39
                        mol_type = protein
                        organism = synthetic construct
SEQUENCE: 101
SYSMEHFRWG KPVGKKRRPV KVYPDGAEDQ LAEAFPLEF                          39

SEQ ID NO: 102          moltype = AA  length = 34
FEATURE                 Location/Qualifiers
REGION                  1..34
                        note = Teriparatide
source                  1..34
                        mol_type = protein
                        organism = synthetic construct
```

-continued

```
SEQUENCE: 102
SVSEIQLMHN LGKHLNSMER VEWLRKKLQD VHNF                              34

SEQ ID NO: 103          moltype = AA   length = 44
FEATURE                 Location/Qualifiers
REGION                  1..44
                        note = Tesamorelin
source                  1..44
                        mol_type = protein
                        organism = synthetic construct
SEQUENCE: 103
YADAIFTNSY RKVLGQLSAR KLLQDIMSRQ QGESNQERGA RARL                   44

SEQ ID NO: 104          moltype = AA   length = 58
FEATURE                 Location/Qualifiers
REGION                  1..58
                        note = Aprotinin
source                  1..58
                        mol_type = protein
                        organism = synthetic construct
SEQUENCE: 104
RPDFCLEPPY TGPCKARIIR YFYNAKAGLC QTFVYGGCRA KRNNFKSAED CMRTCGGA    58

SEQ ID NO: 105          moltype = AA   length = 9
FEATURE                 Location/Qualifiers
REGION                  1..9
                        note = Vasopressin
source                  1..9
                        mol_type = protein
                        organism = synthetic construct
SEQUENCE: 105
CYFQNCPRG                                                          9

SEQ ID NO: 106          moltype = AA   length = 9
FEATURE                 Location/Qualifiers
REGION                  1..9
                        note = Oxytocin
source                  1..9
                        mol_type = protein
                        organism = synthetic construct
SEQUENCE: 106
CYIQNCPLG                                                          9

SEQ ID NO: 107          moltype = AA   length = 21
FEATURE                 Location/Qualifiers
REGION                  1..21
                        note = Insulin Chain A
source                  1..21
                        mol_type = protein
                        organism = synthetic construct
SEQUENCE: 107
GIVEQCCTSI CSLYQLENYC N                                            21

SEQ ID NO: 108          moltype = AA   length = 30
FEATURE                 Location/Qualifiers
REGION                  1..30
                        note = Insulin Chain B
source                  1..30
                        mol_type = protein
                        organism = synthetic construct
SEQUENCE: 108
FVNQHLCGSH LVEALYLVCG ERGFFYTPKT                                   30

SEQ ID NO: 109          moltype = AA   length = 37
FEATURE                 Location/Qualifiers
REGION                  1..37
                        note = Pramlinitide
source                  1..37
                        mol_type = protein
                        organism = synthetic construct
SEQUENCE: 109
KCNTATCATQ RLANFLVHSS NNFGPILPPT NVGSNTY                           37
```

```
SEQ ID NO: 110          moltype = AA  length = 32
FEATURE                 Location/Qualifiers
REGION                  1..32
                        note = Liraglutide
source                  1..32
                        mol_type = protein
                        organism = synthetic construct
SEQUENCE: 110
HAEGTFTSDV SSYLEGQAAK EEFIAWLVRG RG                                   32

SEQ ID NO: 111          moltype = AA  length = 23
FEATURE                 Location/Qualifiers
REGION                  1..23
                        note = ACE2 alpha1 Helix peptide
source                  1..23
                        mol_type = protein
                        organism = synthetic construct
SEQUENCE: 111
IEEQAKTFLD KFNHEAEDLF YQS                                             23

SEQ ID NO: 112          moltype = AA  length = 20
FEATURE                 Location/Qualifiers
REGION                  1..20
                        note = Sinapultide
source                  1..20
                        mol_type = protein
                        organism = synthetic construct
SEQUENCE: 112
KLLLLKLLLL KLLLLKLLLL                                                 20

SEQ ID NO: 113          moltype = AA  length = 28
FEATURE                 Location/Qualifiers
REGION                  1..28
                        note = Thymalfasin
source                  1..28
                        mol_type = protein
                        organism = synthetic construct
SEQUENCE: 113
SDAAVDTSSE ITTKDLKEKK EVVEEAEN                                        28

SEQ ID NO: 114          moltype = AA  length = 21
FEATURE                 Location/Qualifiers
REGION                  1..21
                        note = Apolipoprotein B synthetic peptide
source                  1..21
                        mol_type = protein
                        organism = synthetic construct
SEQUENCE: 114
KYYELEEKIV SLIKNLLVAL K                                               21

SEQ ID NO: 115          moltype = AA  length = 30
FEATURE                 Location/Qualifiers
REGION                  1..30
                        note = Galanin
source                  1..30
                        mol_type = protein
                        organism = synthetic construct
SEQUENCE: 115
GWTLNSAGYL LGPHAVGNHR SFSDKNGLTS                                      30

SEQ ID NO: 116          moltype = AA  length = 29
FEATURE                 Location/Qualifiers
REGION                  1..29
                        note = Tau Peptide (45-73) (Exon 2/Insert 1 domain)
source                  1..29
                        mol_type = protein
                        organism = synthetic construct
SEQUENCE: 116
ESPLQTPTED GSEEPGSETS DAKSTPTAE                                       29

SEQ ID NO: 117          moltype = AA  length = 20
FEATURE                 Location/Qualifiers
REGION                  1..20
                        note = Bivalirudin
source                  1..20
                        mol_type = protein
                        organism = synthetic construct
```

```
SEQUENCE: 117
FPRPGGGNG DFEEIPEEYL                                                  20

SEQ ID NO: 118           moltype = AA   length = 36
FEATURE                  Location/Qualifiers
REGION                   1..36
                         note = Enfuviritide
source                   1..36
                         mol_type = protein
                         organism = synthetic construct
SEQUENCE: 118
YTSLIHSLIE ESQNQQEKNE QELLELDKWA SLWNWF                                36

SEQ ID NO: 119           moltype = AA   length = 27
FEATURE                  Location/Qualifiers
REGION                   1..27
                         note = Secretin
source                   1..27
                         mol_type = protein
                         organism = synthetic construct
SEQUENCE: 119
HSDGTFTSEL SRLRDSARLQ RLLQGLV                                         27

SEQ ID NO: 120           moltype = AA   length = 16
FEATURE                  Location/Qualifiers
REGION                   1..16
                         note = Gramicidin D
SITE                     16
                         note = misc_feature - Xaa can be any naturally occurring
                          amino acid
source                   1..16
                         mol_type = protein
                         organism = synthetic construct
SEQUENCE: 120
VGALAVVVWL WLWLWX                                                     16

SEQ ID NO: 121           moltype = AA   length = 52
FEATURE                  Location/Qualifiers
REGION                   1..52
                         note = Glatiramer
source                   1..52
                         mol_type = protein
                         organism = synthetic construct
SEQUENCE: 121
EAYKAAEKAY AAKEAAKEAA KAKAEKKAAY AKAKAAKYEK KAKKAAAEYK KK              52

SEQ ID NO: 122           moltype = AA   length = 127
FEATURE                  Location/Qualifiers
REGION                   1..127
                         note = Thioredoxin tag
source                   1..127
                         mol_type = protein
                         organism = synthetic construct
SEQUENCE: 122
MIAPILDEIA DEYQGKLTVA KLNIDQNPGT APKYGIRGIP TLLLFKNGEV AATKVGALSK      60
GQLKEFLDAN LAGSGSGHMH HHHHSSGLVP RGSGMKETAA AKFERQHMDS PDLGTDDDDK     120
AMADIGS                                                              127

SEQ ID NO: 123           moltype = AA   length = 6
FEATURE                  Location/Qualifiers
REGION                   1..6
                         note = His6 tag
source                   1..6
                         mol_type = protein
                         organism = synthetic construct
SEQUENCE: 123
HHHHHH                                                                 6

SEQ ID NO: 124           moltype = AA   length = 26
FEATURE                  Location/Qualifiers
REGION                   1..26
                         note = His tag
source                   1..26
                         mol_type = protein
                         organism = synthetic construct
SEQUENCE: 124
MHHHHHHALW MRLLPLLALL ALWGPD                                          26
```

```
SEQ ID NO: 125          moltype = AA   length = 134
FEATURE                 Location/Qualifiers
REGION                  1..134
                        note = Recombinant polypeptide
source                  1..134
                        mol_type = protein
                        organism = synthetic construct
SEQUENCE: 125
HSQGTFTSDY SKYLDSRRAQ DFVQWLMNTC GDEVDHSQGT FTSDYSKYLD SRRAQDFVQW    60
LMNTCGDEVD HSQGTFTSDY SKYLDSRRAQ DFVQWLMNTC GDEVDHSQGT FTSDYSKYLD   120
SRRAQDFVQW LMNT                                                    134

SEQ ID NO: 126          moltype = AA   length = 266
FEATURE                 Location/Qualifiers
REGION                  1..266
                        note = Recombinant polypeptide
source                  1..266
                        mol_type = protein
                        organism = synthetic construct
SEQUENCE: 126
MIAPILDEIA DEYQGKLTVA KLNIDQNPGT APKYGIRGIP TLLLFKNGEV AATKVGALSK    60
GQLKEFLDAN LAGSGSGHMH HHHHSSGLVP RGSGMKETAA AKFERQHMDS PDLGTDDDDK   120
AMADIGSGDE VDHSQGTFTS DYSKYLDSRR AQDFVQWLMN TCGDEVDHSQ GTFTSDYSKY   180
LDSRRAQDFV QWLMNTCGDE VDHSQGTFTS DYSKYLDSRR AQDFVQWLMN TCGDEVDHSQ   240
GTFTSDYSKY LDSRRAQDFV QWLMNT                                       266

SEQ ID NO: 127          moltype = AA   length = 5
FEATURE                 Location/Qualifiers
REGION                  1..5
                        note = Peptide comprising linker and protease recognition
                         site
source                  1..5
                        mol_type = protein
                        organism = synthetic construct
SEQUENCE: 127
GDEVD                                                                5

SEQ ID NO: 128          moltype = AA   length = 6
FEATURE                 Location/Qualifiers
REGION                  1..6
                        note = Peptide comprising linker and protease recognition
                         site
source                  1..6
                        mol_type = protein
                        organism = synthetic construct
SEQUENCE: 128
CGDEVD                                                               6

SEQ ID NO: 129          moltype = AA   length = 140
FEATURE                 Location/Qualifiers
REGION                  1..140
                        note = Recombinant polypeptide
source                  1..140
                        mol_type = protein
                        organism = synthetic construct
SEQUENCE: 129
HSQGTFTSDY SKYLDSRRAQ DFVQWLMNTP HGGDEVDHSQ GTFTSDYSKY LDSRRAQDFV    60
QWLMNTPHGG DEVDHSQGTF TSDYSKYLDS RRAQDFVQWL MNTPHGGDEV DHSQGTFTSD   120
YSKYLDSRRA QDFVQWLMNT                                              140

SEQ ID NO: 130          moltype = AA   length = 272
FEATURE                 Location/Qualifiers
REGION                  1..272
                        note = Recombinant polypeptide
source                  1..272
                        mol_type = protein
                        organism = synthetic construct
SEQUENCE: 130
MIAPILDEIA DEYQGKLTVA KLNIDQNPGT APKYGIRGIP TLLLFKNGEV AATKVGALSK    60
GQLKEFLDAN LAGSGSGHMH HHHHSSGLVP RGSGMKETAA AKFERQHMDS PDLGTDDDDK   120
AMADIGSGDE VDHSQGTFTS DYSKYLDSRR AQDFVQWLMN TPHGGDEVDH SQGTFTSDYS   180
KYLDSRRAQD FVQWLMNTPH GGDEVDHSQG TFTSDYSKYL DSRRAQDFVQ WLMNTPHGGD   240
EVDHSQGTFT SDYSKYLDSR RAQDFVQWLM NT                                272
```

```
SEQ ID NO: 131            moltype = AA   length = 8
FEATURE                   Location/Qualifiers
REGION                    1..8
                          note = Peptide comprising linker and chemical cleavage site
source                    1..8
                          mol_type = protein
                          organism = synthetic construct
SEQUENCE: 131
PHGGDEVD                                                                    8

SEQ ID NO: 132            moltype = AA   length = 143
FEATURE                   Location/Qualifiers
REGION                    1..143
                          note = Recombinant polypeptide
source                    1..143
                          mol_type = protein
                          organism = synthetic construct
SEQUENCE: 132
HSQGTFTSDY SKYLDSRRAQ DFVQWLMNTS RHWGDEVDHS QGTFTSDYSK YLDSRRAQDF           60
VQWLMNTSRH WGDEVDHSQG TFTSDYSKYL DSRRAQDFVQ WLMNTSRHWG DEVDHSQGTF          120
TSDYSKYLDS RRAQDFVQWL MNT                                                 143

SEQ ID NO: 133            moltype = AA   length = 275
FEATURE                   Location/Qualifiers
REGION                    1..275
                          note = Recombinant polypeptide
source                    1..275
                          mol_type = protein
                          organism = synthetic construct
SEQUENCE: 133
MIAPILDEIA DEYQGKLTVA KLNIDQNPGT APKYGIRGIP TLLLFKNGEV AATKVGALSK           60
GQLKEFLDAN LAGSGSGHMH HHHHSSGLVP RGSGMKETAA AKFERQHMDS PDLGTDDDDK          120
AMADIGSGDE VDHSQGTFTS DYSKYLDSRR AQDFVQWLMN TSRHWGDEVD HSQGTFTSDY          180
SKYLDSRRAQ DFVQWLMNTS RHWGDEVDHS QGTFTSDYSK YLDSRRAQDF VQWLMNTSRH          240
WGDEVDHSQG TFTSDYSKYL DSRRAQDFVQ WLMNT                                    275

SEQ ID NO: 134            moltype = AA   length = 9
FEATURE                   Location/Qualifiers
REGION                    1..9
                          note = Peptide comprising linker and chemical cleavage site
source                    1..9
                          mol_type = protein
                          organism = synthetic construct
SEQUENCE: 134
SRHWGDEVD                                                                   9

SEQ ID NO: 135            moltype = AA   length = 146
FEATURE                   Location/Qualifiers
REGION                    1..146
                          note = Recombinant polypeptide
source                    1..146
                          mol_type = protein
                          organism = synthetic construct
SEQUENCE: 135
HAEGTFTSDV SSYLEGQAAK EEFIAWLVRG RGRRGSKRHA EGTFTSDVSS YLEGQAAKEE           60
FIAWLVRGRG RRGSRRHAEG TFTSDVSSYL EGQAAKEEFI AWLVRGRGRR GSKRHAEGTF          120
TSDVSSYLEG QAAKEEFIAW LVRGRG                                              146

SEQ ID NO: 136            moltype = AA   length = 276
FEATURE                   Location/Qualifiers
REGION                    1..276
                          note = Recombinant polypeptide
source                    1..276
                          mol_type = protein
                          organism = synthetic construct
SEQUENCE: 136
MIAPILDEIA DEYQGKLTVA KLNIDQNPGT APKYGIRGIP TLLLFKNGEV AATKVGALSK           60
GQLKEFLDAN LAGSGSGHMH HHHHSSGLVP RGSGMKETAA AKFERQHMDS PDLGTDDDDK          120
AMADIGSGRR HAEGTFTSDV SSYLEGQAAK EEFIAWLVRG RGRRGSKRHA EGTFTSDVSS          180
YLEGQAAKEE FIAWLVRGRG RRGSRRHAEG TFTSDVSSYL EGQAAKEEFI AWLVRGRGRR          240
GSKRHAEGTF TSDVSSYLEG QAAKEEFIAW LVRGRG                                   276
```

```
SEQ ID NO: 137          moltype = AA   length = 6
FEATURE                 Location/Qualifiers
REGION                  1..6
                        note = Peptide comprising linker and protease recognition
                         site
source                  1..6
                        mol_type = protein
                        organism = synthetic construct
SEQUENCE: 137
RRGSKR                                                                       6

SEQ ID NO: 138          moltype = AA   length = 152
FEATURE                 Location/Qualifiers
REGION                  1..152
                        note = Recombinant polypeptide
source                  1..152
                        mol_type = protein
                        organism = synthetic construct
SEQUENCE: 138
HAEGTFTSDV SSYLEGQAAK EEFIAWLVRG RGPHGGDEVD HAEGTFTSDV SSYLEGQAAK            60
EEFIAWLVRG RGPHGGDEVD HAEGTFTSDV SSYLEGQAAK EEFIAWLVRG RGPHGGDEVD           120
HAEGTFTSDV SSYLEGQAAK EEFIAWLVRG RG                                         152

SEQ ID NO: 139          moltype = AA   length = 284
FEATURE                 Location/Qualifiers
REGION                  1..284
                        note = Recombinant polypeptide
source                  1..284
                        mol_type = protein
                        organism = synthetic construct
SEQUENCE: 139
MIAPILDEIA DEYQGKLTVA KLNIDQNPGT APKYGIRGIP TLLLFKNGEV AATKVGALSK            60
GQLKEFLDAN LAGSGSGHMH HHHSSGLVP RGSGMKETAA AKFERQHMDS PDLGTDDDDK            120
AMADIGSGDE VDHAEGTFTS DVSSYLEGQA AKEEFIAWLV RGRGPHGGDE VDHAEGTFTS           180
DVSSYLEGQA AKEEFIAWLV RGRGPHGGDE VDHAEGTFTS DVSSYLEGQA AKEEFIAWLV           240
RGRGPHGGDE VDHAEGTFTS DVSSYLEGQA AKEEFIAWLV RGRG                            284

SEQ ID NO: 140          moltype = AA   length = 40
FEATURE                 Location/Qualifiers
REGION                  1..40
                        note = Intermediate peptide
source                  1..40
                        mol_type = protein
                        organism = synthetic construct
SEQUENCE: 140
HAEGTFTSDV SSYLEGQAAK EEFIAWLVRG RGPHGGDEVD                                  40

SEQ ID NO: 141          moltype = AA   length = 129
FEATURE                 Location/Qualifiers
REGION                  1..129
                        note = Recombinant polypeptide
source                  1..129
                        mol_type = protein
                        organism = synthetic construct
SEQUENCE: 141
FVNQHLCGSH LVEALYLVCG ERGFFYTPKT SRHWGDEVDF VNQHLCGSHL VEALYLVCGE            60
RGFFYTPKTS RHWGDEVDGI VEQCCTSICS LYQLENYCNS RHWGDEVDGI VEQCCTSICS           120
LYQLENYCN                                                                   129

SEQ ID NO: 142          moltype = AA   length = 120
FEATURE                 Location/Qualifiers
REGION                  1..120
                        note = Recombinant polypeptide
source                  1..120
                        mol_type = protein
                        organism = synthetic construct
SEQUENCE: 142
FVNQHLCGSH LVEALYLVCG ERGFFYTPKT RRGSKRFVNQ HLCGSHLVEA LYLVCGERGF            60
FYTPKTRRGS RRGIVEQCCT SICSLYQLEN YCNRRGSKRG IVEQCCTSIC SLYQLENYCN           120

SEQ ID NO: 143          moltype = AA   length = 32
FEATURE                 Location/Qualifiers
REGION                  1..32
                        note = Intermediate peptide
source                  1..32
                        mol_type = protein
                        organism = synthetic construct
```

```
SEQUENCE: 143
FVNQHLCGSH LVEALYLVCG ERGFFYTPKT RR                                      32

SEQ ID NO: 144           moltype = AA  length = 23
FEATURE                  Location/Qualifiers
REGION                   1..23
                         note = Intermediate peptide
source                   1..23
                         mol_type = protein
                         organism = synthetic construct
SEQUENCE: 144
GIVEQCCTSI CSLYQLENYC NRR                                                23

SEQ ID NO: 145           moltype = AA  length = 154
FEATURE                  Location/Qualifiers
REGION                   1..154
                         note = Recombinant polypeptide
source                   1..154
                         mol_type = protein
                         organism = synthetic construct
SEQUENCE: 145
GDEVDHAEGT FTSDVSSYLE GQAAKEEFIA WLVRGRGPGG DEVDHAEGTF TSDVSSYLEG         60
QAAKEEFIAW LVRGRGPGGD EVDHAEGTFT SDVSSYLEGQ AAKEEFIAWL VRGRGPGGDE        120
VDHAEGTFTS DVSSYLEGQA AKEEFIAWLV RGRG                                   154

SEQ ID NO: 146           moltype = AA  length = 7
FEATURE                  Location/Qualifiers
REGION                   1..7
                         note = Peptide comprising linker and protease recognition
                          site
source                   1..7
                         mol_type = protein
                         organism = synthetic construct
SEQUENCE: 146
PGGDEVD                                                                   7

SEQ ID NO: 147           moltype = AA  length = 39
FEATURE                  Location/Qualifiers
REGION                   1..39
                         note = Intermediate peptide
source                   1..39
                         mol_type = protein
                         organism = synthetic construct
SEQUENCE: 147
HAEGTFTSDV SSYLEGQAAK EEFIAWLVRG RGPGGDEVD                                39

SEQ ID NO: 148           moltype = AA  length = 145
FEATURE                  Location/Qualifiers
REGION                   1..145
                         note = Recombinant polypeptide
source                   1..145
                         mol_type = protein
                         organism = synthetic construct
SEQUENCE: 148
RRHAEGTFTS DVSSYLEGQA AKEEFIAWLV RGRGPGGRRH AEGTFTSDVS SYLEGQAAKE         60
EFIAWLVRGR GPGGKRHAEG TFTSDVSSYL EGQAAKEEFI AWLVRGRGPG GRRHAEGTFT        120
SDVSSYLEGQ AAKEEFIAWL VRGRG                                             145

SEQ ID NO: 149           moltype = AA  length = 5
FEATURE                  Location/Qualifiers
REGION                   1..5
                         note = Peptide comprising linker and protease recognition
                          site
source                   1..5
                         mol_type = protein
                         organism = synthetic construct
SEQUENCE: 149
PGGRR                                                                     5

SEQ ID NO: 150           moltype = AA  length = 5
FEATURE                  Location/Qualifiers
REGION                   1..5
                         note = Peptide comprising linker and protease recognition
                          site
source                   1..5
                         mol_type = protein
                         organism = synthetic construct
```

```
SEQUENCE: 150
PGGKR                                                                           5

SEQ ID NO: 151           moltype = AA   length = 37
FEATURE                  Location/Qualifiers
REGION                   1..37
                         note = Intermediate peptide
source                   1..37
                         mol_type = protein
                         organism = synthetic construct
SEQUENCE: 151
HAEGTFTSDV SSYLEGQAAK EEFIAWLVRG RGPGGKR                                         37

SEQ ID NO: 152           moltype = AA   length = 37
FEATURE                  Location/Qualifiers
REGION                   1..37
                         note = Intermediate peptide
source                   1..37
                         mol_type = protein
                         organism = synthetic construct
SEQUENCE: 152
HAEGTFTSDV SSYLEGQAAK EEFIAWLVRG RGPGGRR                                         37

SEQ ID NO: 153           moltype = AA   length = 157
FEATURE                  Location/Qualifiers
REGION                   1..157
                         note = Recombinant polypeptide
source                   1..157
                         mol_type = protein
                         organism = synthetic construct
SEQUENCE: 153
DDDDKHAEGT FTSDVSSYLE GQAAKEEFIA WLVRGRGPGG DDDDKHAEGT FTSDVSSYLE                60
GQAAKEEFIA WLVRGRGPGG DDDDKHAEGT FTSDVSSYLE GQAAKEEFIA WLVRGRGPGG               120
DDDDKHAEGT FTSDVSSYLE GQAAKEEFIA WLVRGRG                                       157

SEQ ID NO: 154           moltype = AA   length = 8
FEATURE                  Location/Qualifiers
REGION                   1..8
                         note = Peptide comprising linker and protease recognition
                          site
source                   1..8
                         mol_type = protein
                         organism = synthetic construct
SEQUENCE: 154
PGGDDDDK                                                                        8

SEQ ID NO: 155           moltype = AA   length = 40
FEATURE                  Location/Qualifiers
REGION                   1..40
                         note = Intermediate peptide
source                   1..40
                         mol_type = protein
                         organism = synthetic construct
SEQUENCE: 155
HAEGTFTSDV SSYLEGQAAK EEFIAWLVRG RGPGGDDDDK                                      40

SEQ ID NO: 156           moltype = AA   length = 234
FEATURE                  Location/Qualifiers
REGION                   1..234
                         note = Recombinant polypeptide
source                   1..234
                         mol_type = protein
                         organism = synthetic construct
SEQUENCE: 156
MHHHHHHALW MRLLPLLALL ALWGPDDEVD FVNQHLCGSH LVEALYLVCG ERGFFYTPKT                60
RREAEDLQVG QVELGGGPGA GSLQPLALEG SLQKRGIVEQ CCTSICSLYQ LENYCNRRGA               120
GAGAMALWMR LLPLLALLAL WGPDDEVDFV NQHLCGSHLV EALYLVCGER GFFYTPKTRR               180
EAEDLQVGQV ELGGGPGAGS LQPLALEGSL QKRGIVEQCC TSICSLYQLE NYCN                     234

SEQ ID NO: 157           moltype = AA   length = 352
FEATURE                  Location/Qualifiers
REGION                   1..352
                         note = Recombinant polypeptide
source                   1..352
                         mol_type = protein
                         organism = synthetic construct
```

```
SEQUENCE: 157
MHHHHHHALW MRLLPLLALL ALWGPDDEVD FVNQHLCGSH LVEALYLVCG ERGFFYTPKT    60
RREAEDLQVG QVELGGGPGA GSLQPLALEG SLQKRGIVEQ CCTSICSLYQ LENYCNRRGA   120
GAGAMALWMR LLPLLALLAL WGPDDEVDFV NQHLCGSHLV EALYLVCGER GFFYTPKTRR   180
EAEDLQVGQV ELGGGPGAGS LQPLALEGSL QKRGIVEQCC TSICSLYQLE NYCNRRGAGA   240
GAMALWMRLL PLLALLALWG PDDEVDFVNQ HLCGSHLVEA LYLVCGERGF FYTPKTRREA   300
EDLQVGQVEL GGGPGAGSLQ PLALEGSLQK RGIVEQCCTS ICSLYQLENY CN           352

SEQ ID NO: 158          moltype = AA   length = 470
FEATURE                 Location/Qualifiers
REGION                  1..470
                        note = Recombinant polypeptide
source                  1..470
                        mol_type = protein
                        organism = synthetic construct
SEQUENCE: 158
MHHHHHHALW MRLLPLLALL ALWGPDDEVD FVNQHLCGSH LVEALYLVCG ERGFFYTPKT    60
RREAEDLQVG QVELGGGPGA GSLQPLALEG SLQKRGIVEQ CCTSICSLYQ LENYCNRRGA   120
GAGAMALWMR LLPLLALLAL WGPDDEVDFV NQHLCGSHLV EALYLVCGER GFFYTPKTRR   180
EAEDLQVGQV ELGGGPGAGS LQPLALEGSL QKRGIVEQCC TSICSLYQLE NYCNRRGAGA   240
GAMALWMRLL PLLALLALWG PDDEVDFVNQ HLCGSHLVEA LYLVCGERGF FYTPKTRREA   300
EDLQVGQVEL GGGPGAGSLQ PLALEGSLQK RGIVEQCCTS ICSLYQLENY CNRRGAGAGA   360
MALWMRLLPL LALLALWGPD DEVDFVNQHL CGSHLVEALY LVCGERGFFY TPKTRREAED   420
LQVGQVELGG GPGAGSLQPL ALEGSLQKRG IVEQCCTSIC SLYQLENYCN              470

SEQ ID NO: 159          moltype = AA   length = 824
FEATURE                 Location/Qualifiers
REGION                  1..824
                        note = Recombinant polypeptide
source                  1..824
                        mol_type = protein
                        organism = synthetic construct
SEQUENCE: 159
MHHHHHHALW MRLLPLLALL ALWGPDDEVD FVNQHLCGSH LVEALYLVCG ERGFFYTPKT    60
RREAEDLQVG QVELGGGPGA GSLQPLALEG SLQKRGIVEQ CCTSICSLYQ LENYCNRRGA   120
GAGAMALWMR LLPLLALLAL WGPDDEVDFV NQHLCGSHLV EALYLVCGER GFFYTPKTRR   180
EAEDLQVGQV ELGGGPGAGS LQPLALEGSL QKRGIVEQCC TSICSLYQLE NYCNRRGAGA   240
GAMALWMRLL PLLALLALWG PDDEVDFVNQ HLCGSHLVEA LYLVCGERGF FYTPKTRREA   300
EDLQVGQVEL GGGPGAGSLQ PLALEGSLQK RGIVEQCCTS ICSLYQLENY CNRRGAGAGA   360
MALWMRLLPL LALLALWGPD DEVDFVNQHL CGSHLVEALY LVCGERGFFY TPKTRREAED   420
LQVGQVELGG GPGAGSLQPL ALEGSLQKRG IVEQCCTSIC SLYQLENYCN RRGAGAGAMA   480
LWMRLLPLLA LLALWGPDDE VDFVNQHLCG SHLVEALYLV CGERGFFYTP KTRREAEDLQ   540
VGQVELGGGP GAGSLQPLAL EGSLQKRGIV EQCCTSICSL YQLENYCNRR GAGAGAMALW   600
MRLLPLLALL ALWGPDDEVD FVNQHLCGSH LVEALYLVCG ERGFFYTPKT RREAEDLQVG   660
QVELGGGPGA GSLQPLALEG SLQKRGIVEQ CCTSICSLYQ LENYCNRRGA GAGAMALWMR   720
LLPLLALLAL WGPDDEVDFV NQHLCGSHLV EALYLVCGER GFFYTPKTRR EAEDLQVGQV   780
ELGGGPGAGS LQPLALEGSL QKRGIVEQCC TSICSLYQLE NYCN                    824

SEQ ID NO: 160          moltype = AA   length = 62
FEATURE                 Location/Qualifiers
REGION                  1..62
                        note = Intermediate peptide
source                  1..62
                        mol_type = protein
                        organism = synthetic construct
SEQUENCE: 160
MHHHHHHALW MRLLPLLALL ALWGPDDEVD FVNQHLCGSH LVEALYLVCG ERGFFYTPKT    60
RR                                                                   62

SEQ ID NO: 161          moltype = AA   length = 62
FEATURE                 Location/Qualifiers
REGION                  1..62
                        note = Intermediate peptide
source                  1..62
                        mol_type = protein
                        organism = synthetic construct
SEQUENCE: 161
GAGAGAMALW MRLLPLLALL ALWGPDDEVD FVNQHLCGSH LVEALYLVCG ERGFFYTPKT    60
RR                                                                   62

SEQ ID NO: 162          moltype = AA   length = 60
FEATURE                 Location/Qualifiers
REGION                  1..60
                        note = Intermediate peptide
source                  1..60
                        mol_type = protein
                        organism = synthetic construct
```

```
SEQUENCE: 162
MHHHHHHALW MRLLPLLALL ALWGPDDEVD FVNQHLCGSH LVEALYLVCG ERGFFYTPKT    60

SEQ ID NO: 163           moltype = AA  length = 60
FEATURE                  Location/Qualifiers
REGION                   1..60
                         note = Intermediate peptide
source                   1..60
                         mol_type = protein
                         organism = synthetic construct
SEQUENCE: 163
GAGAGAMALW MRLLPLLALL ALWGPDDEVD FVNQHLCGSH LVEALYLVCG ERGFFYTPKT    60

SEQ ID NO: 164           moltype = AA  length = 153
FEATURE                  Location/Qualifiers
REGION                   1..153
                         note = Recombinant polypeptide
source                   1..153
                         mol_type = protein
                         organism = synthetic construct
SEQUENCE: 164
GRRHHHHHHD EVDFVNQHLC GSHLVEALYL VCGERGFFYT PKTRRGHHHH HHDEVDFVNQ    60
HLCGSHLVEA LYLVCGERGF FYTPKTRRHH HHHHDEVDGI VEQCCTSICS LYQLENYCNR   120
RGHHHHHHDE VDGIVEQCCT SICSLYQLEN YCN                                153

SEQ ID NO: 165           moltype = AA  length = 153
FEATURE                  Location/Qualifiers
REGION                   1..153
                         note = Recombinant polypeptide
source                   1..153
                         mol_type = protein
                         organism = synthetic construct
SEQUENCE: 165
GRRHHHHHHD EVDGIVEQCC TSICSLYQLE NYCNRRGHHH HHHDEVDGIV EQCCTSICSL    60
YQLENYCNRR HHHHHHDEVD FVNQHLCGSH LVEALYLVCG ERGFFYTPKT RRGHHHHHHD   120
EVDFVNQHLC GSHLVEALYL VCGERGFFYT PKT                                153

SEQ ID NO: 166           moltype = AA  length = 43
FEATURE                  Location/Qualifiers
REGION                   1..43
                         note = Intermediate peptide
source                   1..43
                         mol_type = protein
                         organism = synthetic construct
SEQUENCE: 166
GHHHHHHDEV DFVNQHLCGS HLVEALYLVC GERGFFYTPK TRR                      43

SEQ ID NO: 167           moltype = AA  length = 33
FEATURE                  Location/Qualifiers
REGION                   1..33
                         note = Intermediate peptide
source                   1..33
                         mol_type = protein
                         organism = synthetic construct
SEQUENCE: 167
HHHHHHDEVD GIVEQCCTSI CSLYQLENYC NRR                                 33

SEQ ID NO: 168           moltype = AA  length = 34
FEATURE                  Location/Qualifiers
REGION                   1..34
                         note = Intermediate peptide
source                   1..34
                         mol_type = protein
                         organism = synthetic construct
SEQUENCE: 168
GHHHHHHDEV DGIVEQCCTS ICSLYQLENY CNRR                                34

SEQ ID NO: 169           moltype = AA  length = 42
FEATURE                  Location/Qualifiers
REGION                   1..42
                         note = Intermediate peptide
source                   1..42
                         mol_type = protein
                         organism = synthetic construct
SEQUENCE: 169
HHHHHHDEVD FVNQHLCGSH LVEALYLVCG ERGFFYTPKT RR                       42
```

-continued

```
SEQ ID NO: 170            moltype = AA   length = 41
FEATURE                   Location/Qualifiers
REGION                    1..41
                          note = Intermediate peptide
source                    1..41
                          mol_type = protein
                          organism = synthetic construct
SEQUENCE: 170
GHHHHHHDEV DFVNQHLCGS HLVEALYLVC GERGFFYTPK T                          41

SEQ ID NO: 171            moltype = AA   length = 31
FEATURE                   Location/Qualifiers
REGION                    1..31
                          note = Intermediate peptide
source                    1..31
                          mol_type = protein
                          organism = synthetic construct
SEQUENCE: 171
HHHHHHDEVD GIVEQCCTSI CSLYQLENYC N                                     31

SEQ ID NO: 172            moltype = AA   length = 32
FEATURE                   Location/Qualifiers
REGION                    1..32
                          note = Intermediate peptide
source                    1..32
                          mol_type = protein
                          organism = synthetic construct
SEQUENCE: 172
GHHHHHHDEV DGIVEQCCTS ICSLYQLENY CN                                    32

SEQ ID NO: 173            moltype = AA   length = 40
FEATURE                   Location/Qualifiers
REGION                    1..40
                          note = Intermediate peptide
source                    1..40
                          mol_type = protein
                          organism = synthetic construct
SEQUENCE: 173
HHHHHHDEVD FVNQHLCGSH LVEALYLVCG ERGFFYTPKT                            40

SEQ ID NO: 174            moltype = DNA   length = 6286
FEATURE                   Location/Qualifiers
misc_feature              1..6286
                          note = Plasmid
source                    1..6286
                          mol_type = other DNA
                          organism = synthetic construct
SEQUENCE: 174
tggcgaatgg gacgcgccct gtagcggcgc attaagcgcg gcgggtgtgg tggttacgcg       60
cagcgtgacc gctacacttg ccagcgccct agcgcccgct cctttcgctt tcttcccttc      120
ctttctcgcc acgttcgccg gctttccccg tcaagctcta atcgggggct ccctttaggg      180
gttccgattt agtgctttac ggcacctcga ccccaaaaaa cttgattagg gtgatggttc      240
acgtagtggg ccatcgccct gatagacggt ttttcgccct ttgacgttgg agtccacgtt      300
ctttaatagt ggactcttgt tccaaactgg aacaacactc aaccctatct cggtctattc      360
ttttgattta agggattttg ccgatttcgg cctattggtt aaaaaatg agctgattta        420
acaaaaattt aacgcgaatt ttaacaaaat attaacgttt acaatttcag gtggcacttt      480
tcggggaaat gtgcgcggaa cccctatttg tttatttttc taaatacatt caaatatgta      540
tccgctcatg agacaataac cctgataaat gcttcaataa tattgaaaaa ggaagagtat      600
gagtattcaa catttccgtg tcgcccttat tccctttttt gcggcatttt gccttcctgt      660
ttttgctcac ccagaaacgc tggtgaaagt aaaagatgct gaagatcagt tgggtgcacg      720
agtgggttac atcgaactgg atctcaacag cggtaagatc cttgagagtt ttcgccccga      780
agaacgtttt ccaatgatga gcacttttaa agttctgcta tgtggcgcgg tattatcccg      840
tattgacgcc gggcaagagc aactcggtcg ccgcatacac tattctcaga atgacttggt      900
tgagtactca ccagtcacag aaaagcatct tacggatggc atgacagtaa gagaattatg      960
cagtgctgcc ataaccatga gtgataacac tgcggccaac ttacttctga caacgatcgg     1020
aggaccgaag gagctaaccg cttttttgca acatggggga tcatgtaa ctcgccttga       1080
tcgttgggaa ccggagctga atgaagccat accaaacgac gagcgtgaca ccacgatgcc     1140
tgcagcaatg gcaacaacgt tgcgcaaact attaactggc gaactactta ctctagcttc     1200
ccggcaacaa ttaatagact ggatggaggc ggataaagtt gcaggaccac ttctgcgctc     1260
ggcccttccg gctggctggt ttattgctga taaatctgga gccggtgagc gtgggtctcg     1320
cggtatcatt gcagcactgg ggccagatgg taagccctcc cgtatcgtag ttatctacac     1380
gacggggagt caggcaacta tggatgaacg aaatagacag atcgctgaga taggtgcctc     1440
actgattaag cattggtaac tgtcagacca agtttactca tatatacttt agattgattt     1500
aaaacttcat ttttaattta aaaggatcta ggtgaagatc cttttgata atctcatgac      1560
caaaatccct taacgtgagt tttcgttcca ctgagcgtca gaccccgtag aaaagatcaa     1620
aggatcttct tgagatcctt ttttctgcg cgtaatctgc tgcttgcaaa caaaaaaacc     1680
accgctacca gcggtggttt gtttgccgga tcaagagcta ccaactcttt ttccgaaggt     1740
aactggcttc agcagagcgc agataccaaa tactgtcctt ctagtgtagc cgtagttagg     1800
```

-continued

```
ccaccacttc aagaactctg tagcaccgcc tacatacctc gctctgctaa tcctgttacc   1860
agtggctgct gccagtggcg ataagtcgtg tcttaccggg ttggactcaa gacgatagtt   1920
accggataag gcgcagcggt cgggctgaac gggggggttcg tgcacacagc ccagcttgga   1980
gcgaacgacc tacaccgaac tgagatacct acagcgtgag ctatgagaaa gcgccacgct   2040
tcccgaaggg agaaaggcgg acaggtatcc ggtaagcggc agggtcggaa caggagagcg   2100
cacgagggag cttccagggg gaaacgcctg gtatctttat agtcctgtcg ggtttcgcca   2160
cctctgactt gagcgtcgat ttttgtgatg ctcgtcaggg gggcggagcc tatggaaaaa   2220
cgccagcaac gcggccttttt tacggttcct ggccttttgc tggccttttg ctcacatgtt   2280
ctttcctgcg ttatcccctg attctgtgga taaccgtatt accgcctttg agtgagctga   2340
taccgctcgc cgcagccgaa cgaccgagcg cagcgagtca gtgagcgagg aagcggaaga   2400
gcgcctgatg cggtattttc tccttacgca tctgtgcggt atttcacacc gcatatatgg   2460
tgcactctca gtacaatctg ctctgatgcc gcatagttaa gccagtatac actccgctat   2520
cgctacgtga ctgggtcatg gctgcgcccc gacacccgcc aacacccgct gacgcgccct   2580
gacgggcttg tctgctcccg gcatccgctt acagacaagc tgtgaccgtc tccgggagct   2640
gcatgtgtca gaggttttca ccgtcatcac cgaaacgcgc gaggcagctg cggtaaagct   2700
catcagccgt gtcgtgaagc gattcacaga tgtctgcctg ttcatccgcg tccagctcgt   2760
tgagtttctc cagaagcgtt aatgtctggc ttctgataaa gcgggccatg ttaagggcgg   2820
ttttttcctg tttggtcact gatgcctccg tgtaaggggg atttctgttc atggggtaa    2880
tgataccgat gaaacgagag aggatgctca cgatacgggt tactgatgat gaacatgccc   2940
ggttactgga acgttgtgag ggtaaacaac tggcggtatg gatgcggcgg gaccagagaa   3000
aaatcactca gggtcaatgc cagcgcttcg ttaatacaga tgtaggtgtt ccacagggta   3060
gccagcagca tcctgcgatg cagatccgga acataatggt gcagggcgct gacttccgcg   3120
tttccagact ttacgaaaca cggaaaccga agaccattca tgttgttgct caggtcgcag   3180
acgttttgca gcagcagtcg cttcacgttc gctcgcgtat cggtgattca ttctgctaac   3240
cagtaaggca accccgccag cctagccggg tcctcaacga caggagcacg atcatgcgca   3300
cccgtggggc cgccatgccg gcgataatgg cctgcttctc gccgaaacgt ttggtggcgg   3360
gaccagtgac gaaggcttga gcgagggcgt gcaagattcc gaataccgca agcgacaggc   3420
cgatcatcgt cgcgctccag cgaaagcggt cctcgccgaa aatgacccag agcgctgccg   3480
gcacctgtcc tacgagttgc atgataaaga agacagtcat aagtgcggcg acgatagtca   3540
tgcccccgcg ccaccggaag gagctgactg ggttgaaggc tctcaagggc atcggtcgag   3600
atcccggtgc ctaatgagtg agctaactta cattaattgc gttgcgctca ctgcccgctt   3660
tccagtcggg aaacctgtcg tgccagctgc attaatgaat cggccaacgc gcggggagag   3720
gcggtttgcg tattgggcgc cagggtggtt tttcttttca ccagtgagac gggcaacagc   3780
tgattgccct tcaccgcctg gccctgagag agttgcagca agcggtccac gctggtttgc   3840
cccagcaggc gaaaatcctg tttgatggtg gttaacggcg ggatataaca tgagctgtct   3900
tcggtatcgt cgtatcccac taccgagatg tccgcaccaa cgcgcagccc ggactcggta   3960
atggcgcgca ttgcgcccag cgccatctga tcgttggcaa ccagcatcgc agtgggaacg   4020
atgccctcat tcagcatttg catggtttgt tgaaaaccgg acatggcact ccagtcgcct   4080
tcccgttccg ctatcggctg aatttgattg cgagtgagat atttatgcca gccagccaga   4140
cgcagacgcg ccgagacaga acttaatggg cccgctaaca gcgcgatttg ctggtgaccc   4200
aatgcgacca gatgctccac gcccagtcgc gtaccgtctt catgggagaa ataatactg    4260
ttgatgggtg tctggtcaga gacatcaaga aataacgccg gaacattagt gcaggcagct   4320
tccacagcaa tggcatcctg gtcatccagc ggatagttaa tgatcagccc actgacgcgt   4380
tgcgcgagaa gattgtgcac cgccgcttta caggcttcga cgccgcttcg ttctaccatc   4440
gacaccacca cgctggcacc cagttgatcg gcgcgagatt taatcgccgc gacaatttgc   4500
gacggcgcgt gcagggccag actggaggtg caacgccaa tcagcaacga ctgtttgccc    4560
gccagttgtt gtgccacgcg gttgggaatg taattcagct ccgccatcgc cgcttccact   4620
ttttcccgcg ttttcgcaga aacgtggctg gcctggttca ccacgcggga aacggtctga   4680
taagagacac cggcatactc tgcgacatcg tataacgtta ctggtttcac attcaccacc   4740
ctgaattgac tctcttccgg gcgctatcat gccataccgc gaaaggtttt gcgccattcg   4800
atggtgtccg ggatctcgac gctctccctt atgcgactcc tgcattagga agcagcccag   4860
tagtaggttg aggccgttga gcaccgccgc cgcaaggaat ggtgcatgca aggagatggc   4920
gcccaacagt ccccccggcca cgggccctgc caccataccc acgccgaaac aagcgctcat   4980
gagcccgaag tggcgagccc gatcttccc atcggtgatg tcggcgatat aggcgccagc    5040
aaccgcacct gtggccgg tgatgccggc cacgatgcgt ccggcgtaga ggatcgagat     5100
cgatctcgat cccgcgaaat taatacgact cactataggg gaattgtgag cggataacaa   5160
ttcccctcta gaaataattt tgtttaactt taagaaggag atatacatat gagcgataaa   5220
attattcacc tgactgacga cagttttgac acggatgtac tcaaagcgga cgggcgatc    5280
ctcgtcgatt tctgggcaga gtggtgcggt ccgtgcaaaa tgatcgcccc gattctggat   5340
gaaatcgctg acgaatatca gggcaaactg accgttgcaa aactgaacat cgatcaaaac   5400
cctggcactg cgccgaaata tggcatccgt ggtatcccga ctctgctgct gttcaaaaac   5460
ggtgaagtgg cggcaaccaa agtgggtgca ctgtctaaag tcagttgaa agagttcctc    5520
gacgctaacc tggccggttc tggttctggc catatgcacc atcatcatca tcattcttct   5580
ggtctggtgc cacgcggttc tggtatgaaa gaaaccgctg ctgctaaatt cgaacgccag   5640
cacatggaca gcccagatct gggtaccgac gacgacgaca aggccatggc tgatatcgga   5700
tccggtgacg aagtggacca tagccaaggc acctttacca gcgactatag caagtacctg   5760
gatagccgcc gtgcgcaaga ttttgttcaa tggctgatga cacctgcgg tgacgaggtg    5820
gatcacagcc agggcaccct caccagcgac tacagcaagt atttagatag ccgtcgtgct   5880
caggactttg tgcaatggtt aatgaatacc tgcggtgacg aagttgatca cagccaaggc   5940
accttcacca gcgattacag caaatatctg gacagccgtc gtgcgcagga ttttgtgcaa   6000
tggcttatga ataccgctgg cgatgaggtt gaccatagcc agggtacctt taccagcgac   6060
tacagcaaat acctggatag ccgtcgtgcg caagacttgc ttcaatggct gatgaatacc   6120
taactcgagc accaccacca ccaccactga gatccggctg ctaacaaagc ccgaaaggaa   6180
gctgagttgg ctgctgccac cgctgagcaa taactagcat aaccccttgg ggcctctaaa   6240
cgggtcttga ggggttttt gctgaaagga ggaactatat ccggat                   6286
```

```
SEQ ID NO: 175          moltype =     length =
SEQUENCE: 175
000

SEQ ID NO: 176          moltype =     length =
SEQUENCE: 176
000

SEQ ID NO: 177          moltype =     length =
SEQUENCE: 177
000

SEQ ID NO: 178          moltype =     length =
SEQUENCE: 178
000

SEQ ID NO: 179          moltype =     length =
SEQUENCE: 179
000

SEQ ID NO: 180          moltype =     length =
SEQUENCE: 180
000

SEQ ID NO: 181          moltype =     length =
SEQUENCE: 181
000

SEQ ID NO: 182          moltype =     length =
SEQUENCE: 182
000

SEQ ID NO: 183          moltype =     length =
SEQUENCE: 183
000

SEQ ID NO: 184          moltype =     length =
SEQUENCE: 184
000

SEQ ID NO: 185          moltype =     length =
SEQUENCE: 185
000

SEQ ID NO: 186          moltype =     length =
SEQUENCE: 186
000

SEQ ID NO: 187          moltype = AA   length = 333
FEATURE                 Location/Qualifiers
REGION                  1..333
                        note = Recombinant polypeptide
source                  1..333
                        mol_type = protein
                        organism = synthetic construct
SEQUENCE: 187
MSDKIIHLTD DSFDTDVLKA DGAILVDFWA EWCGPCKMIA PILDEIADEY QGKLTVAKLN   60
IDQNPGTAPK YGIRGIPTLL LFKNGEVAAT KVGALSKGQL KEFLDANLAG SGSGHMHHHH  120
HHSSGLVPRG SGMKETAAAK FERQHMDSPD LGTDDDDKAM ADIGGSDEVD SVSEIQLMHN  180
LGKHLNSMER VEWLRKKLQD VHNFSRHWSD EVDSVSEIQL MHNLGKHLNS MERVEWLRKK  240
LQDVHNFSRH WSDEVDSVSE IQLMHNLGKH LNSMERVEWL RKKLQDVHNF SRHWSDEVDS  300
VSEIQLMHNL GKHLNSMERV EWLRKKLQDV HNF                              333

SEQ ID NO: 188          moltype = AA   length = 162
FEATURE                 Location/Qualifiers
REGION                  1..162
                        note = Recombinant polypeptide
source                  1..162
                        mol_type = protein
                        organism = synthetic construct
SEQUENCE: 188
SDEVDSVSEI QLMHNLGKHL NSMERVEWLR KKLQDVHNFP ISDEVDSVSE IQLMHNLGKH   60
LNSMERVEWL RKKLQDVHNF PISDEVDSVS EIQLMHNLGK HLNSMERVEW LRKKLQDVHN  120
FPISDEVDSV SEIQLMHNLG KHLNSMERVE WLRKKLQDVH NF                    162
```

```
SEQ ID NO: 189          moltype = AA   length = 327
FEATURE                 Location/Qualifiers
REGION                  1..327
                        note = Recombinant polypeptide
source                  1..327
                        mol_type = protein
                        organism = synthetic construct
SEQUENCE: 189
MSDKIIHLTD DSFDTDVLKA DGAILVDFWA EWCGPCKMIA PILDEIADEY QGKLTVAKLN    60
IDQNPGTAPK YGIRGIPTLL LFKNGEVAAT KVGALSKGQL KEFLDANLAG SGSGHMHHHH   120
HHSSGLVPRG SGMKETAAAK FERQHMDSPD LGTDDDDKAM ADIGSGDEVD SVSEIQLMHN   180
LGKHLNSMER VEWLRKKLQD VHNFPISDEV DSVSEIQLMH NLGKHLNSME RVEWLRKKLQ   240
DVHNFPISDE VDSVSEIQLM HNLGKHLNSM ERVEWLRKKL QDVHNFPISD EVDSVSEIQL   300
MHNLGKHLNS MERVEWLRKK LQDVHNF                                      327

SEQ ID NO: 190          moltype = AA   length = 41
FEATURE                 Location/Qualifiers
REGION                  1..41
                        note = Artificial Sequence
source                  1..41
                        mol_type = protein
                        organism = synthetic construct
SEQUENCE: 190
SVSEIQLMHN LGKHLNSMER VEWLRKKLQD VHNFPISDEV D                        41

SEQ ID NO: 191          moltype = AA   length = 7
FEATURE                 Location/Qualifiers
REGION                  1..7
                        note = Peptide comprising linker and protease recognition
                         site
source                  1..7
                        mol_type = protein
                        organism = synthetic construct
SEQUENCE: 191
PISDEVD                                                              7

SEQ ID NO: 192          moltype = AA   length = 34
FEATURE                 Location/Qualifiers
REGION                  1..34
                        note = Intermediate peptide
source                  1..34
                        mol_type = protein
                        organism = synthetic construct
SEQUENCE: 192
HAEGTFTSDV SSYLEGQAAK EEFIAWLVRG RGRR                                34

SEQ ID NO: 193          moltype = AA   length = 304
FEATURE                 Location/Qualifiers
REGION                  1..304
                        note = Thioredoxin tag
source                  1..304
                        mol_type = protein
                        organism = synthetic construct
SEQUENCE: 193
MSDKIIHLTD DSFDTDVLKA DGAILVDFWA EWCGPCKMIA PILDEIADEY QGKLTVAKLN    60
IDQNPGTAPK YGIRGIPTLL LFKNGEVAAT KVGALSKGQL KEFLDANLAG SGSGHMHHHH   120
HHSSGLVPRG SGMKETAAAK FERQHMDSPD LGTDDDDKAM ADIGSGDEVD HSQGTFTSDY   180
SKYLDSRRAQ DFVQWLMNTC GDEVDHSQGT FTSDYSKYLD SRRAQDFVQW LMNTCGDEVD   240
HSQGTFTSDY SKYLDSRRAQ DFVQWLMNTC GDEVDHSQGT FTSDYSKYLD SRRAQDFVQW   300
LMNT                                                                304

SEQ ID NO: 194          moltype = AA   length = 310
FEATURE                 Location/Qualifiers
REGION                  1..310
                        note = Recombinant polypeptide
source                  1..310
                        mol_type = protein
                        organism = synthetic construct
SEQUENCE: 194
MSDKIIHLTD DSFDTDVLKA DGAILVDFWA EWCGPCKMIA PILDEIADEY QGKLTVAKLN    60
IDQNPGTAPK YGIRGIPTLL LFKNGEVAAT KVGALSKGQL KEFLDANLAG SGSGHMHHHH   120
HHSSGLVPRG SGMKETAAAK FERQHMDSPD LGTDDDDKAM ADIGSGDEVD HSQGTFTSDY   180
SKYLDSRRAQ DFVQWLMNTP HGGDEVDHSQ GTFTSDYSKY LDSRRAQDFV QWLMNTPHGG   240
DEVDHSQGTF TSDYSKYLDS RRAQDFVQWL MNTPHGGDEV DHSQGTFTSD YSKYLDSRRA   300
QDFVQWLMNT                                                          310
```

```
SEQ ID NO: 195         moltype = AA  length = 313
FEATURE                Location/Qualifiers
REGION                 1..313
                       note = Recombinant polypeptide
source                 1..313
                       mol_type = protein
                       organism = synthetic construct
SEQUENCE: 195
MSDKIIHLTD DSFDTDVLKA DGAILVDFWA EWCGPCKMIA PILDEIADEY QGKLTVAKLN    60
IDQNPGTAPK YGIRGIPTLL LFKNGEVAAT KVGALSKGQL KEFLDANLAG SGSGHMHHHH   120
HHSSGLVPRG SGMKETAAAK FERQHMDSPD LGTDDDDKAM ADIGSGDEVD HSQGTFTSDY   180
SKYLDSRRAQ DFVQWLMNTS RHWGDEVDHS QGTFTSDYSK YLDSRRAQDF VQWLMNTSRH   240
WGDEVDHSQG TFTSDYSKYL DSRRAQDFVQ WLMNTSRHWG DEVDHSQGTF TSDYSKYLDS   300
RRAQDFVQWL MNT                                                     313

SEQ ID NO: 196         moltype = AA  length = 314
FEATURE                Location/Qualifiers
REGION                 1..314
                       note = Recombinant polypeptide
source                 1..314
                       mol_type = protein
                       organism = synthetic construct
SEQUENCE: 196
MSDKIIHLTD DSFDTDVLKA DGAILVDFWA EWCGPCKMIA PILDEIADEY QGKLTVAKLN    60
IDQNPGTAPK YGIRGIPTLL LFKNGEVAAT KVGALSKGQL KEFLDANLAG SGSGHMHHHH   120
HHSSGLVPRG SGMKETAAAK FERQHMDSPD LGTDDDDKAM ADIGSGRRHA EGTFTSDVSS   180
YLEGQAAKEE FIAWLVRGRG RRGSKRHAEG TFTSDVSSYL EGQAAKEEFI AWLVRGRGRR   240
GSRRHAEGTF TSDVSSYLEG QAAKEEFIAW LVRGRGRRGS KRHAEGTFTS DVSSYLEGQA   300
AKEEFIAWLV RGRG                                                    314

SEQ ID NO: 197         moltype = AA  length = 322
FEATURE                Location/Qualifiers
REGION                 1..322
                       note = Recombinant polypeptide
source                 1..322
                       mol_type = protein
                       organism = synthetic construct
SEQUENCE: 197
MSDKIIHLTD DSFDTDVLKA DGAILVDFWA EWCGPCKMIA PILDEIADEY QGKLTVAKLN    60
IDQNPGTAPK YGIRGIPTLL LFKNGEVAAT KVGALSKGQL KEFLDANLAG SGSGHMHHHH   120
HHSSGLVPRG SGMKETAAAK FERQHMDSPD LGTDDDDKAM ADIGSGDEVD HAEGTFTSDV   180
SSYLEGQAAK EEFIAWLVRG RGPHGGDEVD HAEGTFTSDV SSYLEGQAAK EEFIAWLVRG   240
RGPHGGDEVD HAEGTFTSDV SSYLEGQAAK EEFIAWLVRG RGPHGGDEVD HAEGTFTSDV   300
SSYLEGQAAK EEFIAWLVRG RG                                           322

SEQ ID NO: 198         moltype =     length =
SEQUENCE: 198
000

SEQ ID NO: 199         moltype = AA  length = 43
FEATURE                Location/Qualifiers
REGION                 1..43
                       note = Recombinant polypeptide
source                 1..43
                       mol_type = protein
                       organism = synthetic construct
SEQUENCE: 199
SVSEIQLMHN LGKHLNSMER VEWLRKKLQD VHNFSRHWSD EVD                      43

SEQ ID NO: 200         moltype = AA  length = 9
FEATURE                Location/Qualifiers
REGION                 1..9
                       note = Recombinant polypeptide
source                 1..9
                       mol_type = protein
                       organism = synthetic construct
SEQUENCE: 200
SRHWSDEVD                                                             9

SEQ ID NO: 201         moltype =     length =
SEQUENCE: 201
000

SEQ ID NO: 202         moltype =     length =
SEQUENCE: 202
000
```

COMPOSITIONS AND METHODS FOR PEPTIDE PRODUCTION

This application is a 35 U.S.C. § 111 patent application that claims the benefit of priority and is entitled to the filing date pursuant to 35 U.S.C. § 120 of International Patent Application PCT/US2022/012384, filed Jan. 13, 2022, an international patent application which claims the benefit of priority and is entitled to the filing date pursuant to 35 U.S.C. § 119(e) of U.S. Provisional Patent Application 63/137,612, filed Jan. 14, 2021, the content of each of which is hereby incorporated by reference in its entirety.

REFERENCE TO SEQUENCE LISTING

Submitted as part of this patent application is a Sequence Listing filed as a XML file named UEBIO3-0001US-SeqList-ST26.xml having a file size of 188,000 bytes and generated on Jan. 5, 2023, the content of which is hereby expressly incorporated by reference in its entirety.

FIELD OF DISCLOSURE

The present disclosure generally relates to systems, compositions, and methods for improved production of recombinant polypeptides. In particular embodiments, constructs containing open reading frame(s) encoding a polypeptide that comprises a plurality of linked peptides may be used to simplify or decrease the number of steps necessary to produce the purified peptides, and/or increase the yield of the purified peptide products. Accordingly, the present invention relates to nucleic acid molecules comprising the aforementioned constructs, cells comprising the nucleic acid molecules, systems and production apparatus comprising the nucleic acid molecules and/or cells, and methods for recombinant peptide production including and/or utilizing any and all of the foregoing.

BACKGROUND

Purified peptides are useful in many applications; e.g., in diagnostic applications, as therapeutic agents, as food ingredients/additives, and as pathogen inhibitors. Short and medium-sized peptides are typically produced by chemical synthesis methods. However, these methods are most economical for only the shortest peptides, and post-translational modifications cannot be easily implemented during chemical synthesis. Furthermore, chemical synthesis requires the use of extremely hazardous chemicals.

Recombinant DNA technology provides a sub-optimal replacement for chemical synthesis, though it is preferable in certain circumstances. The recombinant approach utilizes cells' endogenous protein production machinery to produce heterologous peptides. Recombinant peptide synthesis requires many complex biochemical processes, including transcription, translation, protein folding, and post-translational modification (e.g., glycosylation, and disulfide-bond formation), which are generally catalyzed by enzymes. The technical use of these endogenous processes for the production of recombinant peptides remains challenging, e.g., due to their differential operation on the same precursor polypeptide in different cells.

Furthermore, the yield obtainable with conventional recombinant peptide production is not high enough to compete with chemical synthesis methods for the synthesis of most medium size peptides. Production of polypeptides containing tandem repeats of desirable peptides is one strategy designed to address these problems, especially to increase the yield. However, existing cleavage strategies utilizing either chemicals or proteases to cleave the peptides from the translated polypeptide leave extra amino acids in the final peptide product. These extra amino acids have numerous significant disadvantages that are prohibitive with respect to the intended use of the peptides; e.g., the extra amino acids can create problems for medical applications by initiating an immunogenic response, and the extra amino acids also can interfere with the physiological functions of the peptides. Costly clinical trials are therefore required to validate their use for medical applications, even when the use of the peptide without the extra amino acids has already been approved.

An additional barrier to the use of tandem repeats to increase the peptide production yield is that the chimeric protein must be designed so that the cleavage sites are all accessible to the cleaving agent or else the intended increase in peptide yield will not be achieved.

Several solutions have been proposed to address some of the foregoing obstacles to reaching the full promise of recombinant peptide production technology, but none are sufficient to provide a production platform that is generally useful to produce substantially all desired peptides with the exact intended sequence in a high yield, in a cost-effective and environmentally friendly manner, independent of peptide length, and without the formation of inclusion bodies.

U.S. Pat. No. 6,051,399 describes a method for the production of recombinant C-terminal amidated peptides from tandem repeats by introducing a heterologous cysteine at the amino-terminus and a methionine at the carboxy-terminus of a linker peptide. This requires that the resulting peptides are devoid of either free cysteine or methionine. When either of those amino acids is present in the desired peptide, it is impossible to produce the exact sequence of the peptide. For example, when the C-terminus of the linker sequence ends with a cysteine, the N-terminus of the peptide becomes modified by the iminothiazolidine-carboxyl group during the cleavage reaction. Alternatively, when the linker peptide starts with a methionine, then homoserine lactone is introduced in the peptide. These modifications interfere with many applications for the peptide, and therefore the methods are not suitable for a general production system that can be adapted for the production of any peptide. In addition, the design of tandem repeats should be such that the cleavage sequences are accessible to the chemical agents and proteases. If not, denaturation of the tandem repeat is needed in order to expose the cleavage sites. This can be problematic, especially for the enzymatic cleavage of the tandem repeat, because the enzyme itself becomes denatured in the presence of denaturing agents.

BRIEF SUMMARY OF DISCLOSURE

This disclosure describes a solution to the problem of producing recombinant product peptides with an exact intended target sequence with the added benefits of increased yield, and limitation of the resources required by employing environmentally friendly reagents and processes, and by eliminating process steps. Therefore, the disclosure provides constructs, systems, and polypeptides containing linked peptides that are used in embodiments to efficiently produce a wide range of product peptides that are suitable for many applications, ranging from nutritional to medical and pharmaceutical uses in humans or animals.

In embodiments, enzyme-catalyzed proteolysis is utilized alone or in combination with chemical proteolysis to cleave a recombinant polypeptide comprising multiple peptide repeats into product peptides consisting of a desired target amino acid sequence. In particular embodiments, the recombinant polypeptide is soluble in an aqueous environment; e.g., the cytosol of a cell (e.g., a bacterial cell such as *E. coli*). Embodiments herein therefore include peptide repeat-containing polypeptides as described herein, nucleic acids encoding such polypeptides, host cells and recombinant production platforms comprising such constructs and/or polypeptides, and methods utilizing the foregoing for the production of product peptides consisting of a target amino acid sequence.

Some embodiments therefore include a recombinant polypeptide (e.g., a translation product polypeptide) comprising a plurality of product peptides with a target sequence, further comprising at least one intervening "linker sequence" between each product peptide, wherein linker sequences comprise cleavage sites of proteases in a first proteolysis reaction to yield intermediate peptides that are subsequently enzymatically or chemically processed into product peptides consisting of the target sequence. Examples include polypeptides wherein the product peptides have an identical target amino acid sequence, examples wherein the polypeptide comprises two product peptides with different target amino acid sequences, and examples wherein the polypeptide comprises more than two product peptides with different target amino acid sequences.

In particular aspects, the plurality of intermediate peptides and intervening linker sequences comprise at least one linker sequence (e.g., more than one or all of the linker sequences) comprising a protease cleavage site (P.C.S.) that recognizes two or four consecutive basic amino acids. Proteolysis of the polypeptide with such a protease yields the intermediate peptide, comprising basic amino acids at the carboxy-terminus of the target amino acid sequence of the product peptide. In examples herein, proteolysis of the intermediate peptide by a carboxypeptidase eliminates the remaining extra basic residues to yield the product peptide consisting of the target amino acid sequence.

In particular aspects, the use of small amino acids, especially glycine, in the linker sequence combined with the use of proteases that recognize high number of charged amino acids may ensure the exposure of the cleavage sites to the cleaving reagents.

In particular aspects, the plurality of intermediate peptides and intervening linker sequences comprise at least one linker sequence (e.g., more than one or all of the linker sequences) comprising an amino-terminal chemical cleavage sequence (C.C.S.) and a cleavage site of a protease that leaves no extraneous amino acid at the P1' position. In examples herein, proteolysis of the polypeptide with such a protease yields the intermediate peptide comprising the amino-terminal C.C.S. In examples herein, chemical proteolysis of the intermediate peptide yields the product peptide consisting of the target amino acid sequence.

In some embodiments, proteolysis of the polypeptide with one or more retroviral proteases may be used alone or in combination with one or more additional proteases. Proteolysis by retroviral protease may occur at a Type 1 cleavage site having an aromatic residue and proline at P1 and P1' positions, respectively, or Type 2 cleavage site having a hydrophobic residue at P1 position. Retroviral proteases relying on the C-terminal side of the sessile bond for the substrate recognition may be used on a polypeptide in combination with other proteases that leave no amino acid at the P1' position.

In examples, the recombinant polypeptide further comprises at least one peptide unit that does not form part of the intermediate peptide product(s) or linker sequence(s); e.g., at the N-terminal end of the polypeptide, or on the C-terminal end of the polypeptide. A polypeptide in certain embodiments may comprise such a peptide unit on both the N-terminal and C-terminal ends of the polypeptide. Non-limiting examples of such peptide units include tags that improve detection, purification, and/or solubilization; N-terminal or C-terminal capping units; receptors; signal domains; and targeting domains. In particular examples, the recombinant polypeptide comprises a tag that facilitates purification (e.g., affinity purification) and/or solubilization of the polypeptide.

Some embodiments include a nucleic acid molecule comprising a polynucleotide encoding a recombinant polypeptide as described herein. Examples include ribonucleic acid (RNA) molecules that are translated to produce the recombinant polypeptide; a deoxyribonucleic acid (DNA) construct comprising a polynucleotide encoding such an RNA molecule (e.g., comprised in an expression cassette); and/or a DNA molecule (e.g., expression vectors, transformation vectors, stably-replicating plasmids, and genomic molecules (e.g., a chromosome comprising the construct)). A DNA construct or molecule herein may comprise one or more regulatory sequences; e.g., a promoter that functions in a cell or cell-based system to initiate transcription of an operably linked polypeptide, transcription termination sequence, 5'-untranslated region (5'-UTR), and/or a 3'-untranslated region (3'-UTR).

Particular embodiments further include the protease that recognizes two or four consecutive basic amino acids and/or the protease that leaves no extraneous amino acid at the P1' cleavage position, and/or a nucleic acid construct or molecule encoding said protease(s). In particular examples, the DNA construct or molecule encoding a recombinant polypeptide as described herein further comprises a polynucleotide encoding the protease(s). However, particular examples include the recombinant polypeptide; a DNA construct or molecule encoding a recombinant polypeptide and the protease(s); a DNA construct or molecule encoding the protease(s), or any combination of the foregoing (e.g., in a production cell, cell lysate, a bioreactor, or a coupled cell-free transcription-translation system). In one non-limiting example, a polynucleotide encoding the protease may be operably positioned within the construct comprising the polynucleotide encoding the recombinant polypeptide in a DNA molecule, wherein the DNA molecule may further comprise at least one additional regulatory sequence (e.g., a promoter or internal ribosome entry site sequence) positioned between the polynucleotide encoding the protease and the polynucleotide encoding the recombinant polypeptide.

Further embodiments herein further include recombinant production systems for production of the aforementioned product peptides consisting of target sequences. For example, particular embodiments herein comprise cells, cell lysates, bioreactors, and coupled cell-free transcription-translation systems comprising a DNA construct or molecule encoding at least one of the recombinant polypeptides. In specific examples, a cell, cell lysate, bioreactor, or coupled cell-free transcription-translation system comprises a DNA construct or molecule comprising a polynucleotide encoding the recombinant polypeptide (and/or a polynucleotide encoding an additional peptide unit) that has been codon optimized for expression in a cell, cell lysate, bioreactor, or coupled cell-free transcription-translation system. In these and other examples, a polynucleotide encoding the recombinant polypeptide may comprise nucleotide sequences that have been codon-optimized to encode product peptides with the same target amino acid sequence; e.g., to reduce the effect of RNAi silencing in the host cell.

Consistent with the foregoing, some embodiments herein include methods for producing at least one product peptide consisting of a target amino acid sequence; e.g., a target amino acid sequence that is suitable for an intended use (e.g., a medical and pharmaceutical use in humans or animals). As alluded to previously, such methods produce product peptides consisting of target amino acid sequences, without additional amino acids or undesired internal modifications, and with increased yield and desirable reaction parameters (e.g., limited steps, inexpensive reagents, and/or environmentally friendly reagents) with respect to conventional recombinant production processes. In embodiments, a recombinant (e.g., soluble) polypeptide of the invention is contacted with a protease (e.g., by admixing the polypeptide and the protease in a reaction mixture, by expression of the polypeptide in a cell or cell-based system comprising the protease or vice versa, or by expression of both the polypeptide and protease in a cell or cell-based system) thereby cleaving the polypeptide at a cleavage site of the protease to produce a plurality of intermediate peptides comprising a product peptide amino acid sequence. The protease may be a protease that recognizes two or four consecutive basic amino acids, or a protease that leaves no amino acid at the P1' position. In embodiments wherein the protease recognizes two or four consecutive basic amino acids, the intermediate peptides may be contacted with a second protease (e.g., a carboxypeptidase) that removes basic residues remaining from the first proteolysis step, thereby yielding product peptide(s) consisting of target amino acid sequences. In embodiments wherein the protease leaves no amino acid at the P1' position, the intermediate peptide may be contacted with a chemical agent under appropriate conditions, thereby yielding product peptide(s) consisting of target amino acid sequences by chemical proteolysis.

In some embodiments, the recombinant polypeptide may be produced in a cell or cell-based system, and purified therefrom to isolate the polypeptide; e.g. and without limitation, by affinity purification with immobilized agents (e.g., small molecules and antibodies) that bind a tag comprised within the polypeptide. In some embodiments, the product peptide(s) may be purified from the second proteolysis reaction, catalyzed by either the second protease or the chemical agent.

The foregoing and other features will become more apparent from the following detailed description, which proceeds with reference to the accompanying figures.

BRIEF DESCRIPTION OF THE FIGURES

FIG. 1A shows a linear representation of recombinant polypeptides for the production of product peptides. As in the scheme depicted in FIG. 1A, the recombinant polypeptides may comprise a TAG, as shown, followed first by a peptide comprising a cleavage site for a protease (e.g., selected from Enterokinase, Factor Xa, caspases, and Granzyme B) that leaves no amino acid at the P1' position, and then by Repeating Units (RUs) that each comprise a chemical cleavage sequence (C.C.S.), linker sequence ($L_{nk}$), a protease cleavage site (P.C.S.) that leaves no amino acid at the P1' position, and a product peptide (FIG. 1B). As shown in FIG. 1C, proteolysis with the protease (Enzyme) releases intermediate peptides, each comprising a product peptide with a carboxy-terminal chemical cleavage sequence (C.C.S.), linker sequence ($L_{nk}$), and the protease cleavage site (P.C.S.). Chemical cleavage of the intermediate peptides with an appropriate chemical agent(s) (Chemical Agent) yields the product peptides consisting of their target amino acid sequences without extraneous amino acids. Linker amino acids are placed between C.C.S. and the enzyme recognition sequence and can be identical or variable for each repeating unit. Nonetheless, three amino acids of Gly, Ala, and Ser are preferred as the last amino acid of the linker sequence.

FIG. 2A shows a linear representation of recombinant polypeptides for the production of product peptides. The recombinant polypeptides may comprise a TAG, as shown, followed first by a peptide comprising a cleavage site for a first protease (e.g., selected from Enterokinase, Factor Xa, caspases, and Granzyme B), protease 1 cleavage site (P1.C.S.), that leaves no amino acid at the P1' position, and then by Repeating Units (RUs) that each comprise a cleavage site for a second protease (such as HIV-1 protease), protease 2 cleavage site (P2.C.S.), linker sequence ($L_{nk}$), a cleavage site for the first protease that leaves no amino acid at the P1' position, and a product peptide (FIG. 2B). As shown in FIG. 2C, proteolysis with the first protease (Enzyme 1) releases the peptide product and intermediate peptides, each comprising product peptide, P2.C.S., $L_{nk}$, and P1.C.S. Treatment with the second protease (Enzyme 2) yields the product peptides consisting of their target amino acid sequences without extraneous amino acids. Linker amino acids are placed between P2.C.S. and P1.C.S. and can be identical or variable for each repeating unit. Nonetheless, three amino acids of Gly, Ala, and Ser are preferred as the last amino acid of the linker sequence. The order by which enzymes are added can be switched or they can be added simultaneously.

FIG. 3A shows a linear representation of recombinant polypeptides for the isolation (e.g., including purification) of product peptides. The recombinant polypeptides may comprise a TAG (e.g., selected from affinity purification tags and solubilization tags), as shown, followed by Repeating Units (Rus) (FIG. 3B) that each comprise a peptide with a cleavage site for a first protease (Enzyme 1) (e.g., selected from Furin, protein convertases, neuroendocrine convertases, and Kexin) that cleaves at the C-terminal side of an even number of consecutive basic residues (two to four). As shown in FIG. 3C, proteolysis with Enzyme 1 releases intermediate peptides, each comprising a product peptide and carboxy-terminal Basic amino acids ($B_m$). Also shown in FIG. 3C, further proteolysis of the intermediate peptides with a carboxypeptidase (Enzyme 2) (e.g., selected from CPN (also known as kininase I), CPB, CPU, and metallocarboxypeptidase D (CPD)) yields product peptides consisting of their target amino acid sequences without extraneous amino acids.

FIG. 5A shows SDS-PAGE analysis (Tricine gel) of four repeats of Thioredoxin tagged glucagon before and after hydrolysis by caspase-7. From left to right: protein marker, Thioredoxin tagged glucagon treated with caspase-7, glucagon and the repeating unit (RU-glucagon linked to the linker sequence and NTCB cleavage sequence, and the caspase recognition sequence) purified by C18 column, mature glucagon, and the thioredoxin tagged glucagon. FIG. 5B shows SDS-PAGE analysis (Tricine gel) of four repeats of Trx tagged-glucagon before and after limited hydrolysis by caspase-7 producing all expected fragments demonstrating that all designed caspase cleavage sites are almost equally accessible to the protease. FIG. 5C shows linear mode MALDI-TOF mass spectrometric analysis of glucagon and glucagon repeating unit (RU-glucagon attached to NTCB cleavage sequence, the linker peptide, and the caspase recognition sequence) using CHCA as the matrix. Presence of peptide fragments with the expected molecular weights proves that the enzyme has cleaved the Trx tagged tandem repeat of glucagon correctly at the designated sites.

FIG. 6A shows SDS-PAGE (Tricine) of Trx-HIV teriparatide, four repeats, before caspase-7 treatment (lane 1) and the HPLC purified teriparatide and its repeating unit obtained by caspase-7 hydrolysis of Trx-Teriparatide (lane 2). FIG. 6B shows hydrolysis conditions of Trx-HIV teriparatide by caspases can be set to either produce teriparatide and the repeating unit of Teriparatide in an insoluble, lane 1, or soluble, lane 2, forms as revealed by SDS-PAGE (Tricine). The observed peptide bands are the elution products at 20.2 minutes from the Biorad Hipore C18 column. Lane 3 shows the mature Teriparatide. FIG. 6C shows HPLC analysis of Trx-HIV teriparatide, four repeats after treatment with caspase-7 using Biorad-Hipore C18 column. A gradient from 5% to 90% acetonitrile in 0.1% trifluoracetic acid was stablished for a period of 30 minutes. A mixture of teriparatide and its repeating unit are eluted at 20.2 minutes.

FIG. 6D shows MALDI-TOF Mass spectrometric confirmation of correct processing of Trx-Teriparatide, four repeats possessing caspase-3/-7 and HIV1 protease recognition sites, by caspase-7. The dried peptides were dissolved in water and cleaned with Rainin C18 tips according to the manufacture's protocol and spotted on MALDI plate. Equal volume of the CHCA matrix was added and dried then subjected to MS analysis in a linear mode.

FIG. 7A shows SDS-PAGE analysis (Tricine) of complete Hydrolysis of Trx-Teriparatide using caspase-7 producing thioredoxin (Trx tag), repeating unit of teriparatide, and teriparatide. FIG. 7B SDS-PAGE analysis (Tricine) of limited hydrolysis of Trx-Ni-Teriparatide, four repeats, with caspase-3 and -7 and conversion of repeating unit of Teriparatide to mature Teriparatide using 1 mM concentration of $NiCl_2$ at 50° C. FIG. 7C shows dose dependent cleavage of Trx-Teriparatide, four repeats, by incubation with caspase-7 for 2 hours at 30° C. analyzed by SDS-PAGE analysis (Glycine). FIG. 7D shows complete conversion of repeating unit of teriparatide to mature teriparatide following $NiCl_2$ treatment, 1 mM, at 50° C. as confirmed by MALDI-TOF mass spectrometry. CHCA was used as the matrix. FIG. 7E shows ESI-MS analysis of Teriparatide and its repeating unit containing $Ni^{2+}$ cleavage sequence obtained using Thermo Q-Exactive orbitrap mass spectrometer. FIG. 7F and FIG. 7G show the molecular weights of the pre-stained protein marker for Tricine and Glycine gels, respectively.

(FIG. 8A) and MALDI-TOF analysis of the produced peptides between 2500 and 10000 Da (FIG. 8B). The expected molecular weight for a singly protonated oxidized form of the repeating unit is 5246.9.

DETAILED DESCRIPTION OF THE INVENTION

(i) Definitions

Figure 1A:
FIGS. 1A-1C includes diagrams that are helpful to illustrate other aspects of embodiments herein.
Figure 1B:
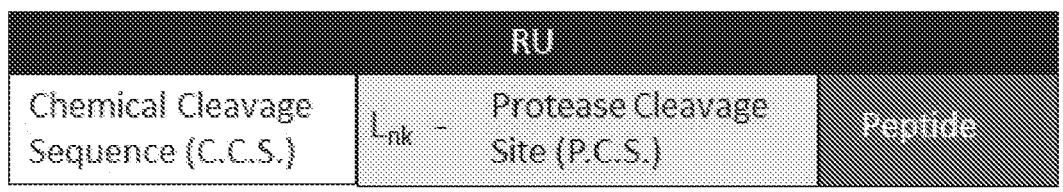
Figure 1C:
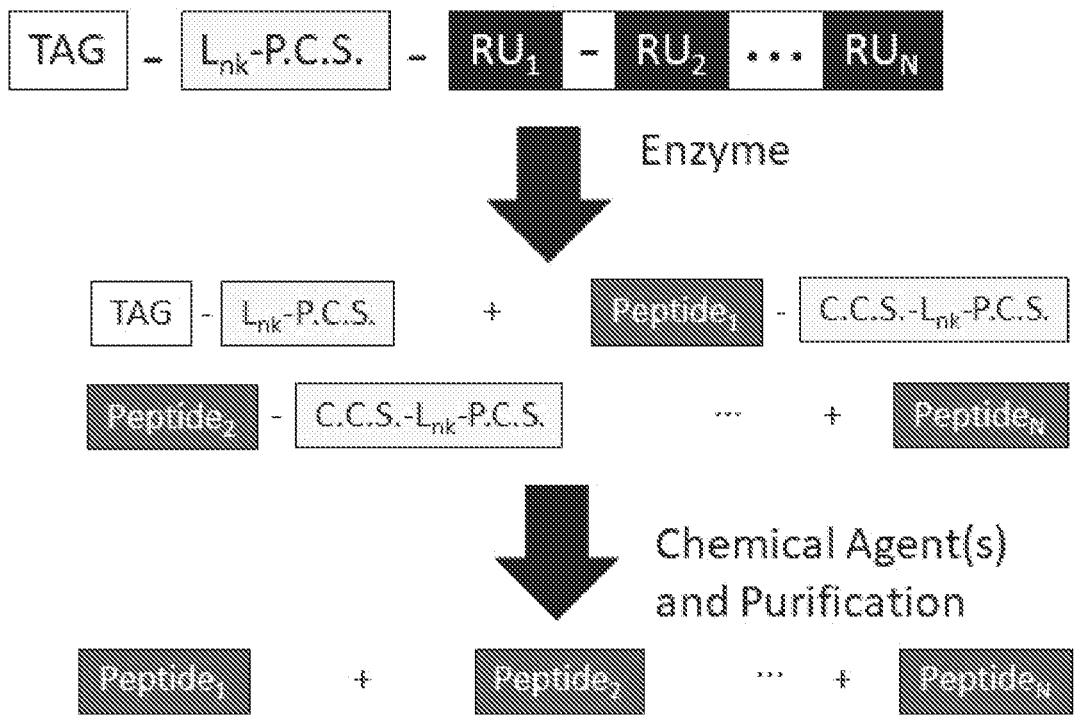
Figure 2A:
FIGS. 2A-2C includes diagrams that are helpful to illustrate other aspects of embodiments herein.
Figure 2B:
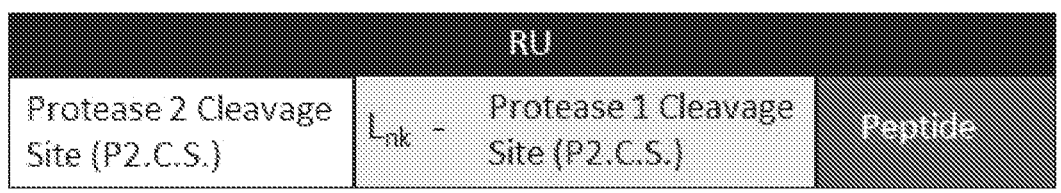
Figure 2C:
Figure 2C:
Figure 2C:
Figure 2C:
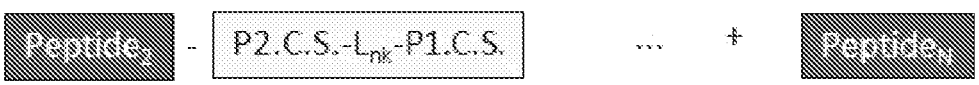
Figure 2C:
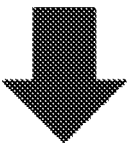
Figure 2C:
Figure 3A:
FIGS. 3A-3C include diagrams that are helpful to illustrate the principle underlying aspects of embodiments herein.
Figure 3B:
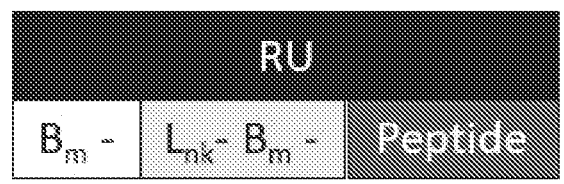
Figure 3C:
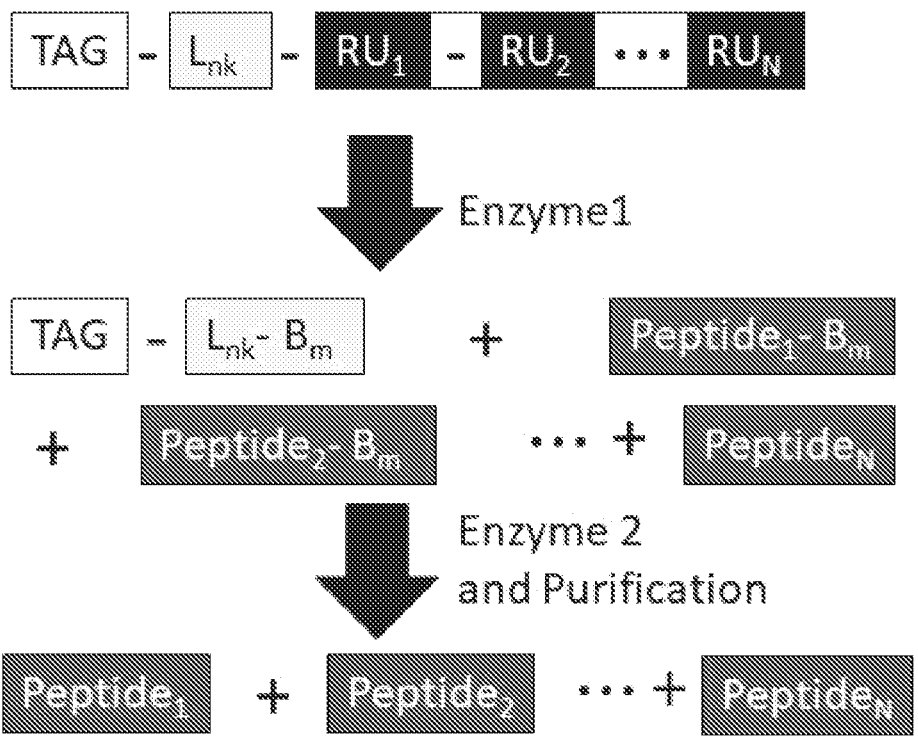

The following definitions, unless otherwise stated, apply to all aspects and embodiments of the present application.

In order to facilitate review of the various embodiments of the disclosure, the following explanations of specific terms are provided. Unless otherwise specifically indicated, all terms herein have their normal and customary meaning in the art.

Caspase: Caspases are a known and defined family of proteases that are classified based on their specific cysteine protease activity. Unless it is specifically stated or it is clear from the context, the term "caspase," as it is used herein, refers to Caspase-1, Caspase-2, Caspase-3, Caspase-4, Caspase-5, Caspase-6, Caspase-7, Caspase-8, Caspase-9, Caspase-10, Caspase-14, Granzyme B, and CED-3. Of specific interest in certain examples herein are Caspase-3 and Caspase-7. Caspases share an exquisite specificity for cleaving proteins at sites next to certain aspartic acid residues at the P1 position. Across the family, caspases are tolerant to amino acid variation at the P2 position. Talanian et al. (1997) J. Biol. Chem. 272(15):9677-82.

Different recognition sites of different caspases have been determined from proteomic studies. Caspases generally have preferred recognition sites, though caspases are tolerant of variation at the P2 position; e.g., Caspase-3 and Caspase-7 exhibit a preference for DEXD (SEQ ID NO: 33), even though it has a low frequency among natural cleavage sites of the enzymes. Particularly preferred in examples herein is the recognition site for Caspase-3 and Caspase-7 comprising a V in the variable P2 position (SEQ ID NO: 34). By way of further example, Caspase-1 prefers Y or F in the P4 position (SEQ ID NOs: 36-37), and Caspase-8 prefers T or V in the P4 position (SEQ ID NO: 42). Many additional cleavage sites that correspond to different caspases are known in the art. Further examples are provided in Table 1, below.

Isolated: An "isolated" biological component (such as a polynucleotide, recombinant polypeptide, and a product peptide) has been substantially separated or produced apart from (e.g., purified_away from) other biological components in the molecule (e.g., a DNA molecule or recombinant polypeptide), and/or cell of the organism in which the component naturally occurs (e.g., other chromosomal and extra-chromosomal DNA and RNA, and proteins), while effecting a chemical or functional change in the component (e.g., a polynucleotide may be isolated from a chromosome by breaking chemical bonds connecting the polynucleotide to the remaining DNA in the chromosome). Polynucleotide, protein (e.g., recombinant polypeptides), and peptides that have been "isolated" include nucleic acid molecules, proteins/polypeptides, and peptides purified by standard purification methods. The term also specifically embraces molecules and proteins prepared by recombinant expression in a host cell, as well as chemically-synthesized nucleic acid molecules, proteins/polypeptides, and peptides.

Polypeptides, Proteins, and Peptides: As used herein, the terms "polypeptide" and "protein" are used interchangeably to refer to a polymer of amino acids. The molecules encompassed by these terms also include those with post-translational modifications; e.g., glycosylation, acetylation, phosphorylation, and disulfide bonds. For the purposes of the description of the present invention, the term "peptide" is generally used to distinguish polymers of amino acids that are found within repeating units of a polypeptide from the polypeptide itself. However, those in the art will understand that this distinction is made solely for the purpose of clarity within the context of this disclosure, and will further understand that "peptides" that are produced using the compositions and methods herein may themselves comprise distinct domains and units that could themselves be classified as peptides. Polypeptides and peptides of certain embodiments herein may consist entirely of naturally-occurring amino acids, or they may incorporate non-natural and/or labeled amino acids. Examples of non-natural amino acids are beta-amino acids and modified natural amino acids that can still be incorporated into a peptide or polypeptide. Daniels et al. (2007) J. Am. Chem. Soc. 129:1532-3; Hendrickson et al. (2004) Annu. Rev. Biochem. 73:147-76.

The amino acid sequences of polypeptides and peptides of embodiments herein are described generally using terminology of the classic protease cleavage nomenclature, surrounding a cleavage site (< >) located between P1 and P1' amino acids of substrate polypeptide, which site is described as: Pn-P4-P3-P2-P1< >P1'-P2'-Pn'.

Nucleic acid molecule: As used herein, the term "nucleic acid molecule" refers to a polymeric form of nucleotides, including RNA, cDNA, genomic DNA, and synthetic forms and mixed polymers of the above. A nucleotide may refer to a ribonucleotide, deoxyribonucleotide, or a modified form of either type of nucleotide. A nucleic acid molecule can include either or both naturally occurring and modified nucleotides linked together by naturally occurring and/or non-naturally occurring nucleotide linkages.

Nucleic acid molecules may comprise structural units referred to herein as "polynucleotides," which distinguish a physical sequential ordering of nucleotides in a polymer, as opposed to "nucleotide sequence," which refers to the information contained in the physical polynucleotide.

Exogenous: The term "exogenous," as applied to nucleic acid molecules, polynucleotides, polypeptides, and peptides herein, refers to one or more of the same that are not normally present within their specific environment or context. For example, if a host cell is transformed such that it contains a polynucleotide or expresses a polypeptide that does not occur in the untransformed host cell in nature, then that polynucleotide or polypeptide is exogenous to the host cell. Furthermore, a polynucleotide that is present in a plasmid or vector in the host cell is exogenous to the host cell when the plasmid or vector is not normally present in the genome of the host cell. Specifically included within the scope of the term "nucleic acid molecule" are genomic nucleic acid molecules, such as chromosomes or self-replicating plasmids that comprise polynucleotides not normally present in the naturally-occurring chromosomes or plasmids of the host cell. Specifically included within the term "polynucleotide" are those polynucleotides that are integrated in the genomic DNA of the host cell; e.g., after a transformation event.

Heterologous: The term "heterologous," as applied to nucleic acid molecules, polynucleotides, polypeptides, and peptides herein, means of different origin. For example, if a host cell is transformed with a polynucleotide with a nucleotide sequence that does not occur in the untransformed host cell in nature, then that polynucleotide is heterologous (and exogenous) to the host cell. Furthermore, different elements (e.g., promoter, enhancer, coding sequence, terminator, etc.) of a nucleic acid construct (e.g., an expression construct) may be heterologous to one another and/or to the host cell. The term heterologous, as used herein, may also be applied to one or more polynucleotides, polypeptides, or peptides that are identical in sequence to one already present in a host cell, but that are now linked to different additional polynucleotides or peptides (e.g., a tag, marker, reporter, or functional unit) and/or are present at a different copy number, or cellular location or compartment.

As used herein, "codon optimized" refers to a polynucleotide in which the codons have been selected to permit efficient expression of the polypeptide in a particular host organism or host cell. Exemplary host organisms and host cells ("expression hosts") for expressing polypeptides include *E. coli, S. cerevisiae, S. pombe, P. pastoris*, insect cells, plant cells, and cells of the many mammalian cell lines adapted for that purpose (e.g. and without limitation, HeLa, Jurkat, 293, CHO, and COS cells). Model expression hosts for expressing heterologous polypeptides are known in the art, and codon optimized heterologous nucleotide sequences can be deduced from codon usage frequencies of highly expressed polypeptides in such organisms.

Sequence identity: The term "sequence identity" or "identity," as used herein in the context of two polynucleotides, polypeptides, or peptides, refers to the nucleotide sequences or amino acid sequences in the two sequences that are the same when aligned for maximum correspondence over a specified comparison window.

As used herein, the term "percentage of sequence identity" may refer to the value determined by comparing two optimally aligned sequences over a comparison window, wherein the portion of the sequence in the comparison window may comprise additions or deletions (e.g., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, for example, Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, MD), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ program may be employed using the default parameters. Nucleotide or amino acid sequences with increasing similarity to the reference sequences will show increasing percentage identity when assessed by this method.

As used herein with reference to nucleotide sequences, the term "substantially identical" refers to sequences that are more than 85% identical. For example, a substantially identical nucleotide sequence may be at least 85.5%; at least 86%; at least 87%; at least 88%; at least 89%; at least 90%; at least 91%; at least 92%; at least 93%; at least 94%; at least 95%; at least 96%; at least 97%; at least 98%; at least 99%; or at least 99.5% identical to the reference sequence.

As an equivalent of sequence identity, the structural property of "specific hybridization" may be used to define polynucleotides with substantially identical nucleotide sequences. "Specifically hybridizable" indicates the requisite degree of complementarity for sequence-specific stable binding to occur between an oligonucleotide probe and the target polynucleotide defined by the specific binding. A probe oligonucleotide only is specifically hybridizable when non-specific binding of the oligonucleotide to non-target polynucleotides does not occur under appropriate conditions, which are known by those of skill in the art for any probe-target pair.

Hybridization conditions are a function of the composition and length of the hybridizing probe and target polynucleotide, the temperature of hybridization, the ionic strength of the hybridization buffer, and wash conditions. Calculations of hybridization conditions required for assaying specific hybridization are determinable for a particular probe sequence and are known to those of ordinary skill in the art; such calculations are discussed, for example, in Sambrook et al. (ed.) Molecular Cloning: A Laboratory Manual, $2^{nd}$ ed., vol. 1-3, Cold Spring Harbor Laboratory Press, Cold Spring Harbor, NY, 1989, chapters 9 and 11; and Hames and Higgins (eds.) Nucleic Acid Hybridization, IRL Press, Oxford, 1985. Further detailed instruction and guidance with regard to the hybridization of nucleic acids may be found, for example, in Tijssen, "Overview of principles of hybridization and the strategy of nucleic acid probe assays," in Laboratory Techniques in Biochemistry and Molecular Biology—Hybridization with Nucleic Acid Probes, Part I, Chapter 2, Elsevier, NY, 1993; and Ausubel et al., Eds., Current Protocols in Molecular Biology, Chapter 2, Greene Publishing and Wiley-Interscience, NY, 1995.

Specific hybridization may be assayed under "stringent hybridization conditions," of which a generally applicable example is hybridization at 65° C. in 6× saline-sodium citrate (SSC) buffer, 5× Denhardt's solution, 0.5% SDS, and 100 □g sheared salmon testes DNA, followed by 15-30 minute sequential washes at 65° C. in 2× SSC buffer and 0.5% SDS, followed by 1× SSC buffer and 0.5% SDS, and finally 0.2× SSC buffer and 0.5% SDS.

Tag: The term "tag," as used herein, refers to a peptide unit that does not form part of an intermediate peptide or linker sequence produced by the methods herein, though it will be understood that product peptides may themselves contain amino acid motifs that are able to serve a purpose for which conventional "tags" are used; e.g., in affinity purification. In this regard, a tag is a heterogeneous, non-cognate sequence motif with respect to the remainder of the polypeptide in which it is found, and to the concatenated peptides therein. A tag may be covalently linked to the N-terminus, the C-terminus, or at an internal site (e.g., an amino acid side chain) of a polypeptide. A tag can be used to detect, identify, select, enrich or purify the polypeptide to which the tag is covalently linked. In some examples, a tag is a leader peptide translated as part of a polypeptide initially translated in a host cell or system. In some examples, a recombinant polypeptide herein comprises a tag that permits detection, selection, or purification of the polypeptide (an "affinity tag"). Particular affinity tags for use herein include, for example and without limitation, polyhistine (e.g., (His6)), thioredoxin, maltose binding protein, glutathione-S-transferase (GST), HaloTag®, AviTag, Calmodulin-tag, polyglutamate tag, FLAG-tag, HA-tag, Myc-tag, S-tag, SBP-tag, Softag 3, V5 tag, and Xpress tag.

"Recombinant," as used herein, refers to an amino acid sequence or a nucleotide sequence that has been intentionally modified by recombinant methods. By the term "recombinant polynucleotide" herein is meant a polynucleotide (e.g. a nucleic acid molecule), originally formed in vitro, in general, by the manipulation of a nucleic acid by endonucleases, in a form not normally found in nature. Thus, an isolated polynucleotide in a linear form, or an expression vector formed in vitro by ligating DNA molecules that are not normally joined, are both varieties of recombinant polynucleotides. It is understood that once a recombinant nucleic acid molecule is made and introduced into a host cell, it will replicate non-recombinantly; e.g., using the in vivo cellular machinery of the host cell rather than in vitro manipulations. However, such nucleic acids, once produced recombinantly, although subsequently replicated non-recombinantly, are still considered recombinant for the purposes of the disclosure. The terms "recombinant polypeptide" and "recombinant peptide" herein specifically include polypeptides and peptides made using recombinant techniques; e.g., through the expression of a recombinant polynucleotide in a cell or cell-free system containing the necessary components.

The term "vector" refers to a piece of DNA, typically double-stranded, which may have inserted into it a piece of foreign DNA. A vector may be, for example, of plasmid origin. Vectors contain "replicon" polynucleotides that facilitate the autonomous replication of the vector in a host cell. A vector is typically used to transport one or more polynucleotides into a suitable host cell. Once in the host cell, the vector can replicate independently of or coincidentally with the host chromosomal DNA, and several copies of the vector and its inserted polynucleotide(s) can be generated. In addition, the vector may also contain necessary elements that permit transcription of an inserted polynucleotide into an mRNA molecule, or otherwise cause replication of the inserted polynucleotide into multiple copies of RNA. Some expression vectors additionally contain sequence elements adjacent to the inserted polynucleotide that increase the half-life of the expressed mRNA, and/or allow translation of the mRNA into a protein molecule. Many molecules of mRNA and polypeptide encoded by the inserted polynucleotide can thus be rapidly synthesized.

Conservative substitution: As used herein, the term "conservative substitution" refers to a substitution where an amino acid residue is substituted for another amino acid in the same class. A non-conservative amino acid substitution is one where the residues do not fall into the same class, for example, substitution of a basic amino acid for a neutral or non-polar amino acid. Classes of amino acids that may be defined for the purpose of performing a conservative substitution are known in the art. For the purposes of the present disclosure, a peptide may be defined as comprising an amino acid sequence having an amount of sequence identity to a reference amino acid sequence (e.g., at least 90% identical to the reference amino acid sequence). In such cases, it is meant correspondingly that the peptide may comprise an amino acid sequence having the recited sequence identity, wherein the differences between the peptide amino acid sequence and the reference amino acid sequence are conservative substitutions.

In some embodiments, a conservative substitution includes the substitution of a first aliphatic amino acid for a second, different aliphatic amino acid. For example, if a first amino acid is one of Gly; Ala; Pro; Ile; Leu; Val; and Met, the first amino acid may be replaced by a second, different amino acid selected from Gly; Ala; Pro; Ile; Leu; Val; and Met. In particular examples, if a first amino acid is one of Gly; Ala; Pro; Ile; Leu; and Val, the first amino acid may be replaced by a second, different amino acid selected from Gly; Ala; Pro; Ile; Leu; and Val. In particular examples involving the substitution of hydrophobic aliphatic amino acids, if a first amino acid is one of Ala; Pro; Ile; Leu; and Val, the first amino acid may be replaced by a second, different amino acid selected from Ala; Pro; Ile; Leu; and Val.

In some embodiments, a conservative substitution includes the substitution of a first aromatic amino acid for a second, different aromatic amino acid. For example, if a first amino acid is one of His; Phe; Trp; and Tyr, the first amino acid may be replaced by a second, different amino acid selected from His; Phe; Trp; and Tyr. In particular examples involving the substitution of uncharged aromatic amino acids, if a first amino acid is one of Phe; Trp; and Tyr, the first amino acid may be replaced by a second, different amino acid selected from Phe; Trp; and Tyr.

In some embodiments, a conservative substitution includes the substitution of a first hydrophobic amino acid for a second, different hydrophobic amino acid. For example, if a first amino acid is one of Ala; Val; Ile; Leu; Met; Phe; Tyr; and Trp, the first amino acid may be replaced by a second, different amino acid selected from Ala; Val; Ile; Leu; Met; Phe; Tyr; and Trp. In particular examples involving the substitution of non-aromatic, hydrophobic amino acids, if a first amino acid is one of Ala; Val; Ile; Leu; and Met, the first amino acid may be replaced by a second, different amino acid selected from Ala; Val; Ile; Leu; and Met.

In some embodiments, a conservative substitution includes the substitution of a first polar amino acid for a second, different polar amino acid. For example, if a first amino acid is one of Ser; Thr; Asn; Gln; Cys; Gly; Pro; Arg; His; Lys; Asp; and Glu, the first amino acid may be replaced by a second, different amino acid selected from Ser; Thr; Asn; Gln; Cys; Gly; Pro; Arg; His; Lys; Asp; and Glu. In particular examples involving the substitution of uncharged, polar amino acids, if a first amino acid is one of Ser; Thr; Asn; Gln; Cys; Gly; and Pro, the first amino acid may be replaced by a second, different amino acid selected from Ser; Thr; Asn; Gln; Cys; Gly; and Pro. In particular examples involving the substitution of charged, polar amino acids, if a first amino acid is one of His; Arg; Lys; Asp; and Glu, the first amino acid may be replaced by a second, different amino acid selected from His; Arg; Lys; Asp; and Glu. In further examples involving the substitution of charged, polar amino acids, if a first amino acid is one of Arg; Lys; Asp; and Glu, the first amino acid may be replaced by a second, different amino acid selected from Arg; Lys; Asp; and Glu. In particular examples involving the substitution of positively charged (basic), polar amino acids, if a first amino acid is one of His; Arg; and Lys, the first amino acid may be replaced by a second, different amino acid selected from His; Arg; and Lys. In further examples involving the substitution of positively charged, polar amino acids, if a first amino acid is Arg or Lys, the first amino acid may be replaced by the other amino acid of Arg and Lys. In particular examples involving the substitution of negatively charged (acidic), polar amino acids, if a first amino acid is Asp or Glu, the first amino acid may be replaced by the other amino acid of Asp and Glu.

In some embodiments, a conservative substitution includes the substitution of a first electrically neutral amino acid for a second, different electrically neutral amino acid. For example, if a first amino acid is one of Gly; Ser; Thr; Cys; Asn; Gln; and Tyr, the first amino acid may be replaced by a second, different amino acid selected from Gly; Ser; Thr; Cys; Asn; Gln; and Tyr.

In some embodiments, a conservative substitution includes the substitution of a first non-polar amino acid for a second, different non-polar amino acid. For example, if a first amino acid is one of Ala; Val; Leu; Ile; Phe; Trp; Pro; and Met, the first amino acid may be replaced by a second, different amino acid selected from Ala; Val; Leu; Ile; Phe; Trp; Pro; and Met.

In many examples, the selection of a particular second amino acid to be used in a conservative substitution to replace a first amino acid may be made in order to maximize the number of the foregoing classes to which the first and second amino acids both belong. Thus, if the first amino acid is Ser (a polar, non-aromatic, and electrically neutral amino acid), the second amino acid may be another polar amino acid (e.g., Thr; Asn; Gln; Cys; Gly; Pro; Arg; His; Lys; Asp; or Glu); another non-aromatic amino acid (e.g., Thr; Asn; Gln; Cys; Gly; Pro; Arg; His; Lys; Asp; Glu; Ala; Ile; Leu; Val; or Met); or another electrically-neutral amino acid (e.g., Gly; Thr; Cys; Asn; Gln; or Tyr). However, it may be preferred that the second amino acid in this case be one of Thr; Asn; Gln; Cys; and Gly, because these amino acids share all the classifications according to polarity, non-aromaticity, and electrical neutrality. Additional criteria that may optionally be used to select a particular second amino acid to be used in a conservative substitution are known in the art. For example, when Thr; Asn; Gln; Cys; and Gly are available to be used in a conservative substitution for Ser, Cys may be eliminated from selection in order to avoid the formation of undesirable cross-linkages and/or disulfide bonds. Likewise, Gly may be eliminate from selection, because it lacks an alkyl side chain. In this case, Thr may be selected, for example, in order to retain the functionality of a side chain hydroxyl group. The selection of the particular second amino acid to be used in a conservative substitution is ultimately, however, within the discretion of the skilled practitioner Reaction mixture: As used herein, the term "reaction mixture" refers to an in vitro aqueous volume comprising salts, co-factors, and/or other components that are sufficient for an enzymatic and/or chemical activity that modifies a substrate. The term specifically includes the contents of a bioreactor, cell lysate, or cell-free system where a particular reaction or set of reactions is to occur; e.g., the proteolytic cleavage of a recombinant polypeptide (e.g., a soluble polypeptide) and/or the subsequent enzymatic and/or chemical removal of extraneous amino acids from an intermediate peptide to yield a product peptide. The contents of bioreactors and other vessels containing a reaction mixture may be exchanged during a reaction or multi-step reaction as known in the art; e.g., to replace exhausted reagents or slow or stop a particular reaction, or to initiate a different reaction.

MALDI-TOF: The term "MALDI" refers to Matrix-Assisted Laser Desorption/Ionization, a process wherein analyte is embedded in a solid or crystalline "matrix" of light-absorbing molecules (e.g., nicotinic, sinapinic, or 3-hydroxypicolinic acid), then desorbed by laser irradiation and ionized from the solid phase into the gaseous or vapor phase, and accelerated as intact molecular ions towards a detector. The "matrix" is typically a small organic acid mixed in solution with the analyte in a 10,000:1 molar ratio of matrix/analyte. The matrix solution can be adjusted to neutral pH before use.

The term "MALDI-TOF MS" refers to Matrix-Assisted Laser Desorption/Ionization Time-of-Flight mass spectrometry.

Liquid chromatography. The term "liquid chromatography" or "LC" refers to a process of selective separation of one or more components of a fluid solution as the fluid uniformly percolates through a column of a finely divided substance, or through capillary passageways. The selective separation results from the distribution of the components of the mixture between one or more stationary phases and the bulk fluid, (e.g., mobile phase), as this fluid moves relative to the stationary phase(s). Examples of "liquid chromatography" include high performance liquid chromatography (HPLC).

High performance liquid chromatography: The term "high performance liquid chromatography" ("HPLC") refers to liquid chromatography in which the degree of separation is increased by forcing the mobile phase under pressure through a stationary phase, typically a densely packed column. Those skilled in the art will understand that separation in such columns is a partition process and may select LC, including HPLC, instruments and columns that are suitable for use.

Real-time PCR. The term "real-time PCR" ("RT PCR") is used to denote a subset of quantitative PCR techniques that allow for detection of PCR product throughout the PCR reaction, or in real time. The principles of real-time PCR are generally described, for example, in Held et al. "Real Time Quantitative PCR" Genome Research 6:986-994 (1996). Generally, real-time PCR measures a signal at each amplification cycle. Some real-time PCR techniques rely on fluorophores that emit a signal at the completion of every multiplication cycle. Examples of such fluorophores are fluorescence dyes that emit fluorescence at a defined wavelength upon binding to double-stranded DNA, such as SYBR green. An increase in double-stranded DNA during each amplification cycle thus leads to an increase in fluorescence intensity due to accumulation of PCR product.

(ii) Sequences and Agents of the Application

The nucleic acid sequences listed in the accompanying sequence listing are shown using standard letter abbreviations for nucleotide bases. Only one strand of each nucleic acid sequence is shown, but the complementary strand is understood to be included by any reference to the displayed strand. In the accompanying sequence listing:

SEQ ID NOs: 1-29 show representative recognition sequences of proteases that cleave a polypeptide after two or four basic residues, used in particular embodiments to release intermediate peptides.

SEQ ID NOs: 30-45 show representative recognition sequences of proteases that leave no amino acid at the P1' position following cleavage of a polypeptide, used in particular embodiments to release intermediate peptides.

SEQ ID NOs: 46-56 show representative chemical cleavage sequences, used in particular embodiments to release product peptides with a target amino acid sequence from an intermediate peptide.

SEQ ID NOs: 57-83 show representative linker sequences, used in particular embodiments, for example, to improve reaction efficiency.

SEQ ID NOs: 84-121 show target amino acid sequences of representative product peptides that are producible utilizing the compositions and methods herein. SEQ ID NOs: 84-109 show target amino acid sequences of representative product peptides that comprise a Cys and/or Met residue, rendering the peptides unsuitable for certain methods in the art that rely on the introduction of a heterologous cysteine at the amino-terminus and a methionine at the carboxy-terminus of a linker peptide.

SEQ ID NOs: 122-124, 195 show representative sequences of peptide tags that are comprised within certain recombinant polypeptides herein.

SEQ ID NOs: 125-173, 189-194, 196-199, 201-202 show examples of recombinant polypeptides comprising target amino acid sequences of certain product peptides, and amino acid sequences comprised within the polypeptides that are removed to release the product peptides.

Figure 4:
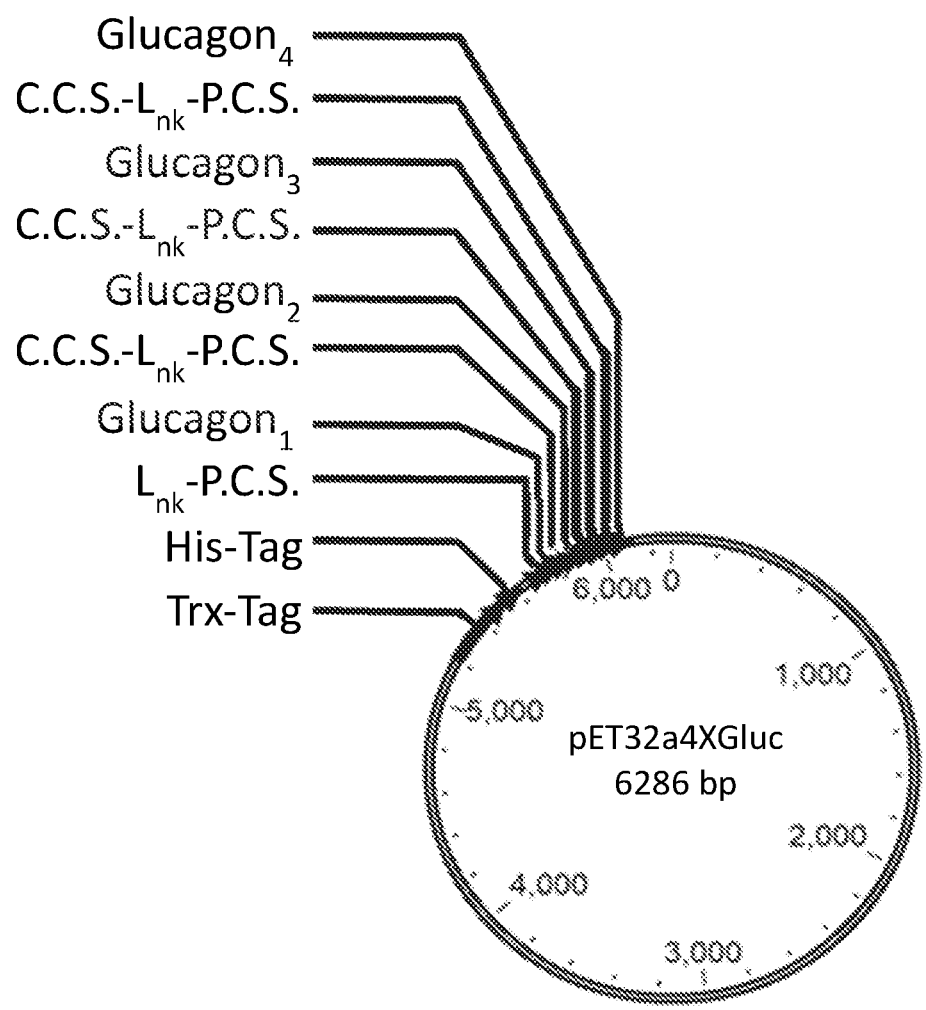
FIG. 4 shows a plasmid diagram of pET32a, containing an expression cassette encoding a recombinant polypeptide comprising tandem repeating units comprising a glucagon product peptide.

SEQ ID NOs: 174 shows the sequence of the plasmid diagram of FIG. 4.

SEQ ID NOs: 175-188, 200 show representative recognition sequences of retroviral proteases, used in particular embodiments to release intermediate peptides or product peptides with a target amino acid sequence from an intermediate peptide.

(iii) Uses

Cleavage of fusion proteins to obtain a polypeptide or peptide of interest can in principle be achieved by chemical or biochemical methods, such as enzymatic cleavage using proteolytic enzymes (proteases). These methods employ agents that act by hydrolysis of peptide bonds, and the specificity of the cleavage agent is determined by the identity of the amino acid residue at or near the peptide bond which is cleaved. Non-specific cleavage may adversely affect use of a polypeptide or peptide of interest, for example, by affecting the activity of the polypeptide or peptide, or by contaminating the product with fragments representing off-target cleavage events. Therefore, enzymatic cleavage of fusion polypeptides is limited due to the fact that a cleavage site may occur in the polypeptide or peptide of interest itself. Inefficient or incomplete cleavage of a fusion protein may also occur, reducing yield and introducing heterogeneity to the product such that only a small fraction of the desired protein is purified. Therefore, while a polypeptide or peptide production platform using one family of proteases may be suitable for one or several products, it cannot be adapted for the production of other polypeptides or peptides without modification.

The compositions and methods herein address a further problem that is associated with peptide production; extraneous amino acids are attached to the cleaved desired peptide by conventional methods. These amino acids are typically present when a linker sequence connecting desired peptide products is cleaved. These amino acids often affect the properties of the resulting peptide and/or present regulatory difficulties for use, particularly when the peptide is intended for use in human subjects. The compositions and methods herein are useful for obtaining the benefits associated with recombinant expression of peptides in fusion polypeptides containing multiple peptides (e.g., increased yield) without resulting in extraneous amino acids in the desired peptide product. To achieve these results, embodiments herein provide peptide concatemers with enzymatically cleavable linker sequences comprising elements arranged in a particular manner.

In some embodiments, a concatemer comprises the recognition site of a protease that cleaves after two or four basic residues ($B_m$), a linker sequence ($L_{nk}$), a desired peptide product (DP), a next two or four basic residue protease recognition site ($B_m$), and a further desired peptide product (DP), and may further comprise at least one peptide unit that does not form part of the desired peptides or proteins or linker sequences; e.g., a TAG that facilitates purification, solubilization, or both. A concatemer in such embodiments comprises these elements in the arrangement:

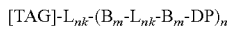
[TAG]-$L_{nk}$-($B_m$-$L_{nk}$-$B_m$-DP)$_n$ or

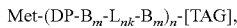
Met-(DP-$B_m$-$L_{nk}$-$B_m$)$_n$-[TAG], wherein the number of repeats "n" is within the discretion of the practitioner, and depends on the length of the particular desired peptide product and the fusion protein expression system.

Following proteolytic cleavage of the concatemer polypeptide with a protease that cleaves after two or four basic residues (e.g., Furin, Protein convertase, Neuroendocrine convertase 1, or Kexin), DP-$B_m$ and DP are produced (with an additional Met-DP, depending on the position of a TAG if one is employed), as well as TAG-$B_m$ and $L_{nk}$-$B_m$ products that do not contain DP. The resulting products are treated with a carboxypeptidase (e.g., Carboxypeptidase N, Carboxypeptidase B, Carboxypeptidase U, or metallocarboxypeptidase D), thereby converting DP-$B_m$ to DP, without extraneous amino acids. In examples utilizing particular expression hosts (e.g., E. coli), an initial methionine residue is removed from the recombinant polypeptide, which may be useful in applications utilizing a TAG at the C-terminus of the concatemer.

In the foregoing and further embodiments, a concatemer comprises a recognition site for a protease that recognizes a specific target amino acid sequence and leaves no amino acid at the P1' position following cleavage, a desired peptide product (DP), and a linker sequence and chemical cleavage sequence (C.C.S.-$L_{nk}$), and may further comprise at least one peptide unit that does not form part of the desired peptides or proteins or linker sequences (e.g., a TAG). A concatemer in such embodiments comprises these elements in the arrangement:

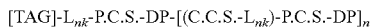
[TAG]-$L_{nk}$-P.C.S.-DP-[(C.C.S.-$L_{nk}$)-P.C.S.-DP]$_n$ or

Met-DP-[(C.C.S.-$L_{nk}$)-P.C.S.-DP]$_n$-C.C.S.-[TAG], wherein the number of repeats "n" is within the discretion of the practitioner, and depends on the length of the particular desired peptide product and the fusion protein expression system.

Following proteolytic cleavage of the concatemer polypeptide with a protease that leaves no amino acid at the P1' position following cleavage (e.g., Enterokinase, blood coagulation factor X (Factor Xa), a caspase, or Granzyme B), Met-DP-(C.C.S.-$L_{nk}$-P.C.S.) and DP-(C.C.S.-$L_{nk}$-P.C.S.) are produced. In examples utilizing particular expression hosts (e.g., E. coli), the initial methionine is removed from the Met-DP-C.C.S.-P.C.S. peptide, yielding only DP-(C.C.S.-$L_{nk}$-P.C.S.). The products are then treated with an appropriate site-specific proteolytic chemical agent (e.g., 2-nitro-5-thiocyanobenzoic acid (NTCB), $Ni^{2+}$, or $Pd^{2+}$), thereby converting DP-(C.C.S.-$L_{nk}$-P.C.S.) to the desired peptide product, without extraneous amino acids that are not part of the target amino acid sequence.

Consistent with the foregoing, embodiments of the present disclosure provide recombinant polypeptides comprising concatenated intermediate peptides and intervening linker sequences comprising cleavage sites of particular proteases, and polynucleotides encoding the same. In particular embodiments, the recombinant polypeptides are soluble in an aqueous environment; e.g., such that they do not form inclusion bodies in a recombinant production cell. The proteases catalyze the sequence-specific cleavage of the polypeptides into the intermediate peptides, which are subsequently enzymatically or chemically processed into product peptides consisting of a desired target sequence; e.g., the target amino acid sequence without any extraneous amino acids. The foregoing polypeptides comprise in particular examples 1-150 concatenated peptide units (e.g. and without limitation, 2-150, 3-150, 2-10, 2-20, 3-20, 2-10, or 3-10), the choice of which is according to the discretion of the practitioner, and may depend on factors such as the length of the peptide and the particular host or expression system employed. Particular polypeptides may comprise intermediate peptides comprising the same product peptide, or they may comprise several species of intermediate peptides with different product peptides, arranged in the polypeptide as hereinafter described.

In a first aspect, the protease that catalyze the sequence-specific cleavage of the recombinant polypeptide into intermediate peptides cleaves after two or four basic amino acid residues (K or L), and the intermediate peptides comprise the product peptide and the two or four basic amino acids remaining after the proteolysis reaction. Examples of proteases with two or four basic amino acid residue recognition sites that may be used in embodiments herein include example, Protein Convertases with the general recognition site of [R/K]$X_n$[R/K]↓, in which n is 0 or 2 or 4 or 6 (e.g., SEQ ID NO: 1 and SEQ ID NOs: 27-29) (a preferred sequence is RX[R/K]R↓ (SEQ ID NO: 14), in which X is preferably a basic residue), Furin (recognition site RX[R/K]R↓ (SEQ ID NO: 14)), Neuroendocrine Convertase 1 (recognition site (R/K)R↓ (SEQ ID NO: 2)), and Kexin (recognition site (R/K)R↓ (SEQ ID NO: 2)). In particular examples, therefore, the recombinant polypeptide may comprise a protease recognition site comprising an amino acid sequence selected from the group consisting of RR (SEQ ID NO: 3) (Kexin; Neuroendocrine Convertase 1), KR (SEQ ID NO: 4) (Kexin; Neuroendocrine Convertase 1), [R/K][R/K][R/K]R (SEQ ID NO: 17) (Kexin; Neuroendocrine Convertase 1; Protein Convertase), R[R/K][R/K]R (SEQ ID NO: 18) (Kexin; Neuroendocrine Convertase 1; Furin; Protein Convertase), RRRR (SEQ ID NO: 19) (Kexin; Neuroendocrine Convertase 1; Furin; Protein Convertase), RKRR (SEQ ID NO: 20) (Kexin; Neuroendocrine Convertase 1; Furin; Protein Convertase), RRKR (SEQ ID NO: 21) (Kexin; Neuroendocrine Convertase 1; Furin; Protein Convertase), RKKR (SEQ ID NO: 22) (Kexin; Neuroendocrine Convertase 1; Furin; Protein Convertase), KRRR (SEQ ID NO: 23) (Kexin; Neuroendocrine Convertase 1; Protein Convertase), KKRR (SEQ ID NO: 24) (Kexin; Neuroendocrine Convertase 1; Protein Convertase), KRKR (SEQ ID NO: 25) (Kexin; Neuroendocrine Convertase 1; Protein Convertase), and KKKR (SEQ ID NO: 26) (Kexin; Neuroendocrine Convertase 1; Protein Convertase).

In a second aspect, the protease that catalyzes the sequence-specific cleavage of the recombinant polypeptide into intermediate peptides leaves no amino acid at the P1' position following cleavage, and the intermediate peptides comprise the product peptide and a linker sequence and sequence-specific chemical cleavage site. Examples of proteases that cleave polypeptides without leaving an amino acid at the P1' position that may be used in embodiments herein include example, the proteases listed in Table 1.

TABLE 1

Proteases that Leave No Amino Acid at the P1' Position Following Cleavage

| Protease | Recognition Site* | Sequence Number |
|---|---|---|
| No P1' AA Protease Recognition Site: SEQ ID NO: 30 | | |
| Enterokinase | DDDDK↓ | 31 |
| Caspase Recognition Site: SEQ ID NO: 32 | | |
| Caspase-2, -3, -7, CED-3 | DEXD↓ | 33 |
| Caspase-1, -4, -5 | (Y/F/W)VXD↓ | 35 |
| Caspase-6, -8, -9, and Granzyme B | (I/L/TA/)EXD↓ | 39 |
| Factor Xa Recognition Site: SEQ ID NO: 43 | | |
| Factor Xa | I(E/D)GR↓ | 43 |

*Amino acids immediately preceding cleavage site (e.g., P4-P3-P2-P1↓, P5-P4-P3-P2-P1↓, etc.)

In particular examples, therefore, the recombinant polypeptide may comprise the protease recognition site of SEQ ID NO: 30. For example, the recombinant polypeptide may comprise a protease recognition site comprising an amino acid sequence selected from the group consisting of SEQ ID NOs: 31-45 (e.g., any of SEQ ID NO: 31, SEQ ID NO: 34, SEQ ID NO: 36, SEQ ID NO: 37, SEQ ID NO: 38, SEQ ID NO: 40, SEQ ID NO: 41, SEQ ID NO: 44, and SEQ ID NO: 45). For example, a recombinant polypeptide for proteolysis by Enterokinase may comprise SEQ ID NO: 31. By way of further example, a recombinant polypeptide for proteolysis by a caspase may comprise SEQ ID NO: 32. In specific examples, a recombinant polypeptide for proteolysis by Caspase-2, Caspase-3, Caspase-7, or CED-3 may comprise SEQ ID NO: 33, e.g., a polypeptide comprising SEQ ID NO: 34; a recombinant polypeptide for proteolysis by Caspase-1, Caspase-4, or Caspase-5 may comprise SEQ ID NO: 35, e.g., a polypeptide comprising SEQ ID NO: 36, SEQ ID NO: 37, or SEQ ID NO: 38; and a recombinant polypeptide for proteolysis by Caspase-6, Caspase-8, Caspase-9, or Granzyme B may comprise SEQ ID NO: 39, e.g., a polypeptide comprising SEQ ID NO: 40, SEQ ID NO: 41, or SEQ ID NO: 42. In even further examples, a recombinant polypeptide for proteolysis by Factor Xa may comprise SEQ ID NO: 43 (e.g., SEQ ID NO: 44 or SEQ ID NO: 45).

Principles demonstrated by the foregoing first and second aspects may be utilized in some embodiments of the invention. In particular examples, a protease that cleaves after two or four basic residues or a protease that leaves no amino acid at the P1' position following cleavage may be utilized with an aminopeptidase. This example is described herein with reference to Aminopeptidase P as an example of an aminopeptidase. A recombinant polypeptide for production of a desired peptide product through proteolysis by a protease that cleaves after two or four basic residues and Aminopeptidase P may comprise elements in the arrangement:

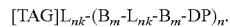

Each of the foregoing aspects may be combined in a single recombinant polypeptide, such that both types of intermediate peptides may be produced by the respective protease activities. In embodiments herein, the recombinant polypeptide comprises a plurality of protease cleavage sites selected from the group consisting of SEQ ID NOs: 1-45.

According to the first aspect, a recombinant polypeptide comprises elements in the order DP-[$B_m$-$L_{nk}$-$B_m$-DP]$_n$, where $B_m$ represents the two or four basic amino acid recognition site, $L_{nk}$ represents a linker sequence of 0-50 amino acids in length, and DP represents the product peptide target sequence. The recombinant polypeptide may further comprise at least one peptide unit in addition to the foregoing; e.g., a tag that facilitates purification or solubilization, or a targeting peptide. The recombinant polypeptide may also comprise an N-terminal methionine residue preceding a first product peptide. Proteolysis of the polypeptide after the two or four basic amino acid recognition site produces the intermediate peptide, DP-$B_m$. Recognition sites according to the first aspect comprise SEQ ID NO: 1; e.g., the recognition site may comprise an amino acid sequence selected from the group consisting of SEQ ID NOs: 2-29. Recognition sites used in particular examples include SEQ ID NO: 3, SEQ ID NO: 4, SEQ ID NO: 15, SEQ ID NO: 16, and SEQ ID NOs: 19-26. These intermediate peptides (DP-$B_m$) may be subjected to carboxypeptidase activity to remove the two or four basic amino acid recognition site residues, thereby producing the product peptide consisting of its target sequence without extraneous amino acids. Examples of carboxypeptidases that may be utilized in particular embodiments to remove the two or four basic amino acid recognition site residues include Carboxypeptidase N, Carboxypeptidase B, Carboxypeptidase U, and metallocarboxypeptidase D.

According to the second aspect, a polypeptide comprises elements in the order DP-[(C.C.S.-$L_{nk}$)-P.C.S.-DP]$_n$, where C.C.S.-$L_{nk}$ represents a linker sequence of 0-50 amino acids in length comprising a chemical cleavage sequence, P.C.S. represents the recognition site for a protease that leaves no P1' amino acid residue in the cleavage product, and DP represents the product peptide. Recombinant polypeptides according to this second aspect may also further comprise at least one peptide unit in addition to the foregoing, and may likewise also comprise an N-terminal methionine residue preceding a first desired peptide product. Proteolysis of the polypeptide protease that leaves no P1' amino acid residue in the cleavage product produces the intermediate peptide, DP-(CSS-$L_{nk}$-P.C.S.). The intermediate peptides may then be subjected to the appropriate chemical cleavage agent (e.g., NTCB, $Ni^{2+}$, or $Pd^{2+}$) to remove the C-terminal linker sequence, thereby producing the desired product peptide without extraneous amino acids.

It is known that $Ni^{2+}$ cleaves at the N-terminal side of SXH, however it has been reported that a Gly at $P_1$ position prior to the Ser residue is critical for high cleavage efficiency, as described, for example, in Dang et el. (2019) Nat Methods 16(4):320. In particular examples, larger amino acids, e.g., Phe at $P_1$ in Teriparatide, also enable high cleavage efficiency.

Intermediate peptides according to the second aspect may comprise a chemical cleavage sequence selected from the group consisting of SEQ ID NO: 46 (NTCB cleavage site); SEQ ID NO: 49, wherein P1' is Pro at neutral to acidic pH, but can be Gly at pH=2 ($Pd^{2+}$ cleavage site); and SEQ ID NO: 53, wherein P2' and P4' are preferably bulky/hydrophobic, and P2' is not Pro ($Ni^{2+}$ recognition site). For example, a NTCB cleavage site may comprise an amino acid sequence selected from the group consisting of SEQ ID NO: 47 and SEQ ID NO: 48, a $Pd^{2+}$ cleavage site may comprise an amino acid sequence selected from the group consisting of SEQ ID NOs: 50-52, and a $Ni^{2+}$ cleavage site may comprise an amino acid sequence selected from the group consisting of SEQ ID NOs: 54-56. Chemical cleavage sites used in particular examples include SEQ ID NO: 47, SEQ ID NO: 48, SEQ ID NO: 50, SEQ ID NO: 51, SEQ ID NO: 54, and SEQ ID NOs: 56.

Therefore, a recombinant polypeptide comprising concatenated units comprising product peptides is defined by an amino acid sequence that depends in particular embodiments on the choice of the first protease (e.g., a protease that has a two or four basic amino acid recognition site, or a protease that leaves no P1' amino acid in the cleavage product) and the carboxypeptidase or chemical cleavage agent in the concatenated units.

In particular examples, a recombinant polypeptide comprising units according to the first aspect comprises the amino acid sequence, [product peptide$_n$]-[(SEQ ID NO: 1)-L$_{nk}$-(SEQ ID NO: 1)]-[product peptide$_{n+1}$], where n corresponds to the position of the unit in the polypeptide (e.g., if the third and fourth product peptide in the polypeptide are separated by (SEQ ID NO: 1)-L$_{nk}$-(SEQ ID NO: 1), n=3 and n+1=4. In specific examples of recombinant polypeptides comprising units according to the first aspect utilizing Kexin, Neuroendocrine Convertase 1, Furin, or a Protein Convertase as a protease that has a 2 or 4 basic amino acid recognition site, the recombinant polypeptide may, for example, comprise: [product peptide]-[(SEQ ID NO: 18)-L$_{nk}$-(SEQ ID NO: 18)]-[product peptide].

In particular examples, a recombinant polypeptide comprising units according to the second aspect may comprise, for example, [product peptide$_n$]-C.C.S.-L$_{nk}$-P.C.S.-[product peptide$_{n+1}$], where C.C.S. comprises SEQ ID NO: 46, SEQ ID NO: 49, or SEQ ID NO: 53, and P.C.S. is SEQ ID NO: 30. In specific examples of recombinant polypeptides comprising units according to the second aspect utilizing Caspase-3 or Caspase-7 as a protease that leaves no P1' amino acid residue in the cleavage product, the recombinant polypeptide may, for example, comprise at least one of the following amino acid sequences: [product peptide$_n$]-[((SEQ ID NO: 46)↓L$_{nk}$)-(SEQ ID NO: 33)-product peptide$_{n+1}$] (for chemical cleavage with NTCB); [product peptide$_n$]-[(↓(SEQ ID NO: 49)-L$_{nk}$)-(SEQ ID NO: 33)-product peptide$_{n+1}$] (for chemical cleavage with $Pd^{2+}$); and [product peptide$_n$]-[(↓(SEQ ID NO: 53)-L$_{nk}$)-(SEQ ID NO: 33)-product peptide$_{n+1}$] (for chemical cleavage with $Ni^{2+}$). P.C.S. in the foregoing examples utilizing Caspase-3 or Caspase-7 as a protease that leaves no P1' amino acid residue in the cleavage product may be SEQ ID NO: 34. In the foregoing examples, substitution of the cleavage site of a different protease that leaves no P1' amino acid in the cleavage product adapts the polypeptide for an application using the different protease. Recombinant polypeptides herein may comprise different combinations of the foregoing elements; e.g., comprising cleavage sites of the same class of proteases (e.g., different cleavage sites of the same protease), or comprising cleavage sites for different proteases (e.g., to separately release different product peptides). Furthermore, product peptides comprised within the concatenated units of the polypeptide may be the same peptide in particular embodiments, but the concatenated units may comprise different product peptides in others.

Linker sequences utilized in embodiments herein may comprise any number of amino acids between 0 and 50. Therefore, in certain examples, the linker sequence comprises 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41, 42, 43, 44, 45, 46, 47, 48, 49, or 50 amino acids. In specific examples, a linker sequence may be 1 or 2 amino acids in length. In particular embodiments, the linker sequence comprises small amino acids (e.g., Ala, Ser, Gly, and polyglycine), for example, to increase the exposure of the recognition site to the protease, and/or to reduce the likelihood of disulfide formation between cysteines. For example, in the case of Cys for NTCB cleavage, the presence of Gly in a linker sequence and Cys for NTCB cleavage reduces disulfide bond formation in addition to improving the exposure to the proteolytic cleavage site, thus making the recombinant polypeptide more amenable to NTCB cleavage. Therefore, we can say any amino acid but more preferable glycine and preferably serine or Ala. However, the presence of Ala, Ser, and Gly is not required in some embodiments. For many applications, Ala, Ser, and Gly are preferred for most proteases because of increased exposure but it is not mandatory. Therefore, in particular embodiments, the linker sequence may comprise any amino acids, and preferably comprises Gly, Ser, and/or Ala, more preferably comprising Gly. Examples of linker sequences useful in embodiments herein include SEQ ID NOs: 57-83 and SEQ ID NO: 123. Specific examples herein include a linker sequence selected from the group consisting of Gly, SEQ ID NO: 61, SEQ ID NO: 62, SEQ ID NO: 82, SEQ ID NO: 83, SEQ ID NO: 74, and SEQ ID NO: 123.

In some embodiments, the linker sequences of the concatenated units are the same. However, in further examples, the linker sequences are different. It will be understood that the specific identity of the amino acids in the linker sequence is not an essential aspect with regard to the general description of embodiments herein, other than particular requirements of particular applications, as is known and within the discretion of the practitioner.

Illustrative and non-limiting examples of amino acid sequences comprised in linker sequences that are useful in certain embodiments herein include: $G_nS_m$, where n=1-4 and m=1-4 (e.g., [GGGGS (SEQ ID NO: 67)]$_n$); KESGSVSSE-QLAQFRSLD (SEQ ID NO: 77); EGKSSGSGSESKST (SEQ ID NO: 78); GSAGSAAGSGE(F/G) (SEQ ID NO: 79), e.g., GSAGSAAGSGEF (SEQ ID NO: 80) or GSAGSAAGSGEG (SEQ ID NO: 81); A(EAAAK)$_n$A (e.g., a linker sequence comprising EAAAKA (SEQ ID NO: 75) and AEAAAK (SEQ ID NO: 76)); and (X/P)$_n$(S/G), e.g., P(S/G) (SEQ ID NO: 68), PS (SEQ ID NO: 57), PG (SEQ ID NO: 58), PP(S/G) (SEQ ID NO: 72), PX(S/G) (SEQ ID NO: 70), (S/G) (SEQ ID NO: 71), Gly, Ser, PP(S/G) (SEQ ID NO: 72), (A/K/E)(S/G) (SEQ ID NO: 73), AS (SEQ ID NO: 59), AG (SEQ ID NO: 60), KS (SEQ ID NO: 63), KG (SEQ ID NO: 64), ES (SEQ ID NO: 65), or EG (SEQ ID NO: 66).

Linker sequences having one or more charged residues may contribute the accessibility of the cleavage sequences thereby eliminating the need for a denaturing agent thereby removing any denaturing effect on the proteolytic enzymes utilized in a product peptide procedure. Alternatively, the linker and the cleavage sequences used in peptide production collectively may have at least one charged residue and one polar residue in order to maintain accessibility of the cleavage sites without the use of denaturants. In some embodiments, the linker may have small amino acids such as glycine between the cleavage sequences wherein the cleavage sequences have at least one charged residue and one polar residue.

A product peptide comprised within a concatenated unit of a recombinant polypeptide according to embodiments herein may be any peptide of interest. In particular embodiments, the product peptide comprises biological activity and has a direct or indirect effect on an organism or microorganism. For example, specific product peptides may have peptide hormone activity and/or receptor binding activity, protein or receptor modification activity, or may prevent activation, inhibition, or modification of a receptor or protein by another molecule. In some examples, a product peptide has a direct or indirect effect on a metabolic syndrome (e.g., modulating cholesterol levels, blood pressure levels, insulin levels, mood, satiety, and/or metabolic diseases and/or biological activity relevant for personal care or therapeutic applications.

A product peptide may have any size, but typically comprises less than 1500 amino acids; e.g., less than 1000 amino acids, less than 800 amino acids, less than 700 amino acids, less than 600 amino acids, less than 500 amino acids, less than 400 amino acids, less than 300 amino acids, less than 250 amino acids, less than 200 amino acids, less than 150 amino acids, even less than 140 amino acids, less than 130 amino acids, less than 120 amino acids, less than 110 amino acids, less than 100 amino acids, less than 90 amino acids, less than 80 amino acids, less than 70 amino acids, less than 60 amino acids, or less than or equal to 50 amino acids. In specific examples, the product peptide has less than 50 amino acids; e.g., 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 or less amino acids. In particular embodiments, the product peptide comprises at least one methionine residue, at least one cysteine residue, or at least one of both methionine and cysteine residues; such peptides are not able to be efficiently produced by certain methods of peptide production from tandem repeats utilizing the introduction of an N-terminal cysteine and C-terminal methionine in a linker peptide.

Representative peptides that may be produced utilizing the compositions and methods herein include Glucagon, Exenatide, Sermorelin, Nesiritide (Natriuretic peptide B), Teduglutide, [Cys(Acm)20,31] Epidermal Growth Factor (20-31), ACE2 a1 Helix Sequence, T1 Peptide, GTP-binding Protein Fragment, G☐, L-selectin peptide, Peptide Standard 1, ACTH (1-39) (Acthar), ACTH (1-24), Sinapultide (KL4), Teduglutide, Thymalfasin, Apolipoprotein B Synthetic Peptide, Galanin, Tau Peptide (45-73) (Exon 2/Insert 1 domain), Lepirudin, Pramlinitide, Calcitonin, Cystatins, Somatostatin, Megainin 1, Megainin 2, Corticotropin, Teriparatide, Tesamorelin, Aprotinin, Bivalirudin, Enfuvirtide, Secretin, Gramicidin D, Glatiramer, Vasopressin, and Oxytocin.

As previously indicated, a recombinant polypeptide herein may further comprise at least one peptide unit that does not form part of an intermediate peptide products; e.g., on the N-terminal or C-terminal end of the polypeptide, or in a linker sequence (e.g., a His$_6$ tag in a linker sequence to provide flexibility for the production and/or purification process). Referred to herein as "tags," such peptide units may impart or increase any one or more desired function on the recombinant polypeptide; e.g., detection, purification, solubilization, protection from degradation, proper folding (chaperone activity), post-translational modification, N-terminal or C-terminal capping (capping units preferably are more hydrophilic than the rest of the protein and consequently shield the hydrophobic part to increase solubility (Kohl et al. (2003) Proc. Natl. Acad. Sci U.S.A. 100:1700-5)), receptor activity, signaling activity, secretion, and targeting. In particular examples, the recombinant polypeptide comprises a tag that facilitates purification (e.g., affinity purification) and/or solubilization of the polypeptide. In applications wherein the recombinant polypeptide is to be secreted from the host cell, an appropriate signal peptide may be added to the polypeptide in order to direct the synthesized polypeptide to the secretion route of the host cell. Such signal peptides are known in the art, and heterologous signal peptides and signal peptides native to the host cell may generally be utilized. Non-limiting examples of the foregoing peptide tags are well known and commonly used in the art; e.g., thioredoxin (TrxA), His$_6$, myc, T7, HSV, V5, HA, FLAG, strep-tags, GFP, chitin binding protein, GST, MBT, NusA, IF2, cellulose-binding module, barnase, IgG binding domain ZZ, GB1, and SUMO. Recombinant polypeptides for use in methods herein may be produced in any recombinant expression system; e.g., in cell culture, or in a cell-free system such as a cell lysate or coupled transcription/translation system, and then purified therefrom, for example and without limitation, by affinity purification with immobilized agents (e.g., small molecules, and antibodies) that bind a tag comprised within the polypeptide.

In some embodiments, a host cell is transfected or transformed with an expression or cloning vector comprising a polynucleotide encoding the recombinant polypeptide (e.g., a polypeptide that is soluble in the cytosol of the cell), and the host cell is cultured in a conventional nutrient medium. Culture conditions, such as solute composition, temperature, and pH, can be selected from any of the many conditions known to support growth of particular host cells. In general, principles, protocols, and practical techniques for maximizing cell culture productivity are well-known and widely available to those in the art.

Retroviral proteases play an essential role in viral replication by hydrolyzing viral polyproteins at a limited number of sites. A general characteristic of viral proteases is the absence of distinct substrate recognition sequences, although amino-acids flanking the scissile bond must possess general features to be recognized by these proteases. In this context, cross-activity of retroviral proteases with other viral proteins is observed (as described, for example, in Tözsér (2010) Viruses 2010 2(1):147). Two types of cleavage sites are defined for these proteases; type 1 having an aromatic residue and proline at P1 and P1' positions and type 2 having hydrophobic residues at P1 position. In addition, general properties can be identified for amino acids occupying the P2 and P2' positions. This feature provides certain flexibility to the substrate binding pocket that can be exploited for hydrolyzing polyproteins without randomly cleaving the substrate. For example, HIV1 protease, when behaving as a type 1 protease, prefers Asn and Tyr or Phe at p2 and p1 positions, respectively. Therefore, repeating units of peptides like teriparatide that possess Asn-Phe at the C-terminus can be tailored with linker peptides containing Pro-Val-Gln (SEQ ID NO: 182) at P1', P2', and P3' positions followed by a number of amino acids to provide flexibility and recognition for another protease like caspases that leave no amino acid at the P1' position. Interestingly, the very same HIV protease recognizes Val-Leu, Ile-Met, Ile-Leu at p2-P1 positions. This type of diversity in substrate recognition can be seen in other retroviral proteases. Accordingly, preference for two consecutive hydrophobic residues at p2 and p1 positions (SEQ ID NO: 200), especially Val-Leu, Ile-Leu, and Leu-Leu, observed in HIV and other retroviral proteases can be exploited for the production of a tandem repeat of peptides like secretin. Type 1 and 2 cleavage sites are enumerated in, for example, FIG. 2 of Tözsér (2010) Viruses 2010 2(1):147.

In some embodiments, polypeptides may be engineered with tandem repeats having proteolytic recognition sequences subjected to limited hydrolysis to produce peptide standards. Caspases, for example, lose activity at 30° C. at roughly 2 hours. One skilled in the art will appreciate that peptides with various sizes and exact molecular weights may be produced by applying the enzyme to the polypeptides. The peptide standards yielded may be used in SDS-PAGE gels, calibrating size exclusion and reverse phase columns and mass spectrometric applications.

The following EXAMPLES are provided to illustrate certain particular features and/or embodiments. The examples should not be construed to limit the disclosure to the particular features or embodiments exemplified.

Polypeptides were engineered for the production of the recombinant peptides listed in Table 2. The polypeptides were engineered comprising the elements "$B_m$," "$L_{nk}$," and "DP," where $B_m$ is the recognition site of a protease that cleaves after two or four basic residues, $L_{nk}$ is a linker sequence, and DP is the recombinant peptide. The polypeptides were engineered to comprise a string of concatemers of units with the sequence $B_m$-$L_{nk}$-$B_m$-DP where the string of concatemers is preceded by the sequence $B_m$-DP, or units of DP-$B_m$ where the string of concatemers is preceded by a Met residue. The polypeptides were modified to contain a purification tag (TAG), such that the polypeptides had the amino acid sequence [TAG]$L_{nk}$-($B_m$-$L_{nk}$-$B_m$-DP)$_n$, or Met-(DP-$B_m$)$_n$-[TAG].

TABLE 2

Recombinant peptides.

| Peptide | Amino Acid Sequence | Sequence Identifier |
|---|---|---|
| Glucagon | HSQGTFTSDYSKYLDSRRAQDFVQWLMNT | SEQ ID NO: 84 |
| Exenatide | HGEGTFTSDLSKQMEEEAVRLFIEWLKNGG PSSGAPPPS | SEQ ID NO: 85 |
| Sermorelin | YADAIFTNSYRKVLGQLSARKLLQDIMSRQ | SEQ ID NO: 86 |
| Nesiritide (Natriuretic peptide B) | SPKMVQGSGCFGRKMDRISSSSGLGCKVLRRH | SEQ ID NO: 87 |
| Teduglutide | HGDGSFSDEMNTILDNLAARDFINWLIQTKITD | SEQ ID NO: 88 |
| [Cys(Acm)20, 31] Epidermal Growth Factor (20-31) | CMHIESLDSYTC | SEQ ID NO: 89 |
| T1 Peptide | MSRPACPNRKYG | SEQ ID NO: 90 |
| GTP-binding Protein Fragment, G☐ | CGAGESGKSTIVKQMK | SEQ ID NO: 91 |
| L-selectin Peptide | CQKLDKSFSMIK | SEQ ID NO: 92 |
| Peptide Standard 1 (amino acid analysis) | CPDFGHIAMELSVRTWKY | SEQ ID NO: 93 |
| ACTH (1-39) (Acthar) | SYSMEHFRWGKPVGKKRRPVKVYPDGAED QLAEAFPLEF | SEQ ID NO: 94 |
| ACTH (1-24) | SYSMEHFRWGKPVGKKRRPVKVYP | SEQ ID NO: 95 |
| Lepirudin | LVYTDCTESGQNLCLCEGSNVCGQGNKCILGSDG EKNQCVTGEGTPKPQSHNDGDFEEIPEEYLQ | SEQ ID NO: 96 |
| Calcitonin | CSNLSTCVLGKLSQELHKLQTYPRTNTGSGTP | SEQ ID NO: 97 |
| Somatostatin | AGCKNFFWKTFTSC | SEQ ID NO: 98 |
| Megainin 1 | GIGKFLHSAGKFGKAFVGEIMKS | SEQ ID NO: 99 |
| Megainin 2 | GIGKFLHSAKKFGKAFVGEIMNS | SEQ ID NO: 100 |
| Corticotropin | SYSMEHFRWGKPVGKKRRPVKVYPDGAEDQL AEAFPLEF | SEQ ID NO: 101 |
| Teriparatide | SVSEIQLMHNLGKHLNSMERVEWLRKKLQDVHNF | SEQ ID NO: 102 |
| Tesamorelin | YADAIFTNSYRKVLGQLSARKLLQDIMSRQ QGESNQERGARARL | SEQ ID NO: 103 |

TABLE 2-continued

Recombinant peptides.

| Peptide | Amino Acid Sequence | Sequence Identifier |
|---|---|---|
| Aprotinin | RPDFCLEPPYTGPCKARIIRYFYNAKAGLCQ TFVYGGCRAKRNNFKSAEDCMRTCGGA | SEQ ID NO: 104 |
| Vasopressin | CYFQNCPRG | SEQ ID NO: 105 |
| Oxytocin | CYIQNCPLG | SEQ ID NO: 106 |
| Insulin Chain A | GIVEQCCTSICSLYQLENYCN | SEQ ID NO: 107 |
| Insulin Chain B | FVNQHLCGSHLVEALYLVCGERGFFYTPKT | SEQ ID NO: 108 |
| Pramlinitide | KCNTATCATQRLANFLVHSSNNFGPILPPTNVGSNTY | SEQ ID NO: 109 |
| Liraglutide | HAEGTFTSDVSSYLEGQAAKEEFIAWLVRGRG | SEQ ID NO: 110 |
| ACE2 α1 Helix Sequence | IEEQAKTFLDKFNHEAEDLFYQS | SEQ ID NO: 111 |
| Sinapultide (KL4) | KLLLLKLLLLKLLLLKLLLL | SEQ ID NO: 112 |
| Thymalfasin | SDAAVDTSSEITTKDLKEKKEVVEEAEN | SEQ ID NO: 113 |
| Apolipoprotein B Synthetic Peptide | KYYELEEKIVSLI KN LLVALK | SEQ ID NO: 114 |
| Galanin | GWTLNSAGYLLGPHAVGNHRSFSDKNGLTS | SEQ ID NO: 115 |
| Tau Peptide (45-73) (Exon 2/Insert 1 domain) | ESPLQTPTEDGSEEPGSETSDAKSTPTAE | SEQ ID NO: 116 |
| Bivalirudin | FPRPGGGGNGDFEEIPEEYL | SEQ ID NO: 117 |
| Enfuviritide | YTSLIHSLIEESQNQQEKNEQELLELDKWASLWNWF | SEQ ID NO: 118 |
| Secretin | HSDGTFTSELSRLRDSARLQRLLQGLV | SEQ ID NO: 119 |
| Gramicidin D | VGALAVVVWLWLWLWX | SEQ ID NO: 120 |
| Glatiramer | EAYKAAEKAYAAKEAAKEAAKAKAEKKAAYAK AKAAKYEKKAKKAAAEYKKK | SEQ ID NO: 121 |

(iv) Examples

Example 1: Production of Glucagon Using Caspase-7 and NTCB

A recombinant polypeptide was engineered to produce glucagon, consisting of the target amino acid sequence HSQGTFTSDYSKYLDSRRAQDFVQWLMNT (SEQ ID NO: 84), without extraneous amino acids using Caspase-7 and NTCB. The polypeptide was engineered to comprise four repeats spaced with three peptide repeats possessing respectively the chemical cleavage site of cysteine, followed by glycine and DEVD sequence as the caspase recognition sequence (FIG. 4). Use of small amino acids, especially glycine, in the linker sequence combined with the use of proteases (e.g., Caspase-3 or -7) that recognize a high number of charged amino acids (e.g., the three charged (Asp and Glu) peptides out of four in the DEVD sequence) may promote the exposure of the cleavage sites to the cleaving reagents. Due to the absence of cysteine in the glucagon peptide, this amino acid was selected to facilitate NTCB proteolysis. The Caspase-7 recognition site (SEQ ID NO: 33) was chosen to direct enzymatic proteolysis without leaving a P1' amino acid in the cleavage product. An amino acid sequence comprising the NTCB cleavage sequence (SEQ ID NO: 46) was chosen to direct the removal of the linker sequence and Caspase-7 recognition site from the intermediate peptide product. A Gly linker was placed between the NTCB cleavage sequence and the Caspase-7 recognition site to increase the exposure of the Caspase-7 recognition sequence, increasing the efficiency of the caspase cleavage, and to reduce the likelihood of disulfide formation between the cysteines of the repeats. In the recombinant polypeptide, the protease recognition site is enclosed in chevrons (< >), the chemical cleavage sequence is enclosed in braces ({ }), and the linker is enclosed in brackets ([ ]):

(SEQ ID NO: 125)
HSQGTFTSDYSKYLDSRRAQDFVQWLMNT{C}[G]<DEVD>HSQ

GTFTSDYSKYLDSRRAQDFVQWLMNT{C}[G]<DEVD>HSQGTF

TSDYSKYLDSRRAQDFVQWLMNT{C}[G]<DEVD>HSQGTFTS

DYSKYLDSRRAQDFVQWLMNT.

A thioredoxin tag was then added to the polypeptide to produce:

```
                                        (SEQ ID NO: 195)
MSDKIIHLTDDSFDTDVLKADGAILVDFWAEWCGPCKMIAPIL

DEIADEYQGKLTVAKLNIDQNPGTAPKYGIRGIPTLLLFKNGE

VAATKVGALSKGQLKEFLDANLAGSGSGHMHHHHHHSSGLVPR

GSGMKETAAAKFERQHMDSPDLGTDDDDKAMADIGS[G]<DEV

D>HSQGTFTSDYSKYLDSRRAQDFVQWLMNT{C}[G]<DEVD>

HSQGTFTSDYSKYLDSRRAQDFVQWLMNT{C}{G}<DEVD>HS

QGTFTSDYSKYLDSRRAQDFVQWLMNT{C}[G]<DEVD>HSQG

TFTSDYSKYLDSRRAQDFVQWLMNT.
```

Figure 5A:
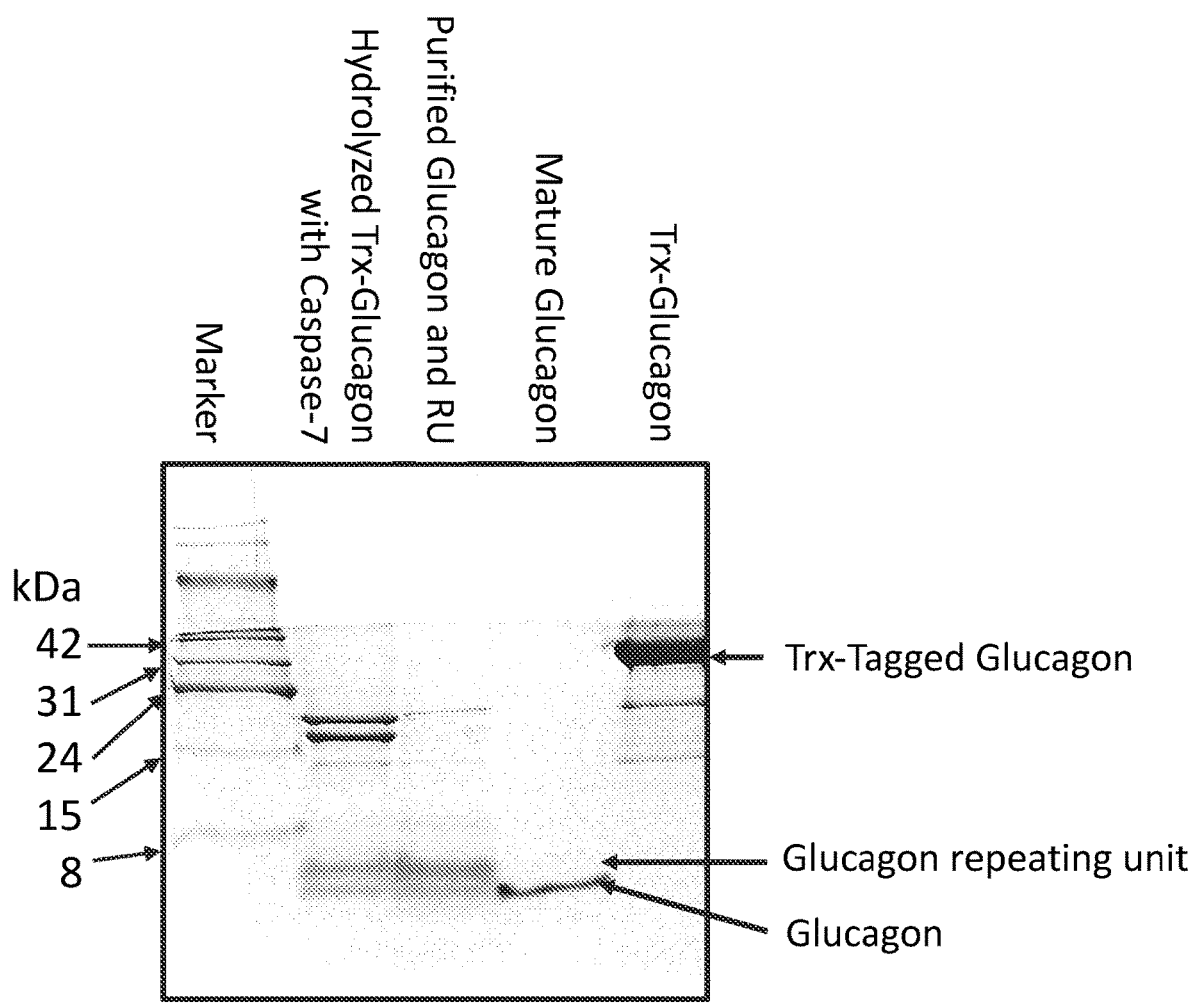
FIGS. 5A-5C. Shows production and processing of Thioredoxin tagged Glucagon (four repeats) and confirmation of the product mass by MALDI-TOF mass spectrometry.
Figure 5B:
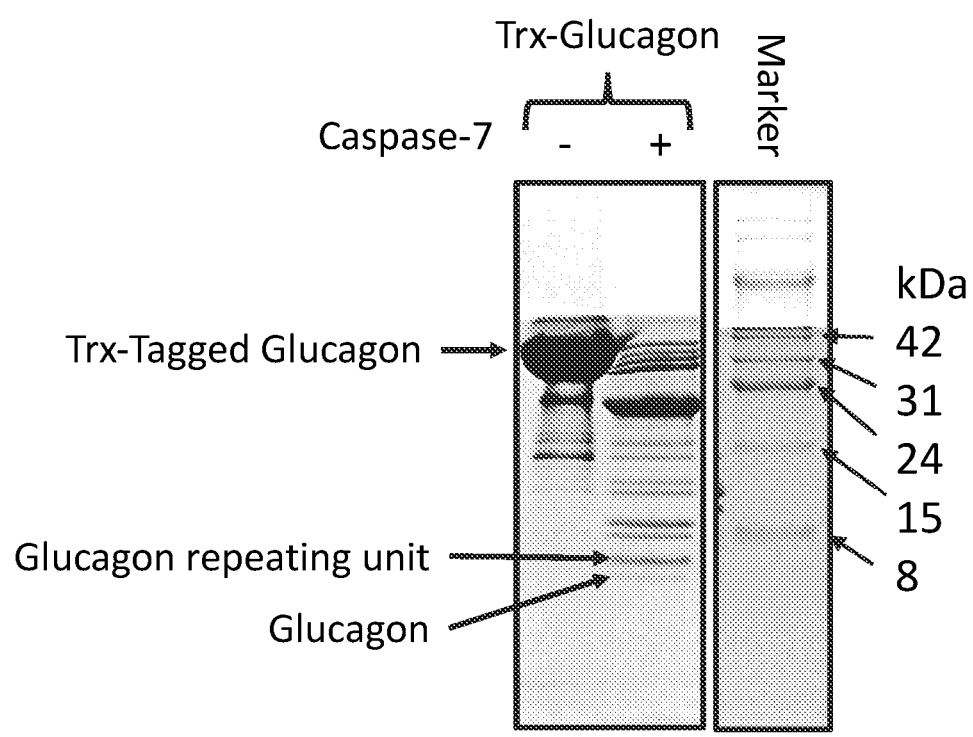

The thioredoxin-tagged polypeptide is recombinantly expressed in BL21-DE3 *E. coli* cells in 1 L LB medium, from a DNA construct at 30° C. for 7 hours. The cell paste is resuspended in 50 mM Tris-HCl, 100 mM NaCl, 5 mM imidazole, 0.5% Triton X-100, pH 8.0, followed by gentle sonication. Following a centrifugation for 15 minutes at 20,000×g, the supernatant is incubated with Ni-NTA resin for 1 hour at 4° C. The resin is washed with 50 mM Tris-HCl, 500 mM NaCl, 10 mM imidazole, pH 8.0. Then, the polypeptide is eluted with 300 mM imidazole in 50 mM Tris-HCl, pH 8.0, 10 mM β-mercaptoethanol, 10% glycerol. A yield of approximately 100 mg protein per 1 L culture is obtained, as determined by SDS-PAGE (FIG. 5A, 5B).

Figure 5C:
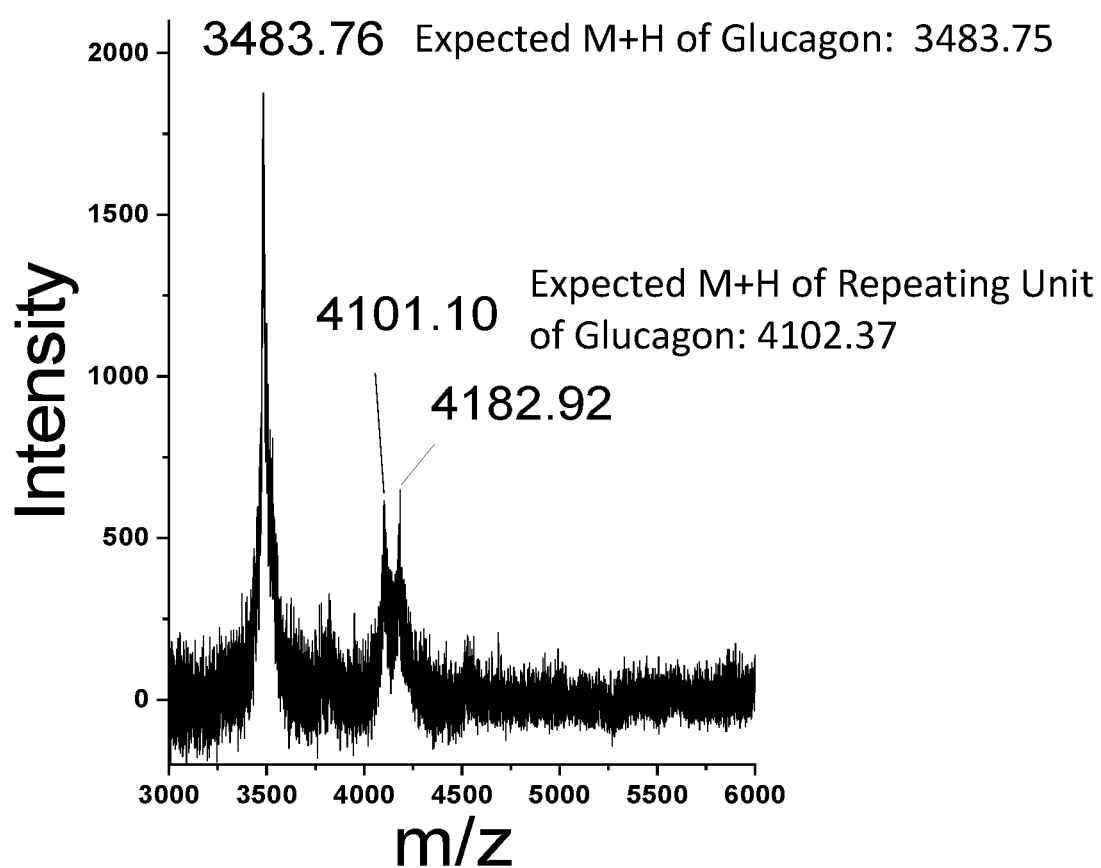

The purified polypeptide is treated with 1 mg recombinant histidine-tagged Caspase-7 protease for 4 hours at 30° C., cleaving the polypeptide at the SEQ ID NO: 34 recognition site. The Agilent 1260 infinity HPLC system equipped with Biorad Hipore C18 column was used to isolate the desired peptides from the thioredoxin tag and the protease. Thus, a twenty-minute acetonitrile gradient was setup from 5% to 90% in 0.1% trifluoracetic acid or formic acid with the flow rate of 1 ml/min. At the end of these steps, a mixture of mature glucagon and glucagon with the amino acid sequence CGDEVD (SEQ ID NO: 128) at its C-terminus is obtained at the time point of 20.4 minutes. The peptides were spotted on the MALDI plate followed by the addition of equal volume of saturated CHCA matrix. Then the masses of peptides were determined using AB Sciex 5800 MALDI-TOF mass spectrometer using TOF/TOF series explorer software V4 build 8 at the University of Irvine Mass spectrometry facility (FIG. 5C). The samples that were not obtained by C18 reverse phase column were desalted using Rainin PT-C18-96 PS C18 10 µL tips according to the manufacturers protocol prior to mass spectrometric analysis.

For the release of CGDEVD (SEQ ID NO: 128) from the C-terminus of the glucagon intermediate peptides, the cysteines are reduced with 1 mM dithiothreitol (DTT) or a 10× to 20× molar excess of Ekathiol under Argon gas while shaking for 2 hours at room temperature, pH=8. The supernatant containing the reduced protein is transferred to a new tube containing 5 to 10-fold of NTCB over the number of thiol groups. The tube is sealed under Argon gas and incubated for 60 minutes at 40° C. Then, the reagents are filtered out using spin columns or C18 reverse phase HPLC system. Finally, the cleavage of the cyanylated peptide or protein at the SEQ ID NO: 48 NTCB cleavage site is accomplished after increasing the pH to 9 by Tris base and incubation at 37° C. for 16 hours. Given that Glucagon starts with Histidine, this experiment shows that caspase-7 cleaves the chimeric protein efficiently even when the P1' residue is not small amino acids like Gly, Ala, Ser, or aromatic residues as indicated previously (Fuentes-Prior & Salvesen Biochem. J. 2004 Dec. 1; 384 (Pt 2): 201-232). In addition, near total digestion of the precursor protein into three major fragments confirms that all designed caspase-3/-7 recognition sequences are processed by the enzyme. Finally, limited hydrolysis produces all expected fragments indicating that all designed enzyme recognition cites are accessible more or less to a similar extent to the protease and that intra and inter molecular disulfide bonds are not established that would limit the accessibly of the designed proteolytic sequences to the protease. Finally, production of the protein in a soluble form confirms the proper design of the protein in preventing the formation of intermolecular disulfide bonds that may result in insoluble entangled precipitate.

Example 2: Production of Glucagon Using Caspases and Chemical Cleavage Agents

A polypeptide was engineered to produce glucagon without extraneous amino acids using caspases and $Pd^{2+}$. Instead of selecting cysteine for the chemical cleavage site, a proline-histidine dipeptide was used, since glucagon also lacks proline. Thioredoxin tagged tandem repeats of glucagon were engineered to comprise the caspase recognition site (SEQ ID NO: 32), an amino acid sequence comprising the $Pd^{2+}$ chemical cleavage sequence (SEQ ID NO: 50), and a linker sequence (SEQ ID NO: 61), resulting in a thioredoxin-tagged polypeptide amino acid sequence of:

```
                                        (SEQ ID NO: 196)
MSDKIIHLTDDSFDTDVLKADGAILVDFWAEWCGPCKMIAPIL

DEIADEYQGKLTVAKLNIDQNPGTAPKYGIRGIPTLLLFKNGE

VAATKVGALSKGQLKEFLDANLAGSGSGHMHHHHHHSSGLVPR

GSGMKETAAAKFERQHMDSPDLGTDDDDKAMADIGS[G]<DEV

D>HSQGTFTSDYSKYLDSRRAQDFVQWLMNT{PH}[GG]<DEV

D>HSQGTFTSDYSKYLDSRRAQDFVQWLMNT{PH}[GG]<DEV

D>HSQGTFTSDYSKYLDSRRAQDFVQWLMNT{PH}[GG]<DEV

D>HSQGTFTSDYSKYLDSRRAQDFVQWLMNT.
```

Thioredoxin tagged polypeptides containing the glucagon peptide are expressed in BL21-DE3 *E. coli* with a yield of approximately 100 mg protein per 1 L culture. Purification and treatment of the polypeptide with Caspase-7 is performed as described in Example 1: The fusion protein is produced in a soluble form and was purified using Ni-NTA column. Then it is treated with Caspase-7, which cleaves the protein at the SEQ ID NO: 34 recognition site to its components. The thioredoxin tag and Caspase-7, both of which possess histidine tag, are removed from the reaction mixture using a Ni-NTA affinity column. At the end of these steps, a mixture of mature glucagon and glucagon with an intermediate peptide product comprising glucagon, the caspase recognition site, the linker sequence, and the $Pd^{2+}$ cleavage site, PHGGDEVD (SEQ ID NO: 131), at its C-terminus are obtained. For the release of PHGGDEVD (SEQ ID NO: 131) from the C-terminus of glucagon, the mixture is treated with an equimolar amount of Pd(II) at pH 2 for two hours, cleaving the intermediate peptide product at the Pro-His $Pd^{2+}$ chemical cleavage site. Then, the reagents are filtered out using spin columns or a C18 reverse phase HPLC system.

Next, a polypeptide was engineered with a thioredoxin tag and four repeats containing the glucagon peptide, a Caspase-7 recognition sequence (SEQ ID NO: 33), a $Ni^{2+}$ chemical cleavage site (SEQ ID NO: 53), and a Gly linker, resulting in the sequence:

(SEQ ID NO: 197)
MSDKIIHLTDDSFDTDVLKADGAILVDFWAEWCGPCKMIAPILDEIADEY

QGKLTVAKLNIDQNPGTAPKYGIRGIPTLLLFKNGEVAATKVGALSKGQL

KEFLDANLAGSGSGHMHHHHHHSSGLVPRGSGMKETAAAKFERQHMDSPD

LGTDDDDKAMADIGS[G]<DEVD>HSQGTFTSDYSKYLDSRRAQDFVQWL

MNT{SRHW}[G]<DEVD>HSQGTFTSDYSKYLDSRRAQDFVQWLMNT

{SRHW}[G]<DEVD>HSQGTFTSDYSKYLDSRRAQDFVQWLMNT{SRHW}

[G]<DEVD>HSQGTFTSDYSKYLDSRRAQDFVQWLMNT.

Following treatment with Caspase-7 to cleave at SEQ ID NO: 34, and removal of the thioredoxin tag and the protease, 20 mM of the recombinant protein is incubated with 2 mM $NiCl_2$ in 100 mM Hepes buffer, pH 8.2 and 120 mM NaCl at 50° C. overnight, cleaving the intermediate peptide product at the SEQ ID NO: 56 chemical cleavage site to remove the extraneous amino acids, SRHWGDEVD (SEQ ID NO: 134), from the C-terminus of glucagon.

Example 3: Production of a Liraglutide Using Kexin and a Carboxypeptidase

A polypeptide was engineered to produce liraglutide, consisting of the target amino acid sequence HAEGTFTSDVSSYLEGQAAKEEFIAWLVRGRG (SEQ ID NO: 110). Due to the absence of two consecutive basic residues in liraglutide, the polypeptide was engineered to comprise four peptide repeats comprising liraglutide, and two Kexin recognition sites (SEQ ID NO: 2) separated by a Gly-Ser linker. A thioredoxin tag was added to the N-terminus to facilitate purification of the polypeptide:

(SEQ ID NO: 198)
MSDKIIHLTDDSFDTDVLKADGAILVDFWAEWCGPCKMIAPILDEIADEY

QGKLTVAKLNIDQNPGTAPKYGIRGIPTLLLFKNGEVAATKVGALSKGQL

KEFLDANLAGSGSGHMHHHHHHSSGLVPRGSGMKETAAAKFERQHMDSPD

LGTDDDDKAMADIGSG<RR>HAEGTFTSDVSSYLEGQAAKEEFIAWLVRG

RG<RR>[GS]<KR>HAEGTFTSDVSSYLEGQAAKEEFIAWLVRGRG<RR>

[GS]<RR>HAEGTFTSDVSSYLEGQAAKEEFIAWLVRGRG<RR>[GS]

<KR>HAEGTFTSDVSSYLEGQAAKEEFIAWLVRGRG.

Treatment of the purified recombinant polypeptide with Kexin to cleave the polypeptide at the protease recognition site results in a mixture of the mature form of liraglutide and intermediate peptide products comprising liraglutide with two basic residues (RR or KR) at the C-terminus. Treatment of these intermediate peptides with Carboxypeptidase B removes these extra basic amino acids, resulting in the mature liraglutide peptide.

The thioredoxin tagged polypeptide containing liraglutide is expressed in BL21-DE3 cells in 1 L LB medium at 37° C. for 7 hours. The cell paste is resuspended in 50 mM Tris-HCl, 100 mM NaCl, 5 mM imidazole, 0.5% Triton X-100, pH 8.0, followed by a gentle sonication. Following a centrifugation for 15 min at 20,000×g, the supernatant is incubated with Ni-NTA resin for 1 hour at 4° C. The resin is washed with 50 mM Tris-HCl, 500 mM NaCl, 10 mM imidazole, pH 8.0. The protein is next eluted with 300 mM imidazole in 50 mM Tris-HCl (pH, 8.0), 10 mM β-mercaptoethanol, 10% glycerol. The purity of the polypeptide is determined by SDS-PAGE.

The purified polypeptide is treated with 100 U histidine tagged kex2 protease at 37° C. in 200 mM Bis-Tris buffer, pH=7, plus 0.01% Triton X-100, 1 mM $CaCl_2$) for 4 hours, cleaving the polypeptide at the Arg-Arg and Lys-Arg Kexin recognition sites. The reactants are incubated with a Ni-NTA column for 60 minutes to remove the tag and the His tagged protease. Following a brief centrifugation, the supernatant is transferred into a new tube, into which Carboxypeoptidase B is added and incubated for 60 minutes at 23° C. Finally, the liraglutide peptide is purified from the linker sequence and individual amino acids by reverse phase HPLC using a C8 or C18 column.

Example 4: Production of a Liraglutide Using Caspases and Pd2+

Liraglutide does not possess proline, which allowed the inclusion of this amino acid in a cleavage site for $Pd^{2+}$ ions. In addition, no caspase recognition site is present. Therefore, a polypeptide for the production of liraglutide using Caspase-3 or Caspase-7 and $Pd^{2+}$ was engineered, and an N-terminal thioredoxin purification tag was added:

(SEQ ID NO: 199)
MSDKIIHLTDDSFDTDVLKADGAILVDFWAEWCGPCKMIAPILDEIADEY

QGKLTVAKLNIDQNPGTAPKYGIRGIPTLLLFKNGEVAATKVGALSKGQL

KEFLDANLAGSGSGHMHHHHHHSSGLVPRGSGMKETAAAKFERQHMDSPD

LGTDDDDKAMADIGS[G]<DEVD>HAEGTFTSDVSSYLEGQAAKEEFIAW

LVRGRG{PH}[GG]<DEVD>HAEGTFTSDVSSYLEGQAAKEEFIAWLVRG

RG{PH}[GG]<DEVD>HAEGTFTSDVSSYLEGQAAKEEFIAWLVRGRG

{PH}[GG]<DEVD>HAEGTFTSDVSSYLEGQAAKEEFIAWLVRGRG.

The purified recombinant protein is first digested with Caspase-3 or Caspase-7 to cleave the polypeptide at the Caspase-3/Caspase-7 recognition site (SEQ ID NO: 33), and the tag and caspase are removed with a Ni-NTA column, due to the presence of six histidines in both caspase and the tag. Next, the resulting intermediate product peptide, HAEGTFTSDVSSYLEGQAAKEEFIAWLVRG RGPHGGDEVD (SEQ ID NO: 140), is treated with $Pd^{2+}$ ions, which cleaves the intermediate peptide at the $Pd^{2+}$ chemical cleavage sequence (SEQ ID NO: 50) to remove the extraneous amino acids from the C-terminus, resulting in the liraglutide peptide.

The thioredoxin tagged polypeptide containing tandem repeats with liraglutide is produced and purified as described in Example 1: The purified protein is treated with 1 mg recombinant Hiss-tagged Caspase-7 protease at 30° C. in 50 mM HEPES, pH 7.4, 100 mM NaCl, 10% glycerol, 0.1 mM EDTA, 10 mM dithiothreitol, and 0.1% CHAPS for 4 hours, which cleaves the polypeptide at SEQ ID NO: 34. The reactants are incubated with a Ni-NTA resin for 60 minutes to remove the tag and the protease. Following a brief centrifugation, the supernatant is transferred into a new tube to which is added equimolar amount of cis-[Pd-(en) $(H_2O)_4]^{2+}$, Pd(II) reagent, and incubated at 60° C., pH 4 overnight, which cleaves the intermediate peptide product at SEQ ID NO: 51. Finally, the liraglutide peptide is purified from the linker sequence and individual amino acids by reverse phase HPLC using C8 or C18 columns.

In another example, Cys was substituted for the Pro-His dipeptide, and NTCB is used to remove the extraneous amino acids.

Example 5: Production of Insulin Using Caspases and Ni²⁺

The mature form of the insulin consists of B and A chains linked by two disulfide bonds.

```
                                       (SEQ ID NO: 108)
Insulin CHAIN-B:    FVNQHLCGSHLVEALYLVCGERGFFYTPKT (SEQ ID NO: 107)
Insulin CHAIN-A:    GIVEQCCTSICSLYQLENYCN
```

To produce insulin, a polypeptide containing two repeats of chain-A and two repeats of chain-B was engineered for isolation by treatment with a caspase and Ni²⁺, containing the caspase recognition site (SEQ ID NO: 32), the Ni²⁺ chemical cleavage site (SEQ ID NO: 53), and a Gly linker, so that the polypeptide had the sequence:

```
                                       (SEQ ID NO: 141)
FVNQHLCGSHLVEALYLVCGERGFFYTPKT{SRHW}[G]<DEVD>FVNQH

LCGSHLVEALYLVCGERGFFYTPKT{SRHW}[G]<DEVD>GIVEQCCTSI

CSLYQLENYCN{SRHW}[G]<DEVD>GIVEQCCTSICSLYQLENYCN.
```

The purified recombinant polypeptide is first digested with Caspase-3 or Caspase-7 at the caspase recognition site, and the caspase is removed with Ni-NTA column. Next, the resulting intermediate peptide products are treated with Ni²⁺ ions, which removes the extraneous SRHWGDEVD (SEQ ID NO: 134) amino acids from the C-terminus, resulting in a mixture of the insulin B-chain and A-chain peptides.

The purified polypeptide is treated with 1 mg recombinant histidine tagged Caspase-7 protease at 30° C. in 50 mM HEPES, pH 7.4, 100 mM NaCl, 10% glycerol, 0.1 mM EDTA, 10 mM dithiothreitol, and 0.1% CHAPS for 4 hours, cleaving the polypeptide at SEQ ID NO: 127 to produce an intermediate peptide product comprising insulin B-chain or insulin A-chain and SEQ ID NO: 134. The reactants are incubated with a Ni-NTA resin for 60 minutes to remove the protease. Following a brief centrifugation, the supernatant is incubated with 0.5 mM NiCl₂ in 100 mM Hepes buffer, pH 8.2 and 45° C. overnight, cleaving the intermediate peptide product at SEQ ID NO: 56, removing the extraneous amino acids (SEQ ID NO: 134) from the C-terminus. Finally, the insulin peptides are purified from the linker sequence and individual amino acids by reverse phase HPLC using C8 or C18 columns.

Example 6: Production of Insulin Using Kexin and a Carboxypeptidase

To produce insulin using Kexin and a carboxypeptidase, a polypeptide was engineered containing two repeats of chain-A and two repeats of chain-B, wherein the repeats comprise two Kexin recognition sites (SEQ ID NO: 2) separated by a linker sequence (SEQ ID NO: 62) at the C-terminus of the insulin chain peptides. The resulting polypeptide comprised the amino acid sequence:

```
                                       (SEQ ID NO: 142)
FVNQHLCGSHLVEALYLVCGERGFFYTPKT<RR>[GS]<KR>FVNQHLCG

SHLVEALYLVCGERGFFYTPKT<RR>[GS]<RR>GIVEQCCTSICSLYQL

ENYCN<RR>[GS]<KR>GIVEQCCTSICSLYQLENYCN.
```

The polypeptide containing the insulin B and A chain repeats is expressed in BL21-DE3 cells in 1 L LB medium at 37° C. for 7 hours. The cell paste is resuspended in 50 mM Tris-HCl, 100 mM NaCl, 5 mM imidazole, 0.5% Triton X-100, pH 8.0, followed by a gentle sonication. Following a centrifugation for 15 min at 20,000×g, the supernatant is incubated with Ni-NTA resin for 1 hour at 4° C. The resin is washed with 50 mM Tris-HCl, 500 mM NaCl, 10 mM imidazole, pH 8.0. The protein is next eluted with 300 mM imidazole in 50 mM Tris-HCl (pH, 8.0), 10 mM β-mercaptoethanol, 10% glycerol. The purity of the polypeptide is determined by SDS-PAGE.

The purified polypeptide is treated with 100 U histidine tagged kex2 protease at 37° C. in 200 mM Bis-Tris buffer, pH 7, plus 0.01% Triton X-100, 1 mM CaCl₂ for 4 hours to cleave the polypeptide at SEQ ID NO: 3 and SEQ ID NO: 4, resulting in intermediate peptide products, FVNQHLCGSHLVEALYLVCGERGFFYTPKT<RR> (SEQ ID NO: 143) and GIVEQCCTSICSLYQ LENYCN<RR> (SEQ ID NO: 144). The reactants are incubated with a Ni-NTA column for 60 minutes to remove the His tagged protease. Following a brief centrifugation, the supernatant is transferred into a new tube, into which Carboxypeptidase B is added and incubated for 60 minutes at 23° C. to remove the C-terminal Arg-Arg dipeptide. Finally, the insulin peptides are purified from the linker sequence and individual amino acids by reverse phase HPLC using a C8 or C18 column.

Example 7: Production of Teriparatide Using Proteases

Teriparatide does not possess a proline and the final two amino acids terminate with asparagine and phenylalanine that are the preferred sequences for a number of retroviral proteases including HIV-1 protease. This allowed the inclusion of proline immediately after the last amino acid as a cleavage site for HIV-1 protease. In addition, no caspase cleavage site is present, so a recombinant polypeptide with an N-terminal tag was engineered for production of Teriparatide using Caspase-3 or Caspase-7 and HIV protease, comprising the Caspase-3/Caspase-7 cleavage site (SEQ ID NO: 33), the HIV-protease cleavage site, and a Pro-Isoleucine-Serine at the N-terminus of the repeating units:

```
                                       (SEQ ID NO: 190)
TAG[S]<DEVD>SVSEIQLMHNLGKHLNSMERVEWLRKKLQDVHNF{P}

[IS]<DEVD>SVSEIQLMHNLGKHLNSMERVEWLRKKLQDVHNF{P}

[IS]<DEVD>SVSEIQLMHNLGKHLNSMERVEWLRKKLQDVHNF{P}

[IS]<DEVD>SVSEIQLMHNLGKHLNSMERVEWLRKKLQDVHNF
```

It may be understood in this example that a Ser residue may act as both a portion of the HIV1-protease recognition sequence and a linker sequence. The combination of NF dipeptide at the C-terminus of Teriparatide and the design of PIS as a linker sequence creates HIV1-protease recognition sequence. Thus, the following chimeric protein was designed and produced in *E. coli*:

```
                                        (SEQ ID NO: 191)
MSDKIIHLTDDSFDTDVLKADGAILVDFWAEWCGPCKMIAPILDEIADEY

QGKLTVAKLNIDQNPGTAPKYGIRGIPTLLLFKNGEVAATKVGALSKGQL

KEFLDANLAGSGSGHMHHHHHHSSGLVPRGSGMKETAAAKFERQHMDSPD

LGTDDDDKAMADIGSGDEVDSVSEIQLMHNLGKHLNSMERVEWLRKKLQD

VHNFPISDEVDSVSEIQLMHNLGKHLNSMERVEWLRKKLQDVHNFPISDE

VDSVSEIQLMHNLGKHLNSMERVEWLRKKLQDVHNFPISDEVDSVSEIQL

MHNLGKHLNSMERVEWLRKKLQDVHNF (FIG. 6A).
```

Figure 6A:
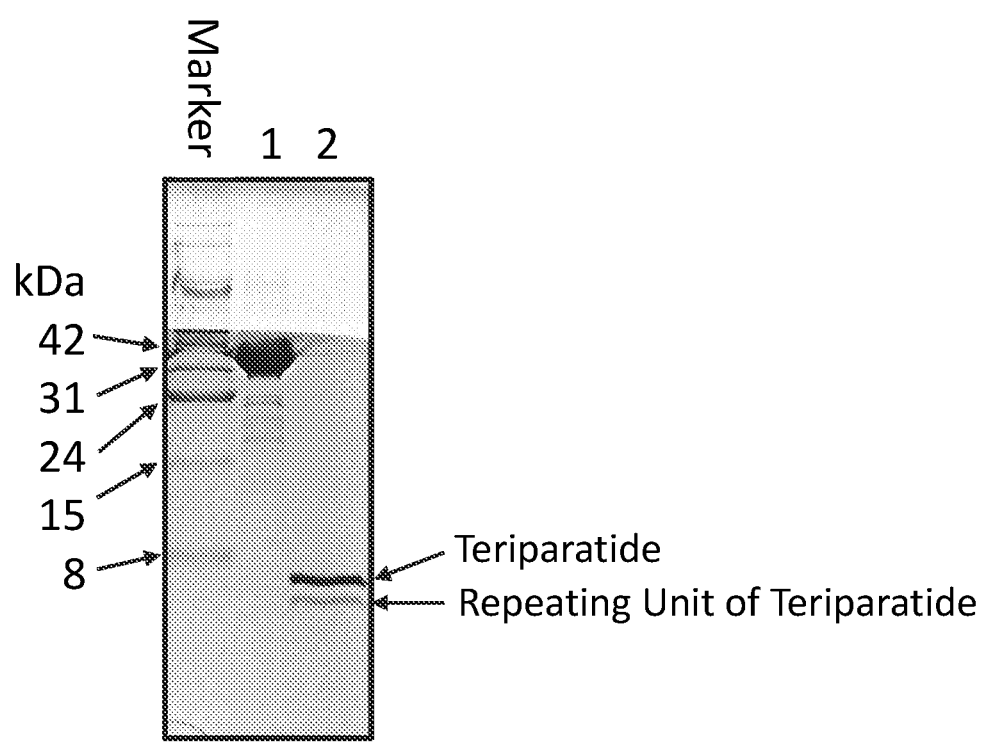
FIGS. 6A-6D show the production in *E. coli* and processing of thioredoxin tagged of four repeats of teriparatide by caspases of -3, -7 and HIV1 protease.
Figure 6B:
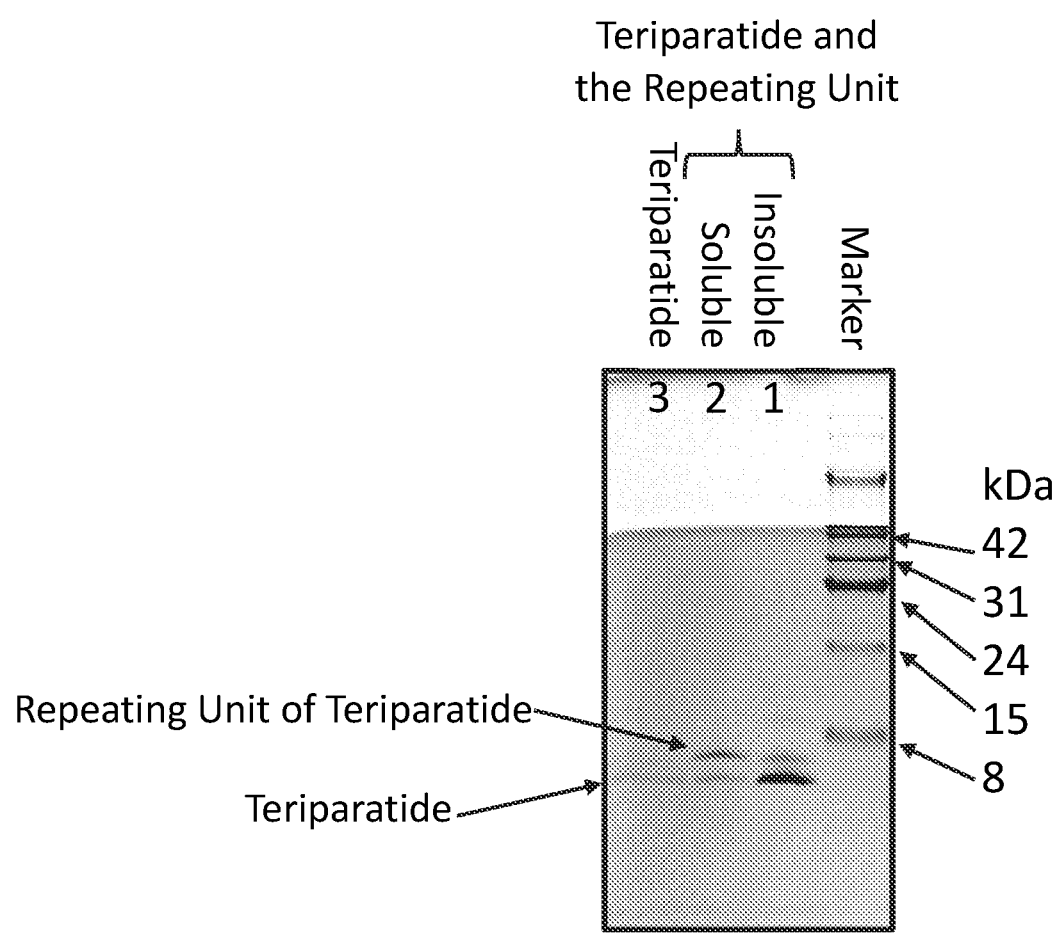
Figure 6C:
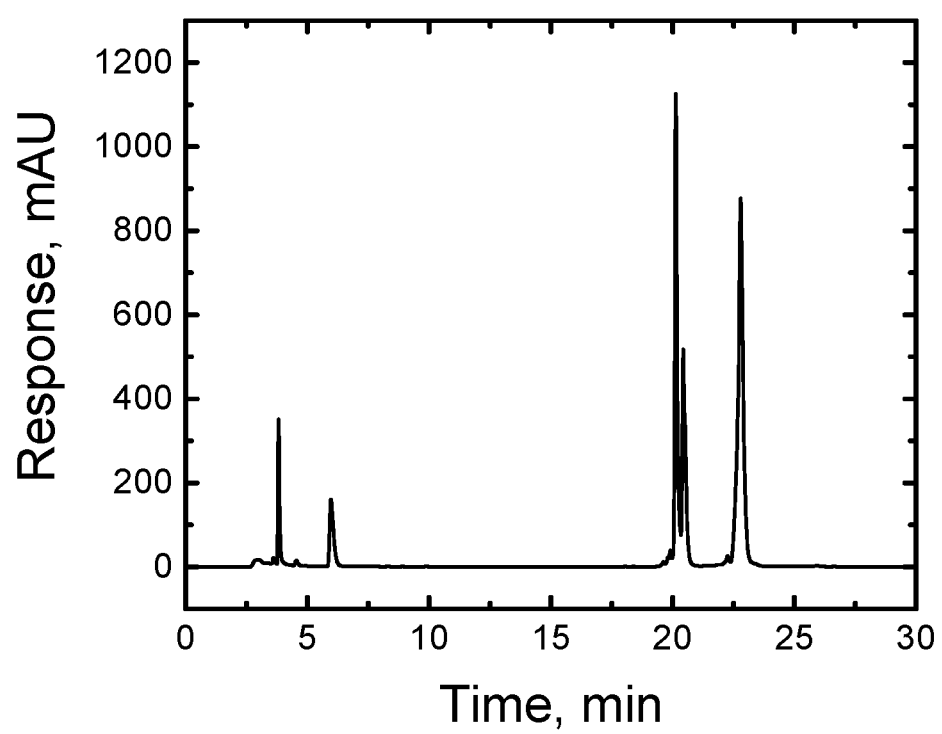
Figure 6D:
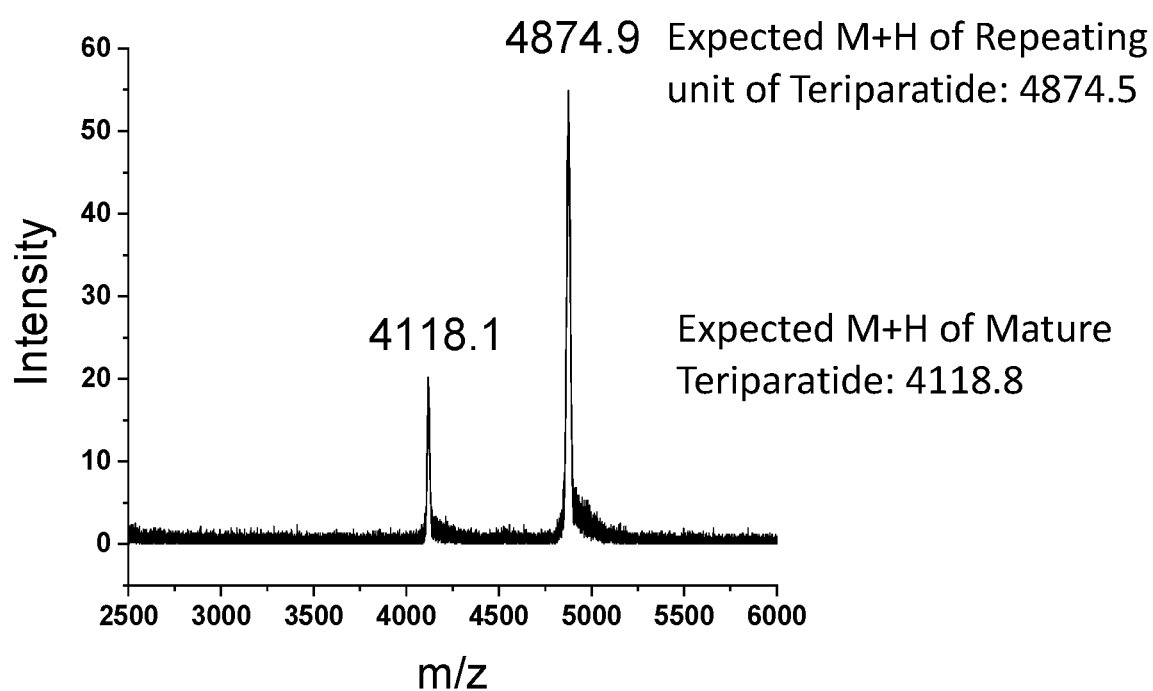

Proteolysis of the recombinant polypeptide of SEQ ID NO: 191 using Caspase-3 or Caspase-7 cleaves the polypeptide at SEQ ID NO: 34 to yield a mixture of mature teriparatide and the intermediate peptide product, SVSEIQLMHN LGKHLNSMERVEWLRKKLQDVHN FPISDEVD (SEQ ID NO: 192) (FIG. 6A). Proteolysis catalyzed by HIV-1 protease removes the extraneous PIS-DEVD (SEQ ID NO: 193) amino acids to yield mature teriparatide (FIG. 6B). HPLC analysis of caspase-3 treated of four repeats of teriparatide tagged with thioredoxin produces five peaks (FIG. 6C). The peaks at 3.8 and 5.9 minutes are impurities, while those at 20.2, 20.4, and 22.8 minutes belong to teriparatide, its repeating unit, and thioredoxin tag, respectively. Masses obtained by MALDI-TOF mass spectrometer of the eluted peaks at 20.2 and 20.4 confirms that indeed teriparatide and its repeating units are eluded at the indicated time points (FIG. 6D).

A polypeptide with an N-terminal tag was also engineered for production of liraglutide using Kexin and Carboxypeptidase B, comprising the Kexin cleavage site (SEQ ID NO: 3 and SEQ ID NO: 4), and the Carboxypeptidase C cleavage site:

```
                                        (SEQ ID NO: 148)
TAG<RR>HAEGTFTSDVSSYLEGQAAKEEFIAWLVRGRG<RR>HAEGTFT

SDVSSYLEGQAAKEEFIAWLVRGRG<KR>HAEGTFTSDVSSYLEGQAAKE

EFIAWLVRGRG<KR>HAEGTFTSDVSSYLEGQAAKEEFIAWLVRGRG.
```

Proteolysis of the recombinant polypeptide of SEQ ID NO: 148 using Kexin cleaves the polypeptide at SEQ ID NO: 3 and SEQ ID NO: 4 to yield a mixture of mature liraglutide and the intermediate peptide products, HAEGTFTSDVSSYLEGQAAKEEFIAWLVRGRG (SEQ ID NO: 110) and HAEGTFTSDVSSYLEGQAAKEEFIAWLVRGRG<RR> (SEQ ID NO: 194). Proteolysis catalyzed by Carboxypeptidase C removes the extraneous RR and KR amino acids to yield mature liraglutide.

A polypeptide with an N-terminal tag was also engineered for production of liraglutide using Enterokinase and $Ni^{2+}$, comprising the Enterokinase cleavage site (SEQ ID NO: 31), the $Ni^{2+}$ cleavage site, and a linker sequence:

```
                                        (SEQ ID NO: 153)
TAG<DDDDK>HAEGTFTSDVSSYLEGQAAKEEFIAWLVRGRG{SRHW}

[G]<DDDDK>HAEGTFTSDVSSYLEGQAAKEEFIAWLVRGRG{SRHW}

[G]<DDDDK>HAEGTFTSDVSSYLEGQAAKEEFIAWLVRGRG{SRHW}

[G]<DDDDK>HAEGTFTSDVSSYLEGQAAKEEFIAWLVRGRG.
```

Proteolysis of the recombinant polypeptide of SEQ ID NO: 153 using Enterokinase cleaves the polypeptide at SEQ ID NO: 31 to yield a mixture of mature liraglutide and the intermediate peptide product, HAEGTFTSDVS-SYLEGQAAKEEFIAWLVRGRGSRH WG<DDDDK> (SEQ ID NO: 155). Hydrolysis catalyzed by $Ni^{2+}$ removes the extraneous SRHWGDDDDK (SEQ ID NO: 154) amino acids to yield mature liraglutide.

Following the production and purification of liraglutide from the above recombinant polypeptides, the polypeptide is treated with Caspase-3 or Caspase-7, Kexin, or Enterokinase, respectively, and carboxypeptidase C, either sequentially or simultaneously, and the resulting mature peptides along with the linker sequence are subjected to reverse phase chromatography for further purification.

Example 8: Production of Insulin Using Caspase, Kexin, and Carboxypeptidases To produce insulin using a caspase, Kexin, and a carboxypeptidase, several His-tagged polypeptides were engineered containing two, three, four, or seven repeats comprising insulin B-chain or A-chain subunit, caspase recognition site (SEQ ID NO: 32), the Kexin recognition site (SEQ ID NO: 2), and a linker sequence (SEQ ID NO: 82 or SEQ ID NO: 83).

```
2 A-chain and B-chain subunits:
                                        (SEQ ID NO: 156)
MHHHHHHALWMRLLPLLALLALWGPD<DEVD>FVNQHLCGSHLVEALYLV

CGERGFFYTPKT<RR>EAEDLQVGQVELGGGPGAGSLQPLALEGSLQ

<KR>GIVEQCCTSICSLYQLENYCN<RR>GAGAGAMALWMRLLPLLALLA

LWGPD<DEVD>FVNQHLCGSHLVEALYLVCGERGFFYTPKT<RR>EAEDL

QVGQVELGGGPGAGSLQPLALEGSLQ<KR>GIVEQCCTSICSLYQLENYC

N

3 A-chain and B-chain subunits:
                                        (SEQ ID NO: 157)
MHHHHHHALWMRLLPLLALLALWGPD<DEVD>FVNQHLCGSHLVEALYLV

CGERGFFYTPKT<RR>EAEDLQVGQVELGGGPGAGSLQPLALEGSLQ

<KR>GIVEQCCTSICSLYQLENYCN<RR>GAGAGAMALWMRLLPLLALLA

LWGPD<DEVD>FVNQHLCGSHLVEALYLVCGERGFFYTPKT<RR>EAEDL

QVGQVELGGGPGAGSLQPLALEGSLQ<KR>GIVEQCCTSICSLYQLENYC

N<RR>GAGAGAMALWMRLLPLLALLALWGPD<DEVD>FVNQHLCGSHLVE

ALYLVCGERGFFYTPKT<RR>EAEDLQVGQVELGGGPGAGSLQPLALEGS

LQ<KR>GIVEQCCTSICSLYQLENYCN

4 A-chain and B-chain subunits:
                                        (SEQ ID NO: 158)
MHHHHHHALWMRLLPLLALLALWGPD<DEVD>FVNQHLCGSHLVEALYLV

CGERGFFYTPKT<RR>EAEDLQVGQVELGGGPGAGSLQPLALEGSLQ

<KR>GIVEQCCTSICSLYQLENYCN<RR>GAGAGAMALWMRLLPLLALLA

LWGPD<DEVD>FVNQHLCGSHLVEALYLVCGERGFFYTPKT<RR>EAEDL

QVGQVELGGGPGAGSLQPLALEGSLQ<KR>GIVEQCCTSICSLYQLENYC

N<RR>GAGAGAMALWMRLLPLLALLALWGPD<DEVD>FVNQHLCGSHLVE

ALYLVCGERGFFYTPKT<RR>EAEDLQVGQVELGGGPGAGSLQPLALEGS
```

LQ<KR>GIVEQCCTSICSLYQLENYCN<RR>GAGAGAMALWMRLLPLLAL

LALWGPD<DEVD>FVNQHLCGSHLVEALYLVCGERGFFYTPKT<RR>EAE

DLQVGQVELGGGPGAGSLQPLALEGSLQ<KR>GIVEQCCTSICSLYQLEN

YCN

7 A-chain and B-chain subunits:

(SEQ ID NO: 159)
MHHHHHHALWMRLLPLLALLALWGPD<DEVD>FVNQHLCGSHLVEALYLV

CGERGFFYTPKT<RR>EAEDLQVGQVELGGGPGAGSLQPLALEGSLQ

<KR>GIVEQCCTSICSLYQLENYCN<RR>GAGAGAMALWMRLLPLLALLA

LWGPD<DEVD>FVNQHLCGSHLVEALYLVCGERGFFYTPKT<RR>EAEDL

QVGQVELGGGPGAGSLQPLALEGSLQ<KR>GIVEQCCTSICSLYQLENYC

N<RR>GAGAGAMALWMRLLPLLALLALWGPD<DEVD>FVNQHLCGSHLVE

ALYLVCGERGFFYTPKT<RR>EAEDLQVGQVELGGGPGAGSLQPLALEGS

LQ<KR>GIVEQCCTSICSLYQLENYCN<RR>GAGAGAMALWMRLLPLLAL

LALWGPD<DEVD>FVNQHLCGSHLVEALYLVCGERGFFYTPKT<RR>EAE

DLQVGQVELGGGPGAGSLQPLALEGSLQ<KR>GIVEQCCTSICSLYQLEN

YCN<RR>GAGAGAMALWMRLLPLLALLALWGPD<DEVD>FVNQHLCGSHL

VEALYLVCGERGFFYTPKT<RR>EAEDLQVGQVELGGGPGAGSLQPLALE

GSLQ<KR>GIVEQCCTSICSLYQLENYCN<RR>GAGAGAMALWMRLLPLL

ALLALWGPD<DEVD>FVNQHLCGSHLVEALYLVCGERGFFYTPKT<RR>E

AEDLQVGQVELGGGPGAGSLQPLALEGSLQ<KR>GIVEQCCTSICSLYQL

ENYCN<RR>GAGAGAMALWMRLLPLLALLALWGPD<DEVD>FVNQHLCGS

HLVEALYLVCGERGFFYTPKT<RR>EAEDLQVGQVELGGGPGAGSLQPLA

LEGSLQ<KR>GIVEQCCTSICSLYQLENYCN

Any of the polypeptides is treated with Kexin and Carboxypeptidase B while the purified protein is attached to the Ni-NTA column. Kexin cleaves the polypeptide at SEQ ID NO: 3 and SEQ ID NO: 4 to produce intermediate peptides:

(SEQ ID NO: 160)
MHHHHHHALWMRLLPLLALLALWGPD<DEVD>FVNQHLCGSHLVEALYLV

CGERGFFYTPKT<RR>;

(SEQ ID NO: 144)
GIVEQCCTSICSLYQLENYCN<RR>;

(SEQ ID NO: 161)
GAGAGAMALWMRLLPLLALLALWGPD<DEVD>FVNQHLCGSHLVEALYLV

CGERGFFYTPKT<RR>;

and mature insulin A-chain (SEQ ID NO: 107), while Carboxypeptidase B also removes extraneous C-terminal amino acids to produce a product mixture of:

(SEQ ID NO: 162)
MHHHHHHALWMRLLPLLALLALWGPD<DEVD>FVNQHLCGSHLVEALYLV

CGERGFFYTPKT;

(SEQ ID NO: 163)
GAGAGAMALWMRLLPLLALLALWGPD<DEVD>FVNQHLCGSHLVEALYLV

CGERGFFYTPKT;

and mature insulin A-chain (SEQ ID NO: 107).

The column is then washed with PBS buffer. This removes the linker peptide and basic amino acids. Then, His-tagged Caspase-7 is added to the column, resulting in the hydrolysis of the His-tagged propeptide from the mature insulin at SEQ ID NO: 34. Mature insulin is released from the column due to the hydrolysis.

Example 9: Production of Insulin Using Caspases and a Carboxypeptidase in a Host that is Genetically Modified to Produce Kexin To produce insulin using a caspase, Kexin, and a carboxypeptidase in a host that is genetically modified to produce Kexin, several polypeptides were engineered containing B-chain and A-chain insulin subunit repeats comprising the caspase recognition sequence (SEQ ID NO: 32), the Kexin recognition sequence (SEQ ID NO: 2), and a linker sequence (SEQ ID NO: 74 or SEQ ID NO: 123):

(SEQ ID NO: 164)
G<RR>[HHHHHH]<DEVD>FVNQHLCGSHLVEALYLVCGERGFFYTPKT

<RR>[GHHHHHH]<DEVD>FVNQHLCGSHLVEALYLVCGERGFFYTPK

T<RR>[HHHHHH]<DEVD>GIVEQCCTSICSLYQLENYCN<RR>

[GHHHHHH]<DEVD>GIVEQCCTSICSLYQLENYCN (SEQ ID NO: 165)
G<RR>[HHHHHH]<DEVD>GIVEQCCTSICSLYQLENYCN<RR>

[GHHHHHH]<DEVD>GIVEQCCTSICSLYQLENYCN<RR>[HHHHHH]

<DEVD>FVNQHLCGSHLVEALYLVCGERGFFYTPKT<RR>[GHHHHHH]

<DEVD>FVNQHLCGSHLVEALYLVCGERGFFYTPKT

The production and processing of the mature insulin in this example is performed using the *Pichia*™ expression system (VALIDOGEN), according to the manufacturer's instructions. The pic3.5 vector clone containing a polynucleotide coding for the engineered polypeptide is transformed into the *Pichia*™ *P. pastoris* strain using electroporation. Transformants are screened by real time PCR for the presence of the DNA sequence of the construct, and the clone exhibiting the maximum level is used for the scale-up. For the large-scale production, cells are grown in 500 mL buffered minimal glycerol medium at 30° C. overnight, harvested by centrifugation, washed and resuspended in 50 mL buffered minimal methanol medium. The culture supernatants are harvested after 16 hrs, and the recombinant polypeptides are purified as described previously for glucagon.

Because the genetically modified host strain produces Kexin (Kex2) that is deficient from the ER signaling sequence and the transmembrane region, the polypeptide of SEQ ID NO: 164 is cleaved inside the host at SEQ ID NO: 3, yielding intermediate peptide products GHHHHHHDEVDFVNQHLCGSHLVEALYL-VCGERGFFYTPKTRR (SEQ ID NO: 166) and HHHHHHDEVDGIVEQCCTSICSLYQLENYCNRR (SEQ ID NO: 167).

Similarly, the polypeptide of SEQ ID NO: 165 is cleaved inside the host at SEQ ID NO: 3, yielding intermediate peptides GHHHHHHDEVDGIVEQCCTSICSLYQLE-NYCN RR (SEQ ID NO: 168), and HHHHHHDEVDFVNQHLCGSHLVEALYL-VCGERGFFYTPKTRR (SEQ ID NO: 169).

Treatment of the either of the foregoing resulting peptide mixtures with a combination of Carboxypeptidase B and Caspase-7 sequentially or simultaneously results in insulin chain A and chain B, without any extraneous amino acids.

In another example, the host is genetically modified to express Carboxypeptidase B in addition to Kexin, such that the intermediate peptides produced in the host comprise the amino acid sequences GHHHHHHDEVDFVNQHLCGSHLVEALYL-VCGERGFFYTPKT (SEQ ID NO: 170) and HHHHHHDEVDGIVEQCCTSICSLYQLENYCN (SEQ ID NO: 171); or GHHHHHHDEVDGIVEQCC TSICSLYQLE-NYCN (SEQ ID NO: 172) and HHHHHHDEVDFVNQHLCGSHLVEALYLVCGERGF FYTPKT (SEQ ID NO: 173). The proteolysis of these peptides with Caspase-3 or Caspase-7 at SEQ ID NO: 34 yields chains A and B of Insulin without any extraneous amino acid.

Example 10: Production of Teriparatide Using Caspases and $Ni^{2+}$

A polypeptide was engineered with a thioredoxin tag and four repeats containing the teriparatide peptide, a Caspase-7(-3) recognition sequence (SEQ ID NO: 33), a $Ni^{2+}$ chemical cleavage site (SEQ ID NO: 53), and a linker sequence, resulting in the sequence:

```
                                          (SEQ ID NO: 189)
MSDKIIHLTDDSFDTDVLKADGAILVDFWAEWCGPCKMIAPILDEIADEY

QGKLTVAKLNIDQNPGTAPKYGIRGIPTLLLFKNGEVAATKVGALSKGQL

KEFLDANLAGSGSGHMHHHHHHSSGLVPRGSGMKETAAAKFERQHMDSPD

LGTDDDDKAMADIGG[S]<DEVD>SVSEIQLMHNLGKHLNSMERVEWLRK

KLQDVHNF{SRHW}[S]<DEVD>SVSEIQLMHNLGKHLNSMERVEWLRKK

LQDVHNFSRHWSDEVDSVSEIQLMHNLGKHLNSMERVEWLRKKLQDVHNF

SRHWSDEVDSVSEIQLMHNLGKHLNSMERVEWLRKKLQDVHNF.
```

Figure 7A:
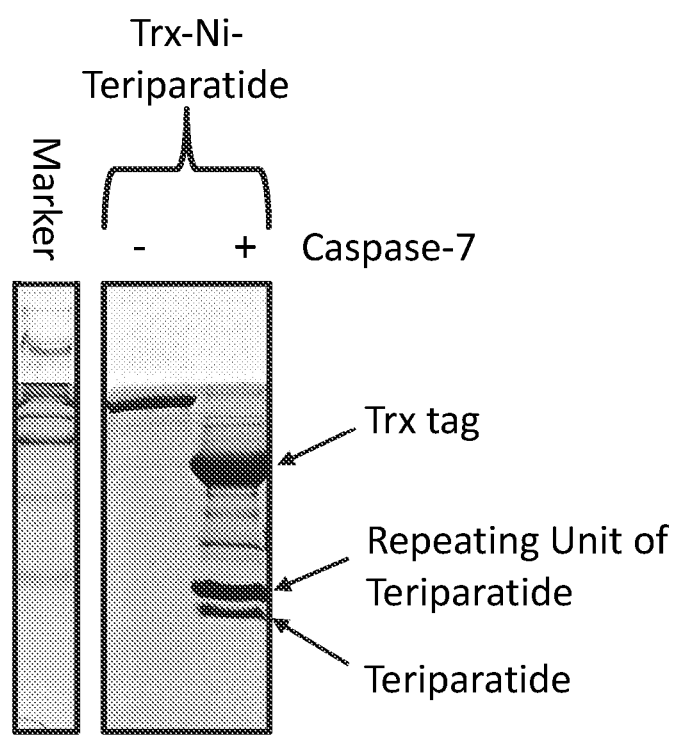
FIGS. 7A-7G. show production in *E. coli* and processing of thioredoxin tagged teriparatide (four repeats) possessing caspase-3 (-7) and $Ni^{2+}$ cleavage sequences.
Figure 7B:
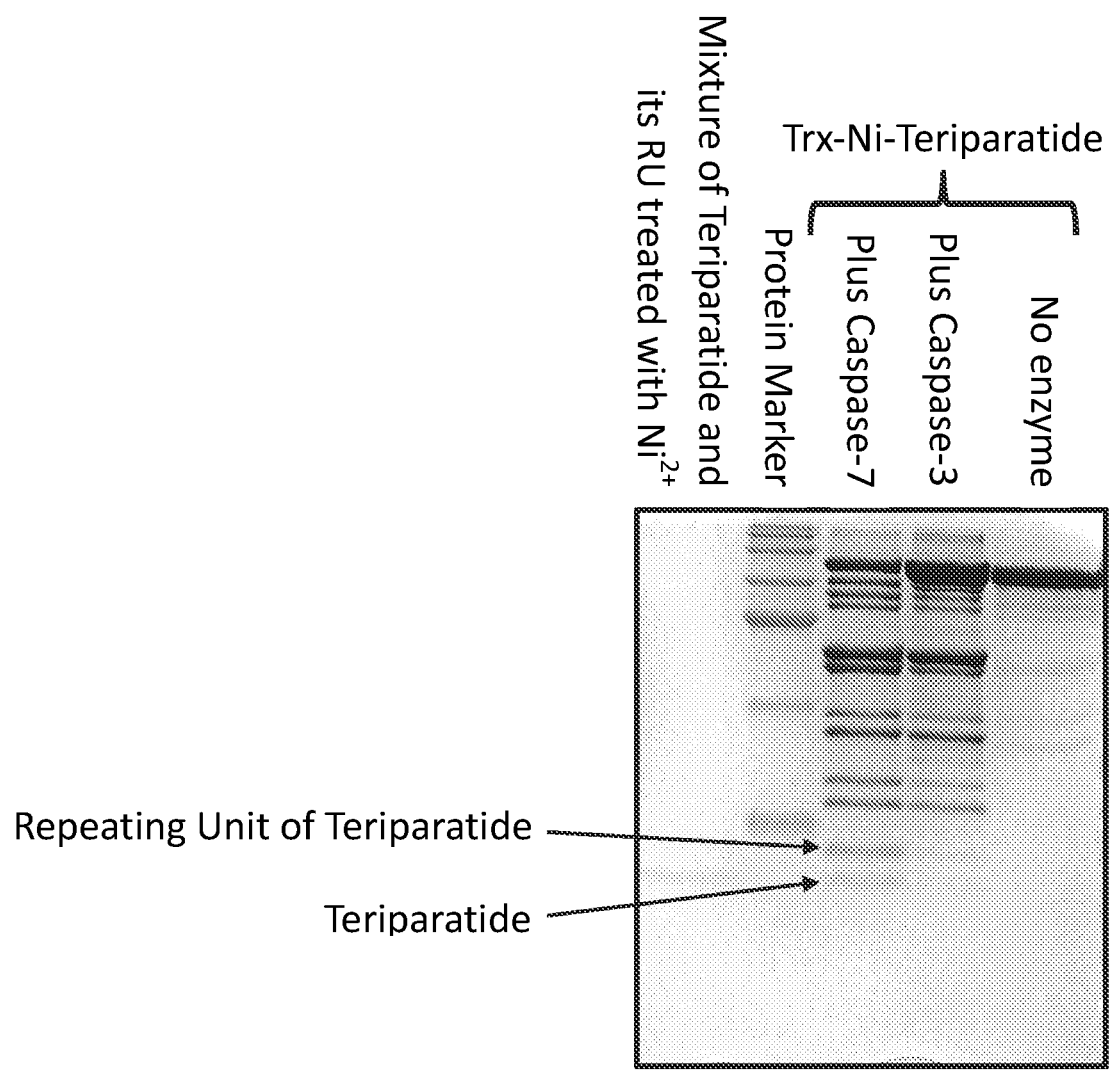
Figure 7C:
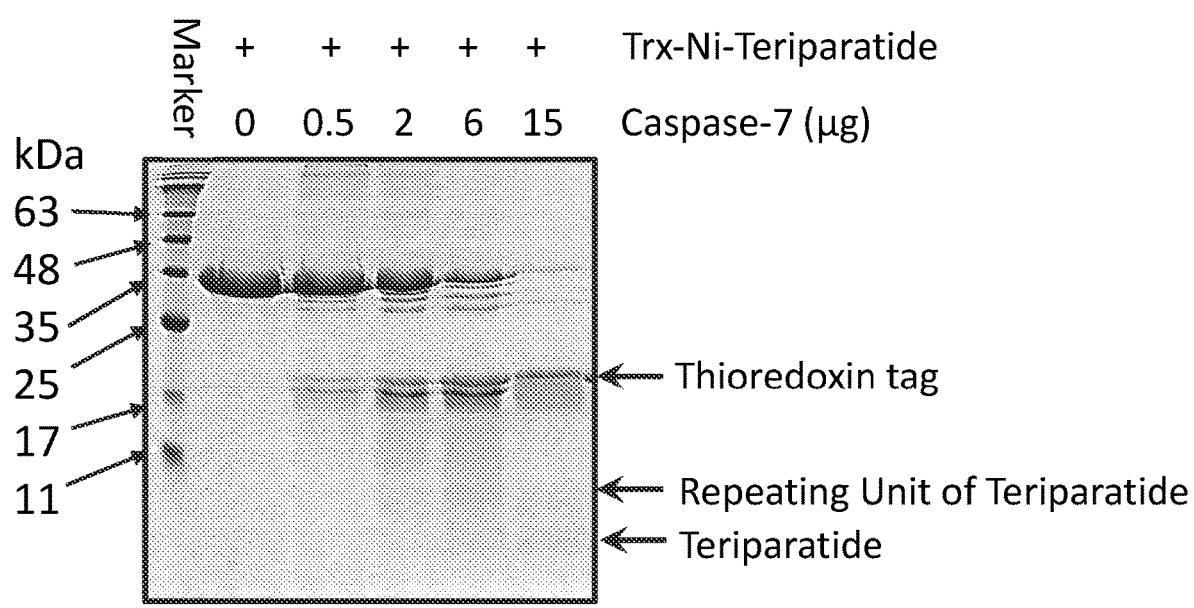
Figure 7D:
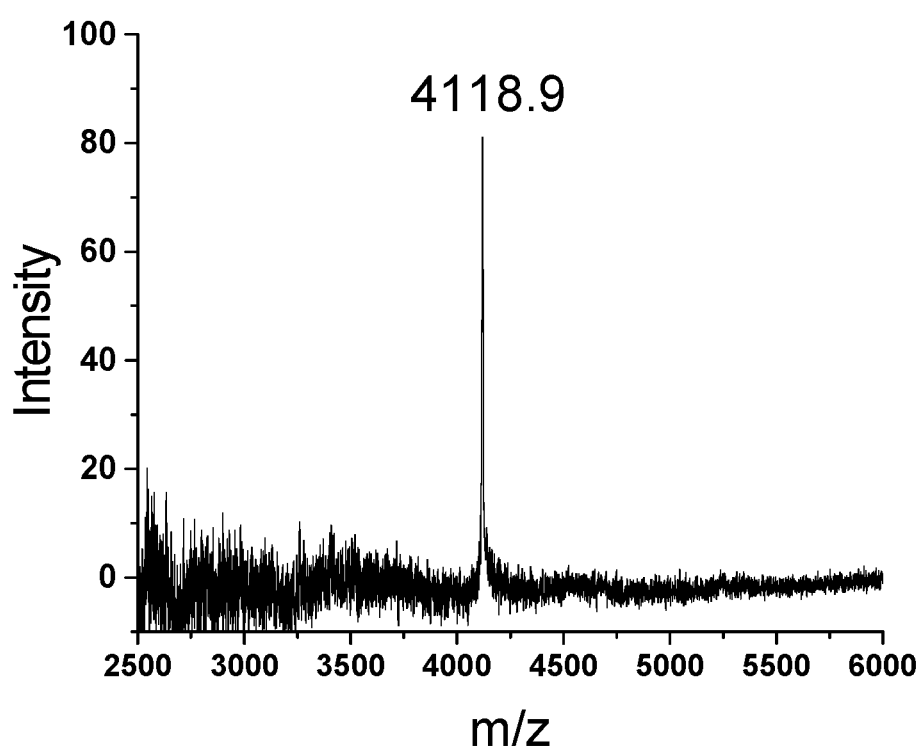
Figure 7E:
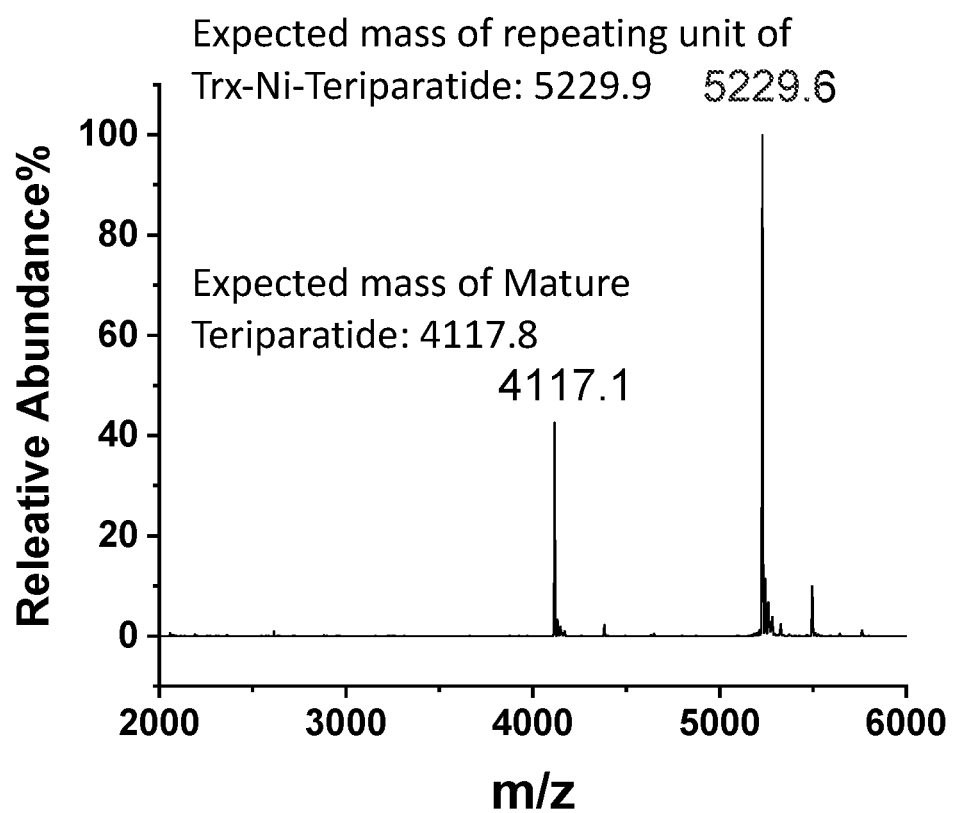
Figure 7F:
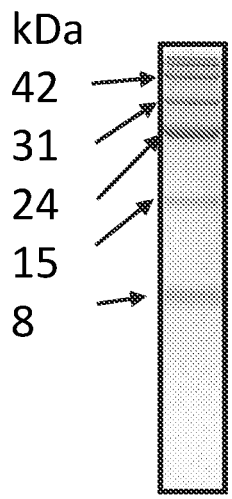
Figure 7G:
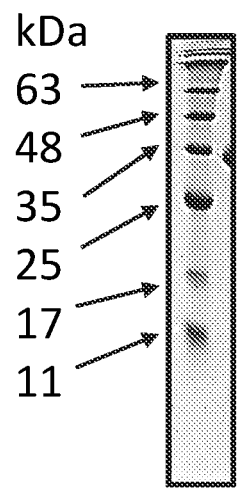
Figure 8A:
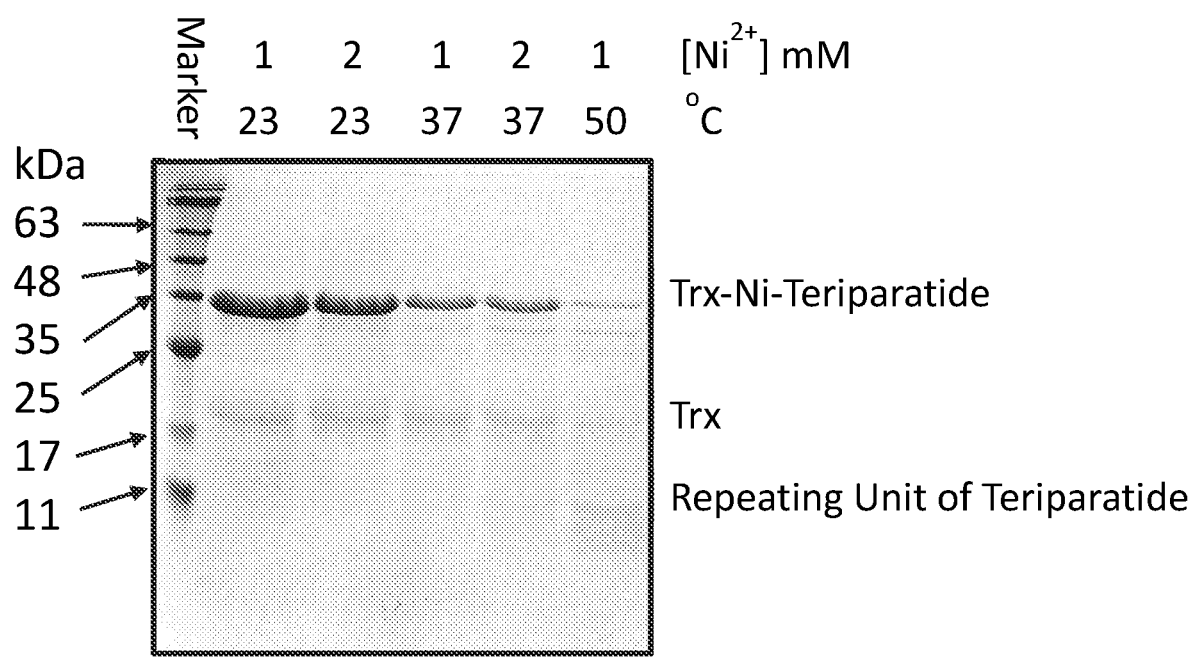
FIGS. 8A-8B show SDS-PAGE (Glycine) analysis of the hydrolysis of thioredoxin tagged teriparatide (four repeats) possessing $Ni^{2+}$ cleavage sequence and its cleavage by 1 and 2 mM of $NiCl_2$ at incubation time of 24 hours and temperatures of 23, 37, and 50° C.
Figure 8B:
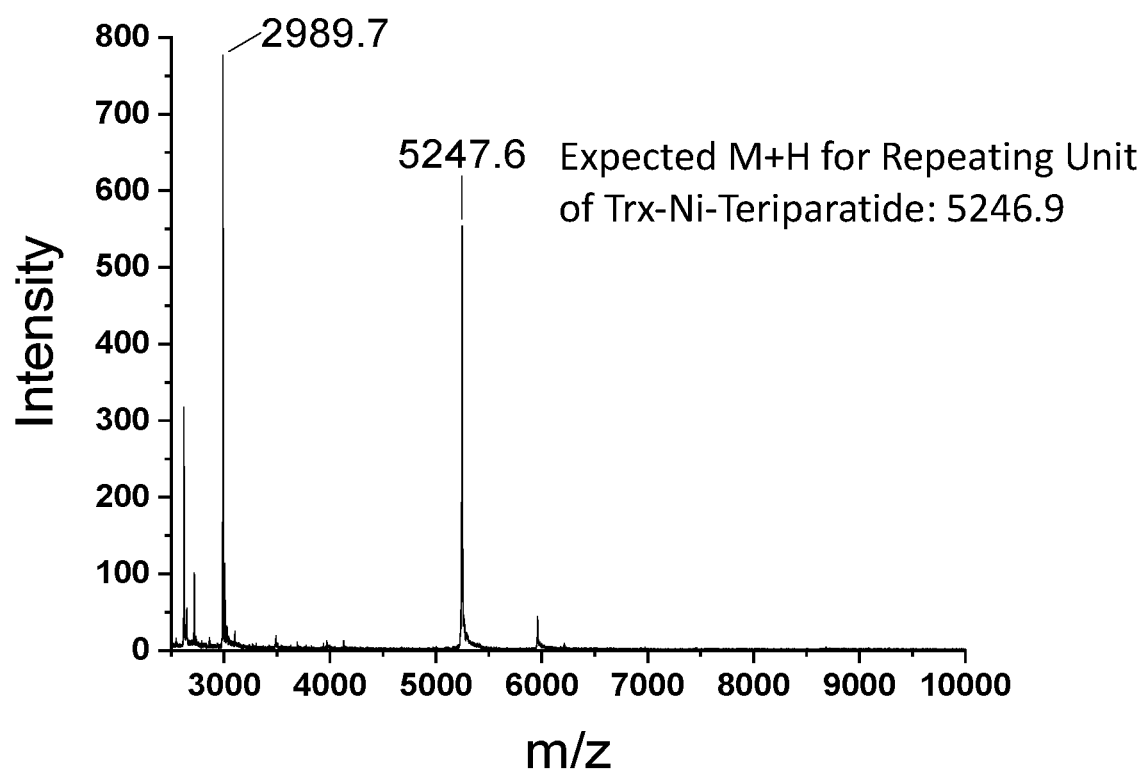

The purified polypeptide, 5 mg, is treated with 50 μg of recombinant histidine tagged Caspase-7 protease at 30° C. in 50 mM HEPES, pH 7.4, 100 mM NaCl, 10% glycerol, 0.1 mM EDTA, 5 mM βME overnight, cleaving the polypeptide at SEQ ID NO: 34 to produce teriparatide and teriparatide linked to the linker peptide SEQ ID NO: 201 (FIG. 7A). Depending on the condition, the products can be obtained in soluble or insoluble forms. Overnight digested samples with high concentration of the protein are precipitated by centrifugation and the pallet is dissolved in 5% Acetonitrile and 0.1% Trifluoroacetic acid. The sample are analyzed by Hi-Pore C18 Bio-rad column. Teriparatide and its repeating unit are normally eluted at 20.2 and 20.4 min. The fraction containing teriparatide and teriparatide attached to the linker sequence are subjected to the Speedvac to evaporate the solvents. The resulting peptides are dissolved in 2 mM $NiCl_2$ in 50 mM Hepes buffer, pH 8.2, 120 mM NaCl at 50° C. overnight, cleaving the intermediate peptide product at the SEQ ID NO: 56 chemical cleavage site to remove the extraneous amino acids, SRHWSDEVD (SEQ ID NO: 202), from the C-terminus of teriparatide (FIG. 7B). The extent of the cleavage is dependent upon the concentration of the enzyme and the amount of the substrate (FIG. 7C). The MALDI-TOF-MS analysis confirms the production of correct Teriparatide with molecular weight of 4117.76. The mixture of teriparatide and its repeating unit obtained from the reverse phase column with a total concentration of approximately 200 ng per microliters is infused to Thermo Q-Exactive orbitrap mass spectrometer at the flow rate of 10 μL per minute. The raw data are obtained by Xcalibur software in the range of 400 to 2000 are deconvoluted by the University of Oxford's Unidec software (FIG. 7E)(REF DOI: 10.1021/acs.analchem.5b00140). The obtained masses are in excellent agreement with the calculated molecular masses. To assess the accessibility the designed caspase cleavage sites, partial hydrolysis of the purified Trx-Ni-Teriparatide is performed (FIG. 7B). Limited hydrolysis of the polypeptide by either caspase-3 or -7, results in 12 possible fragments indicating that all designed enzyme recognition cites are indeed accessible to a similar extent to the protease. Hydrolysis of the purified Trx-Ni-Teriparatide is performed with $NiCl_2$ too. (FIG. 8A). The best temperature for the hydrolysis was 50° C. at 1 mM concentration of $NiCl_2$. MALDI-TOF mass spectrometric analysis of the products with molecular weight under 10 kDa reveals two major peaks at m/z values of 5247.6 and 2989.7; former belonging to the oxidized form of the repeating unit of teriparatide and the latter an impurity (FIG. 8B).

Example 11: Production of Other Peptides of Interest

Recombinant polypeptides containing concatenated repeats comprising the following peptides are engineered in the manner described in detail above for glucagon, liraglutide, and insulin. The product peptides are isolated from the polypeptides utilizing combinations of proteases and carboxypeptidases or proteases and proteolytic chemical agents, also as described:

Exenatide, sermorelin, nesiritide (Natriuretic peptide B), and teduglutide; these peptides cannot be produced using methods utilizing the introduction of an N-terminal cysteine in the linker peptide of tandem repeat-containing polypeptide, as the N-terminus of the peptide becomes modified by the iminothiazolidine-carboxyl group during the cleavage reaction to release the product peptide.

[Cys(Acm)20,31] Epidermal Growth Factor (20-31); production of this peptide utilizing embodiments herein maintains a tag in the product that can be used for purification if proteases other than Kex2 are included in the linker sequence.

ACE2 α1 Helix Sequence; ACE2 peptidase domain (PD) α1 helix is important for binding SARS-CoV-2-RBD of the Spike (S) protein. The 23 residues selected from the ACE2 α1 helix sequence, IEEQAKTFLDKFNHEAEDLFYQS (SEQ ID NO: 111) specifically recognizes SARS-CoV-2-RBD with sub-nanomolar binding. Binding by this peptide to the SARS-CoV-2-RBD may block the entry of the virus into the host cell. Production of this peptide utilizing embodiments herein allows the production of the polypeptide comprising tandem repeats with the peptide, which tandem repeat polypeptide may be used for immunization to produce neutralizing antibodies against COVID-Spike protein receptor.

T1 peptide, GTP-binding Protein Fragment Gα, L-selectin, Peptide Standard 1 (amino acid analysis); these peptides all contain both internal Cys and Met amino acids, and therefore they cannot be expressed with their exact sequence by conventional methods.

While the specification describes particular embodiments of the present invention, those of ordinary skill in the art can devise variations of the present invention without departing from the inventive concept.

The invention claimed is:

1. A method of producing a plurality of product peptides, the method comprising:
   a) expressing a recombinant protein from a nucleic acid sequence encoding the recombinant protein, the recombinant protein comprising a product peptide and one or more repeating units, each of the one or more repeating units comprising a chemical cleavage site, a protease cleavage site and a product peptide, wherein the chemical cleavage site is an amino acid sequence and is a site that leaves no amino acid at the P1 position upon cleavage; wherein the protease cleave site is an amino acid sequence and is a site that leaves no amino acid at the P1' position upon cleavage, the recombinant protein arranged according to formula I $$\text{PP-[CCS-PCS-PP]}_n \quad (I)$$

wherein
      brackets indicate a repeating unit of the one or more repeating units;
      PP is the product peptide;
      CCS is the chemical cleavage site;
      PCS is the protease cleavage site; and
      n is an integer from 1 to 150;
   b) isolating the expressed recombinant protein; and
   c) performing either steps (i) to (iii) or steps (iv) to (vi):
   wherein steps (i) to (iii) comprise:
      (i) cleaving the protease cleavage site of the isolated recombinant protein using a protease that recognizes the protease cleavage site to produce a plurality of intermediate polypeptides, each intermediate polypeptide comprising one of the one or more repeating units;
      (ii) optionally isolating the plurality of intermediate polypeptides; and
      (iii) cleaving the chemical cleavage site of the isolated intermediate polypeptides using a chemical agent that recognizes the chemical cleavage site to produce a plurality of product peptides; wherein each peptide of the plurality of product peptide has its amino acid sequence without any extraneous amino acids; and
   wherein steps (iv) to (vi) comprise:
      (iv) cleaving the chemical cleavage site of the isolated recombinant protein using a chemical agent that recognizes the chemical cleavage site to produce a plurality of intermediate polypeptides, each intermediate polypeptide comprising one of the one or more repeating units;
      (v) optionally isolating the plurality of intermediate polypeptides; and
      (vi) cleaving the protease cleavage site of the isolated intermediate polypeptides using a protease that recognizes the protease cleavage site to produce a plurality of product peptide; wherein each peptide of the plurality of product peptide has its amino acid sequence without any extraneous amino acids.

2. The method of claim 1, wherein the protease cleavage site comprises a caspase cleavage site, an enterokinase cleavage site, a Granzyme B cleavage site, a Factor Xa cleavage site, a Furin protein convertase cleavage site, a Kexin cleavage site, or a neuroendocrine convertase cleavage site.

3. The method of claim 1, wherein the chemical cleavage site comprises a $Ni^{2+}$ cleavage site, a 2-nitro-5-thiocyanobenzoic acid cleavage site, or a $Pd^{2+}$ cleavage site.

4. The method of claim 1, wherein in step (b) and/or in step (c) the recombinant protein is isolated using affinity purification or liquid chromatography.

5. The method of claim 1, wherein each of the one or more repeating units further comprises a linking sequence located between the chemical cleavage site and the protease cleavage site, the linker sequence being an amino acid sequence.

6. The method of claim 5, wherein the recombinant protein comprises formula II:

$$\text{PP-[CCS-L}_{nk}\text{-PCS-PP]}_n \quad (II)$$

wherein
   brackets indicate a repeating unit of the one or more repeating units;
   PP is the product peptide;
   CCS is the chemical cleavage site;
   PCS is the protease cleavage site;
   $L_{nk}$ is a linker sequence; and
   n is an integer from 1 to 150.

7. The method of claim 5, wherein the linker sequence comprises the amino acids Glycine, Alanine, Serine, or any combination thereof.

8. The method of claim 5, wherein the linker sequence is any one of SEQ ID NOs: 57-83.

9. The method of claim 1, wherein the recombinant protein further comprising an amino acid sequence that is an affinity purification tag or an amino acid sequence that is a solubilization tag at the amino-terminal end of the recombinant protein.

10. The method of claim 9, wherein the recombinant protein comprises formula III:

$$\text{[TAG]-L}_{nk}\text{-PCS-PP-[CCS-L}_{nk}\text{-PCS-PP]}_n \quad (III)$$

wherein
   brackets indicate a repeating unit of the one or more repeating units;
   PP is the product peptide;
   CCS is the chemical cleavage site;
   PCS is the protease cleavage site;
   $L_{nk}$ is a linker sequence; and
   TAG is the affinity purification tag or the solubilization tag; and
   n is an integer from 1 to 150.

11. The method of claim 1, wherein the recombinant protein further comprising an amino acid sequence that is an affinity purification tag or an amino acid sequence that is a solubilization tag at the carboxyl-terminal end of the recombinant protein.

12. The method of claim 11, wherein the recombinant protein comprises formula IV:

$$\text{PP-[CCS-L}_{nk}\text{-PCS-PP]}_n\text{-CCS-[TAG]} \quad (IV)$$

wherein
   brackets indicate a repeating unit of the one or more repeating units;
   PP is the product peptide;
   CCS is the chemical cleavage site;
   PCS is the protease cleavage site;
   $L_{nk}$ is a linker sequence; and
   TAG is the affinity purification tag or the solubilization tag; and
   n is an integer from 1 to 150.

13. The method of claim 1, further comprising the step of purifying the plurality of product peptides.

14. The method of claim 13, wherein the plurality of product peptides are isolated using affinity purification or liquid chromatography.

15. A method of producing a plurality of product peptides, the method comprising:
   a) expressing a recombinant protein from nucleic acid sequence encoding the recombinant protein, the recombinant protein comprising a first product peptide and one or more repeating units, each of the one or more repeating units comprising in linear order a chemical cleavage site, a protease cleavage site and a second product peptide, wherein the second product peptide is a different peptide than the first product peptide, wherein the chemical cleavage site is an amino acid sequence and is a site that leaves no amino acid at the P1 position upon cleavage; wherein the protease cleave site is an amino acid sequence and is a site that leaves no amino acid at the P1' position upon cleavage;
   b) isolating the expressed recombinant protein; and
   c) performing either steps (i) to (iii) or steps (iv) to (vi): wherein steps (i) to (iii) comprise:
      (i) cleaving the protease cleavage site of the isolated recombinant protein using a protease that recognizes the protease cleavage site to produce a plurality of intermediate polypeptides, each intermediate polypeptide comprising one of the one or more repeating units;
      (ii) optionally isolating the plurality of intermediate polypeptides; and
      (iii) cleaving the chemical cleavage site of the isolated intermediate polypeptides using a chemical agent that recognizes the chemical cleavage site to produce a plurality of product peptides; wherein each peptide of the plurality of product peptide has its amino acid sequence without any extraneous amino acids; and wherein steps (iv) to (vi) comprise:
      (iv) cleaving the chemical cleavage site of the isolated recombinant protein using a chemical agent that recognizes the chemical cleavage site to produce a plurality of intermediate polypeptides, each intermediate polypeptide comprising one of the one or more repeating units;
      (v) optionally isolating the plurality of intermediate polypeptides; and
      (vi) cleaving the protease cleavage site of the isolated intermediate polypeptides using a protease that recognizes the protease cleavage site to produce a plurality of product peptide; wherein each peptide of the plurality of product peptide has its amino acid sequence without any extraneous amino acids.

16. The method of claim 15, wherein when the one or more repeating units comprise two or more repeating units, the second product peptide present in each repeating unit of the two or more repeating units is a peptide different than the second product peptide present in the other repeating unit of the two or more repeating units.

17. The method of claim 15, wherein the protease cleavage site comprises a caspase cleavage site, an enterokinase cleavage site, a Granzyme B cleavage site, a Factor Xa cleavage site, a Furin protein convertase cleavage site, a Kexin cleavage site, or a neuroendocrine convertase cleavage site.

18. The method of claim 15, wherein the chemical cleavage site comprises a $Ni^{2+}$ cleavage site, a 2-nitro-5-thiocyanobenzoic acid cleavage site, or a $Pd^{2+}$ cleavage site.

19. The method of claim 15, wherein each of the one or more repeating units further comprises a linking sequence located between the chemical cleavage site and the protease cleavage site, the linker sequence being an amino acid sequence.

20. The method of claim 19, wherein the linker sequence comprises the amino acids Glycine, Alanine, Serine, or any combination thereof or is any one of SEQ ID NOs: 57-83.

* * * * *